(12) United States Patent
Vuligonda et al.

(10) Patent No.: US 11,919,848 B2
(45) Date of Patent: Mar. 5, 2024

(54) RXR AGONIST SALT FORM, POLYMORPHS THEREOF, AND USES THEREOF

(71) Applicant: Io Therapeutics, Inc., Spring, TX (US)

(72) Inventors: Vidyasagar Vuligonda, Spring, TX (US); Martin E. Sanders, Spring, TX (US); Shanming Kuang, Collegeville, PA (US); Harsh Shailesh Shah, Monroe, NJ (US)

(73) Assignee: Io Therapeutics, Inc., Spring, TX (US)

( * ) Notice: Subject to any disclaimer, the term of this patent is extended or adjusted under 35 U.S.C. 154(b) by 0 days.

(21) Appl. No.: 18/183,747

(22) Filed: Mar. 14, 2023

(65) Prior Publication Data
US 2023/0295069 A1    Sep. 21, 2023

Related U.S. Application Data

(60) Provisional application No. 63/320,159, filed on Mar. 15, 2022.

(51) Int. Cl.
*C07C 51/43* (2006.01)

(52) U.S. Cl.
CPC .......... *C07C 51/43* (2013.01); *C07B 2200/13* (2013.01)

(58) Field of Classification Search
CPC .............................. C07C 51/43; C07B 2200/13
See application file for complete search history.

(56) References Cited

U.S. PATENT DOCUMENTS

| 5,917,082 A | * | 6/1999 | Vuligonda ............. C07C 57/50 |
| | | | 562/490 |
| 10,590,059 B2 | * | 3/2020 | Chandraratna ......... C07C 33/38 |
| 2011/0160240 A1 | | 6/2011 | Ryckman et al. |
| 2021/0139404 A1 | | 5/2021 | Chandraratna et al. |

OTHER PUBLICATIONS

International Search Report and Written Opinion, dated Jul. 18, 2023, for International Application No. PCT/US2023/064325.
International Patent Application Serial No. PCT/US2023/064325 filed Mar. 14, 2023.
Yu, H et al. "Venlafaxine Caffeic Acid Salt: Synthesis, Structural Characterization, and Hypoglycemic Effect Analysis" pp. 13895-13903. ACS Omega. vol. 6, No. 21. May 17, 2021.

* cited by examiner

*Primary Examiner* — Sikarl A Witherspoon
(74) *Attorney, Agent, or Firm* — K&L Gates LLP; Louis C. Cullman; Michelle Glasky Bergman

(57) ABSTRACT

Provided herein are salt and solid forms of (2E,4E)-3-methyl-5-((1S,2S)-2-methyl-2-(5,5,8,8-tetramethyl-5,6,7,8-tetrahydronaphthalen-2-yl)cyclopropyl)penta-2,4-dienoic acid, including a Tris salt form of (2E,4E)-3-methyl-5-((1S, 2S)-2-methyl-2-(5,5,8,8-tetramethyl-5,6,7,8-tetrahydronaphthalen-2-yl)cyclopropyl)penta-2,4-dienoic acid, and polymorphs thereof, methods of preparing the compounds, and their uses.

20 Claims, 46 Drawing Sheets

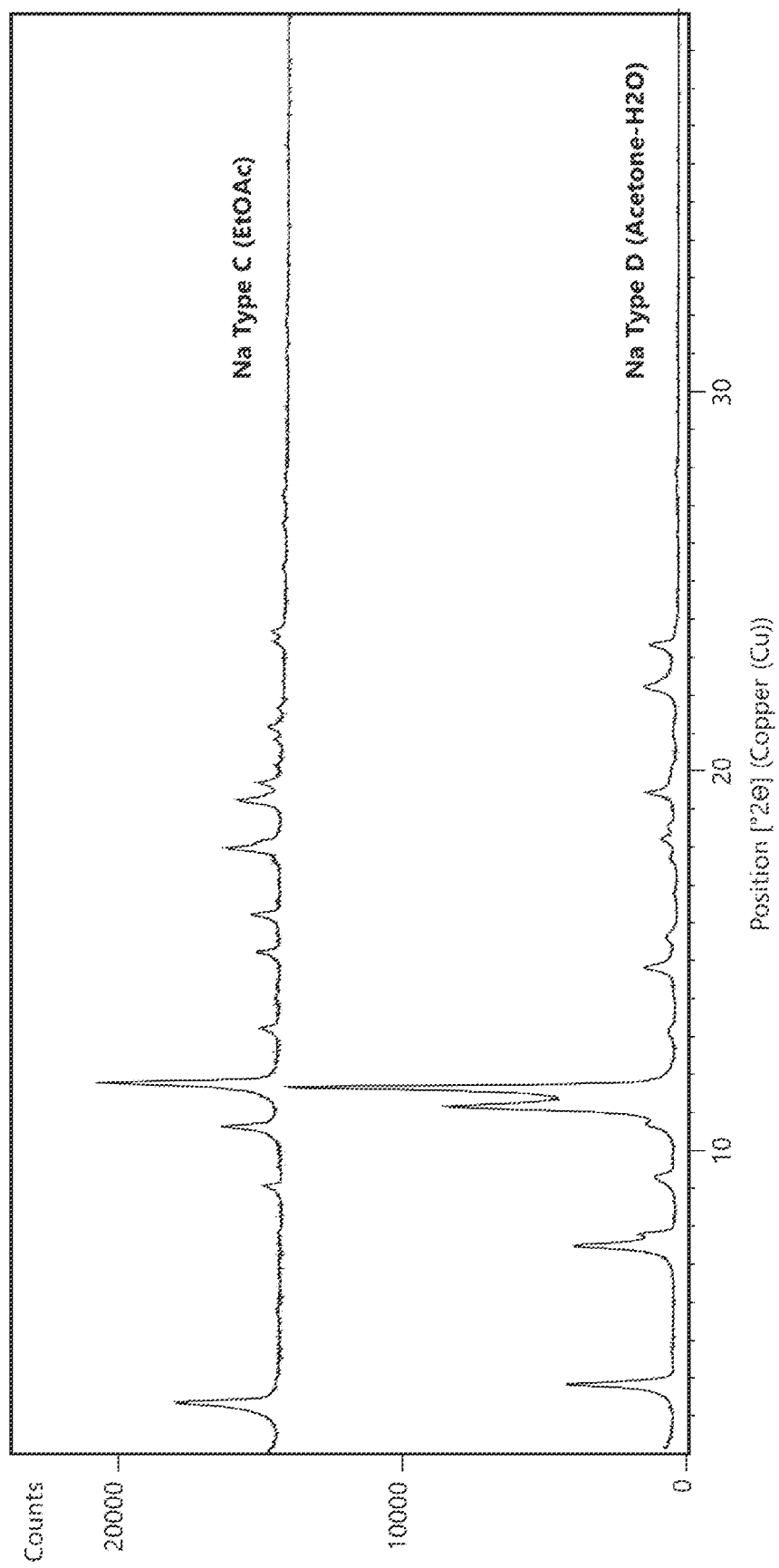

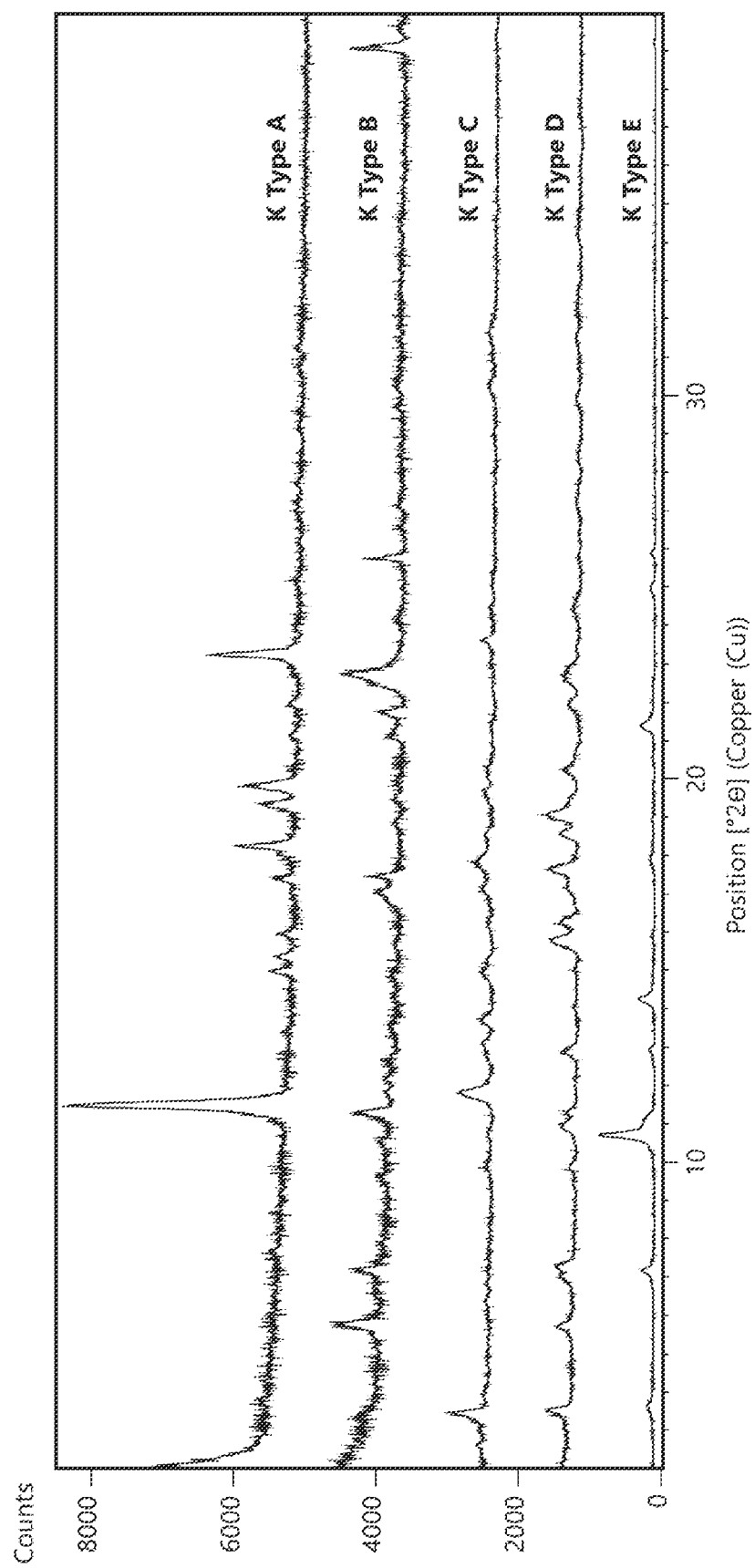

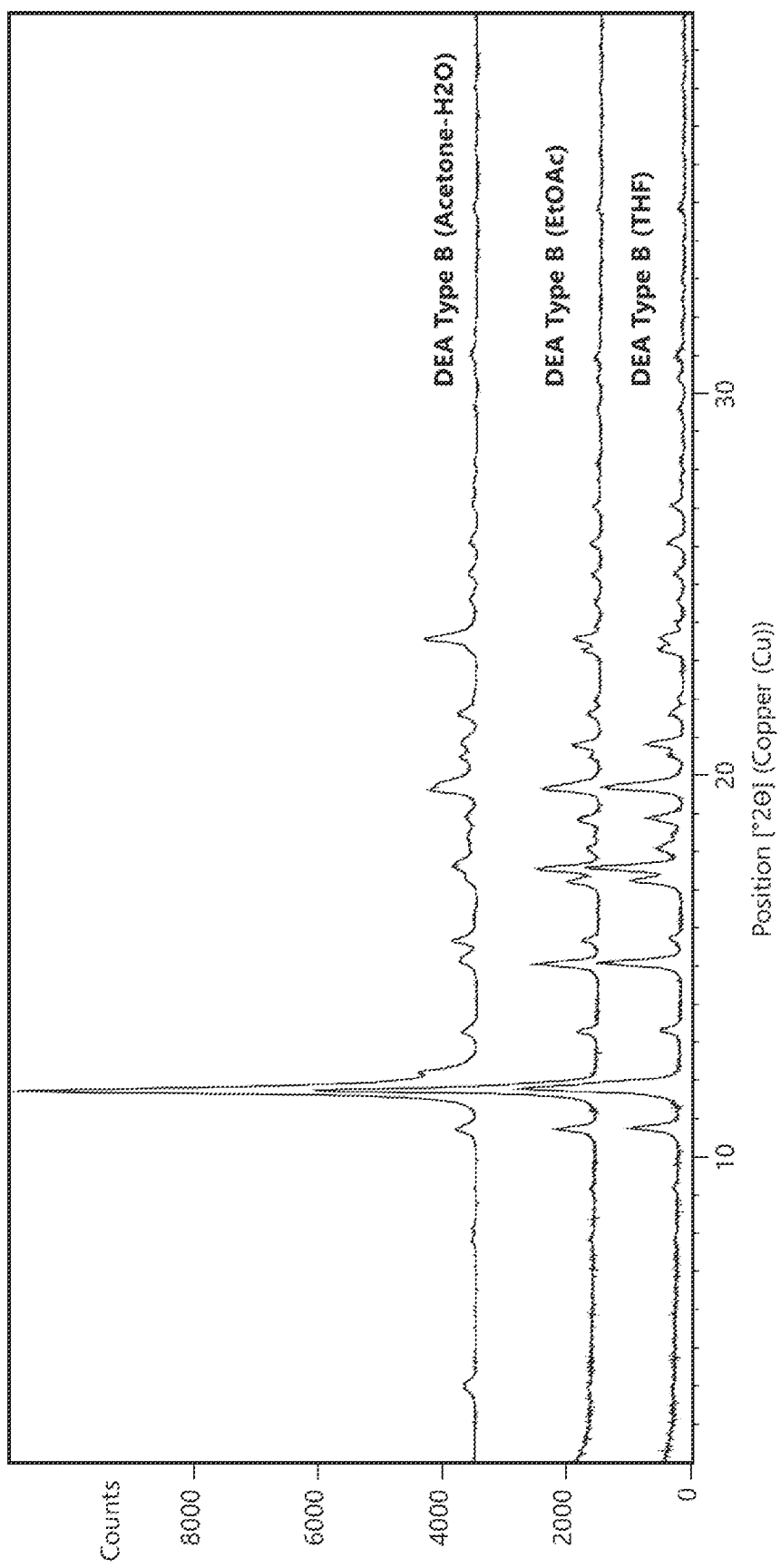

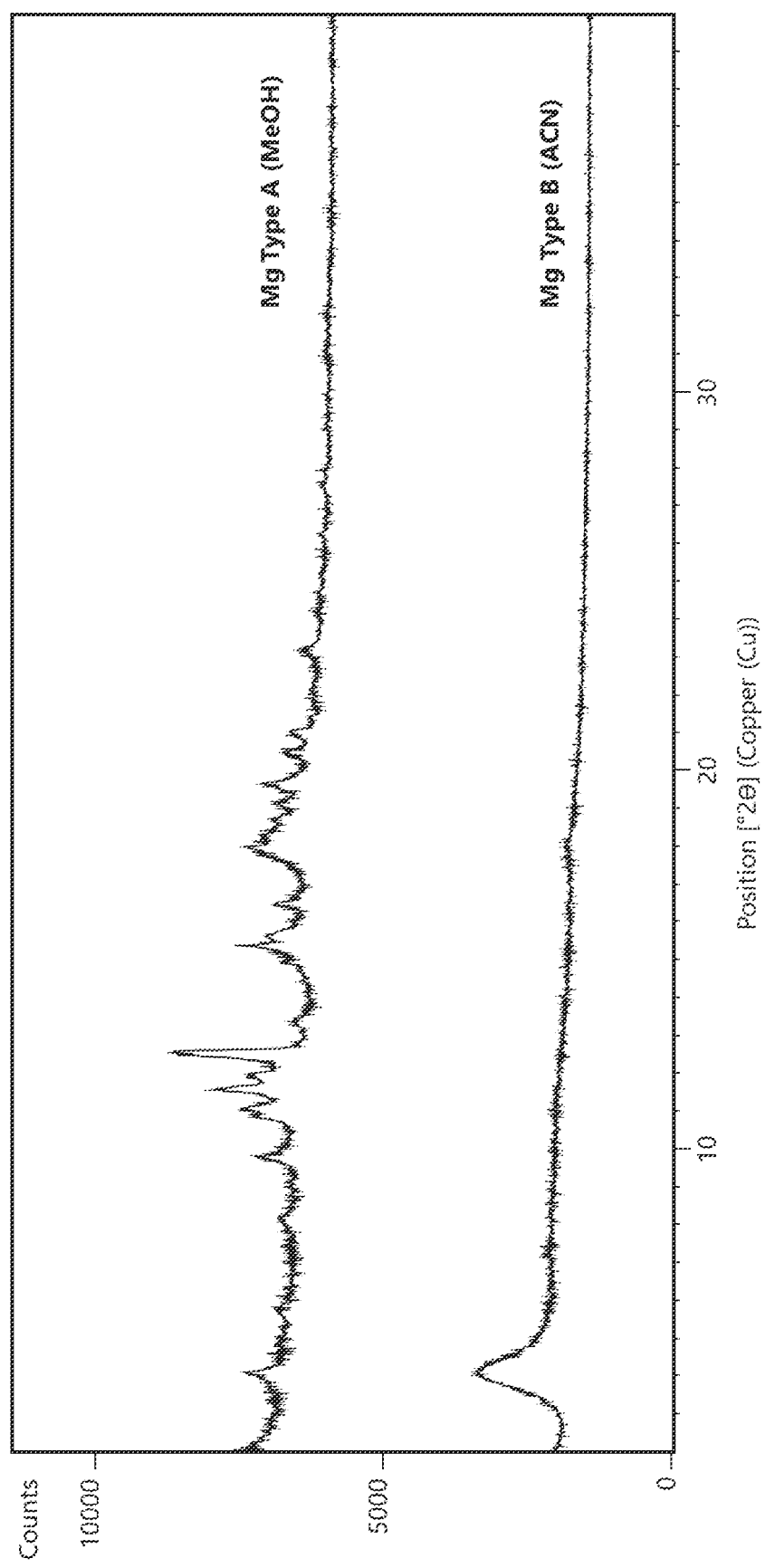

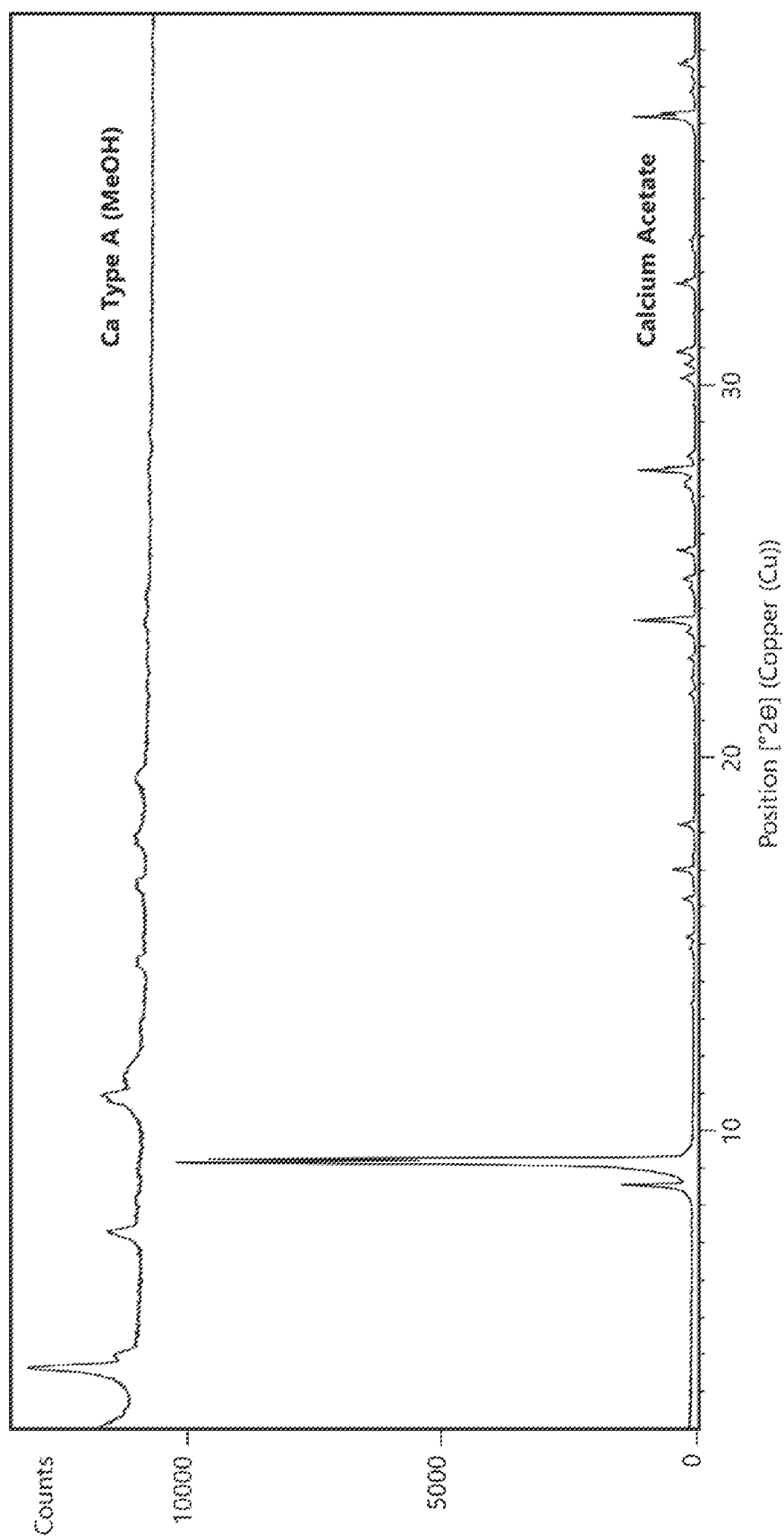

RXR AGONIST SALT FORM, POLYMORPHS THEREOF, AND USES THEREOF

RELATED APPLICATIONS

This application claims priority of U.S. Provisional Patent Application No. 63/320,159, filed Mar. 15, 2022, the entire content of which is incorporated herein by reference.

FIELD

This disclosure generally describes (2E,4E)-3-methyl-5-((1S,2S)-2-methyl-2-(5,5,8,8-tetramethyl-5,6,7,8-tetrahydronaphthalen-2-yl)cyclopropyl)penta-2,4-dienoic acid (Compound 1) as a tris salt, a diethylamine salt, a lysine salt, a glycine salt, a choline salt, an ammonium salt, a magnesium salt, a calcium salt, a potassium salt, or a sodium salt form. This disclosure also generally describes (2E,4E)-3-methyl-5-((1S,2S)-2-methyl-2-(5,5,8,8-tetramethyl-5,6,7,8-tetrahydronaphthalen-2-yl)cyclopropyl)penta-2,4-dienoic acid (Compound 1) as a tris(hydroxymethyl)aminomethane (Tris) salt form and polymorphic forms thereof. Compositions comprising such forms, including pharmaceutical compositions and formulations for particular routes of administration, are also described. Therapeutic or prophylactic uses of such forms and compositions as a monotherapy or in combination with one or more other active pharmaceutical agents, including thyroid hormone or neurotrophic factors, are also described.

BACKGROUND

Compound 1, and its synthetic preparation, is described in U.S. Pat. Nos. 5,917,082 and 10,590,059, the entire content of each of which are incorporated herein by reference. Its chemical structure is shown below.

Compound 1

Compound 1 is a clinical stage, potent, and highly selective retinoid X receptor (RXR) agonist that is brain penetrant, promotes differentiation of oligodendrocyte precursor cells, and is a clinical stage experimental therapeutic for various diseases, including prostate cancer, lung cancers, and other cancers. RXRs modulate functions associated with differentiation, inhibition of cell growth, apoptosis, and metastasis. Preclinical studies with rexinoids—agonists of RXRs—suggest that selective activation of RXRs may be useful in treating a variety of diseases associated with the biochemical functions modulated by RXR.

Compound 1, which includes a carboxylic acid moiety, is lipophilic. Though useful in certain contexts, this feature limits the ways in which Compound 1 can be formulated. Thus, what is needed are new salt and polymorphic forms of Compound 1 in order to access ways to formulate the compound that were otherwise unavailable due, at least in part, to its lipophilicity, and to improve its therapeutic utility.

SUMMARY

Provided herein are salt forms, including a Tris salt, of Compound 1 and polymorphic forms thereof, compositions comprising one or more of them, uses of them, methods of preparing them, and kits comprising them.

BRIEF DESCRIPTION OF THE DRAWINGS

FIG. 9C shows XRPD traces of Compound 1 and the Form C/D sodium (Na) salts of Compound 1: Na Type C (from ethyl acetate); and Na Type D (from acetone-$H_2O$ 5:1).

FIG. 11 shows XRPD traces of the Form A/B/C/D/E potassium (K) salts of Compound 1: K Type A (from ACN; K Type B (from THF); K Type C (from evaporation of methanol); K Type D (from evaporation of isopropanol); and K Type E (from acetone-$H_2O$ 5:1).

FIG. 13B shows XRPD traces of the Form B diethylamine (DEA) salt of Compound 1: DEA Type B (from acetone-$H_2O$ 5:1); DEA Type B (from ethyl acetate); and DEA Type B (from tetrahydrofuran).

FIG. 20 shows XRPD traces of the Form A/B magnesium (Mg) salts of Compound 1: Mg Type A (from methanol); and Mg Type B (from acetonitrile).

FIG. 22 shows an XRPD trace of calcium acetate and the Form A calcium (Ca) salt of Compound 1: calcium acetate; and Ca Type A (from methanol).

DETAILED DESCRIPTION

Figure 1:
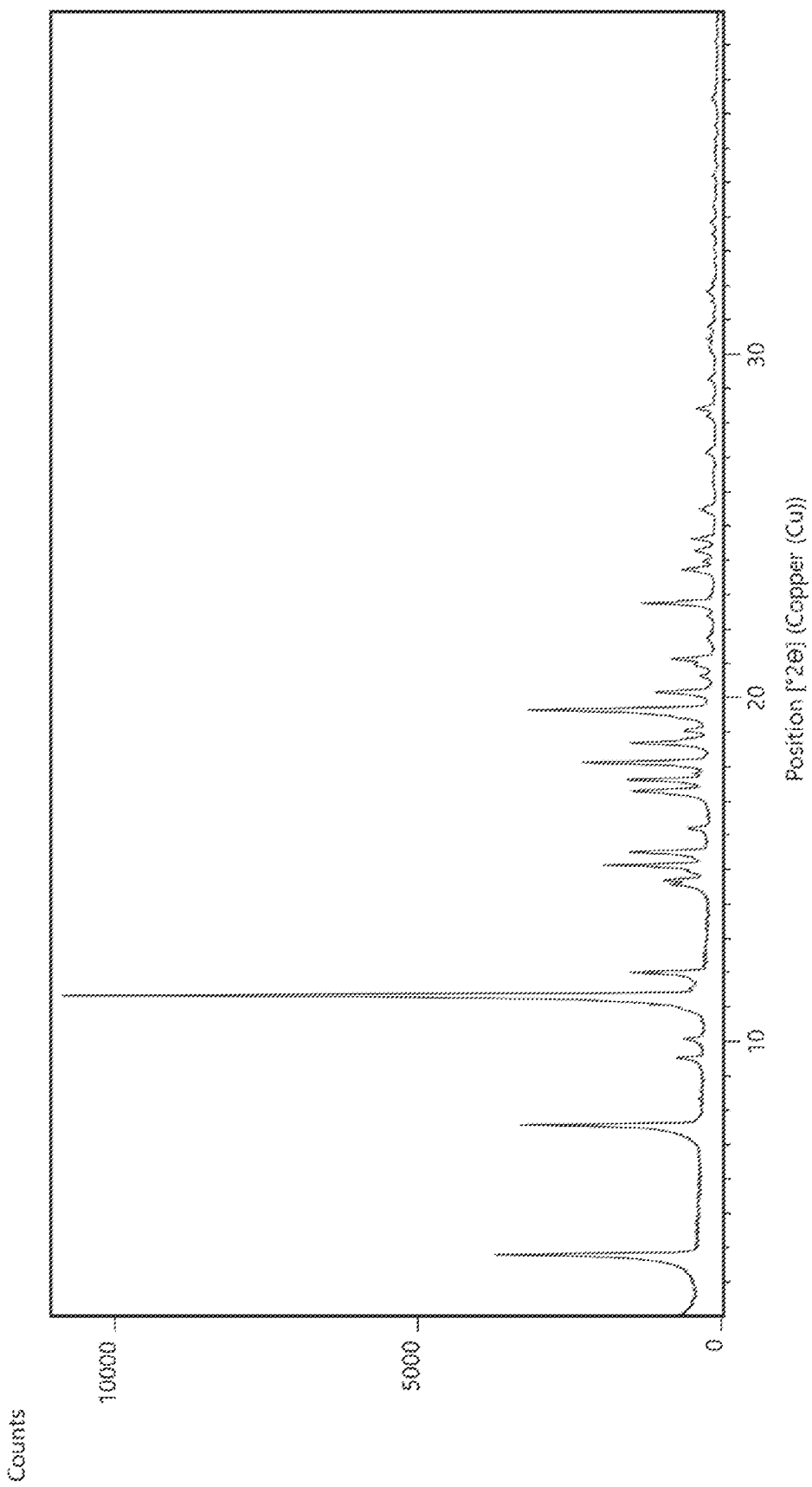
FIG. 1 shows an x-ray powder diffraction (XRPD) trace of the Form A Tris salt of Compound 1.

It has been discovered that salt forms, including a Tris salt form, of Compound 1 have certain advantages over the corresponding Compound 1, i.e. as a free acid. The chemical structure of Compound 1 as a Tris salt form is shown below. When used medically, Tris may be referred to as tromethamine or THAM. The Tris salt form of Compound 1 may be prepared by, for example, combining equimolar amounts of Compound 1 and Tris in a suitable solvent, such as an alcohol solvent or an aqueous solvent, to prepare a solution, and subsequent evaporation of the solvent. Salt forms having other cations may be similarly prepared.

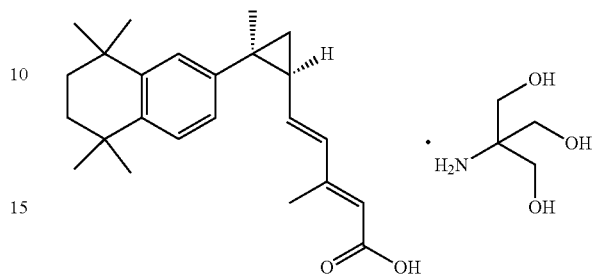

A Representation of a Tris Salt Form of Compound 1

It has also been discovered that Compound 1 as a Tris salt has a kinetic aqueous solubility of approximately an order of magnitude, or more, compared to Compound 1 (see Table 1).

TABLE 1

Observed kinetic aqueous solubility (mg/mL) at 37° C.

| Sample | Water | | Synthetic Gastric Fluid | | Fed Synthetic Small Intestinal Fluid | | Fasting Synthetic Small Intestinal Fluid | |
| --- | --- | --- | --- | --- | --- | --- | --- | --- |
| | S | pH | S | pH | S | pH | S | pH |
| 1 Hr | | | | | | | | |
| Tris Form A | 0.29 | 2.68 | ND | 1.76 | 2.54 | 5.91 | 0.74 | 6.93 |
| Compound 1 | 0.03 | 7.78 | ND | 1.67 | 0.10 | 5.09 | 0.05 | 6.48 |
| 4 Hrs | | | | | | | | |
| Sample | S | pH | S | pH | S | pH | S | pH |
| Tris Form A | 0.17 | 3.21 | ND | 1.96 | 0.41 | 6.84 | 0.83 | 7.83 |
| Compound 1 | 0.03 | 7.83 | 0.02 | 1.78 | 0.10 | 5.17 | 0.06 | 6.88 |
| 24 Hrs | | | | | | | | |
| Sample | S | pH | S | pH | S | pH | S | pH |
| Tris Form A | 0.14 | 9.3 | ND | 2.12 | 0.34 | 7.33 | 0.86 | 9.37 |
| Compound 1 | 0.01 | 8.33 | ND | 1.92 | 0.44 | 5.21 | 0.04 | 7.50 |

ND = No Detectable signal by HPLC.

It has also been discovered that the Tris salt of Compound 1 may be prepared as one or more solid forms. In some embodiments the solid form is a crystalline solid form. In some embodiments, the solid form is an anhydrate. In some embodiments, the solid form is a hydrate. In some embodiments, the hydrate is a hemihydrate, a mono-hydrate, or a di-hydrate, e.g. (Compound 1)(Tris)($H_2O$)$_{0.5}$, (Compound 1)(Tris)($H_2O$), or (Compound 1)(Tris)($H_2O$)$_2$, respectively.

It was also found that the Tris salt of Compound 1 has differential thermodynamic solubility in certain solvents at room temperature as shown in Table 2. For example, the solubility of Compound 1 in methanol is lower than the solubility of the Form A Tris salt of Compound 1 in methanol, whereas the solubility of Compound 1 in ethanol, isopropanol, or butanol is higher than the solubility of the Form A Tris salt of Compound 1 in ethanol, isopropanol, or butanol. Surprisingly, the thermodynamic solubility of Compound 1 in water at room temperature is higher than that of the Form A Tris salt of Compound 1. Furthermore, the Form A Tris salt of Compound 1 and the corresponding free acid (Compound 1) have poor or undetectable kinetic solubility in synthetic gastric fluid, but the kinetic solubility of the Form A Tris salt of Compound 1 becomes significantly higher in synthetic small intestinal fluid whereas that of Compound 1 does not (see Table 1).

It was also found that solid forms of additional salts of Compound 1 could be prepared. For example, crystalline forms of the sodium (Na), potassium (K), diethylamine, lysine, ammonium, magnesium (Mg), or calcium (Ca) salt of Compound 1 were prepared. See FIGS. 7-23 for XRPD, DSC, and TGA traces of Tris salt Types C/D, Na salt Types A/B/C/D, K salt Types A/B/C/D/E, diethylamine salt Types A/B/C, Lysine salt Types A/B/C/D, ammonium salt Types A/B/C/D, Mg salt Types A/B, and Ca salt Types A/B/C of Compound 1, and Table 2a for corresponding endothermic transitions. Glycine and choline salts of Compound 1 were prepared as amorphous solid forms. See Table 2 for thermodynamic solubility data. The methods and uses described herein apply to these amorphous and crystalline solid forms as well. For example, where reference to a Tris salt of Compound 1 is made, a corresponding alternate salt form may be contemplated in place of the Tris salt form.

TABLE 2

Approximate solubility of Compound 1 and a Tris salt of Compound 1.

| Solvent | Approximate Solubility (mg/mL) | |
| --- | --- | --- |
| | Compound 1 (Free Acid) | TRIS salt Form A |
| 2-Butanol | 108.9-140.0 | >15.00 |
| Ethanol | 74.9-91.5 | >40.00 |
| Isopropanol | 71.8-87.8 | 8.83-10.60 |
| Methanol | 57.4-73.1 | >88.00 |
| Water | 0.03 | 0.29 |

TABLE 2a

Observed DSC thermogram endothermic transition temperatures of various salts of Compound 1.

| Form of Compound 1 | Temperature(s) (° C.) |
| --- | --- |
| Free acid | 48.51, 111.94, 127.74 |
| Tris Type A | 153.50 |
| Tris Type B | 149.67 |
| Tris Type C | 94.24, 152.11 |
| Tris Type D | 60.87, 153.70 |
| Na Type A | 86.32 |
| Na Type B | 92.74 |
| Na Type C | 85.05 |
| Na Type D | 134.73 |
| K Type A | 61.41 |
| K Type B | 97.76 |
| K Type C | Not Collected |
| K Type D | 102.57 |
| K Type E | 100.29 |
| diethylamine Type A | 99.82 |
| diethylamine Type B | 109.62 |
| diethylamine Type C | 109.50 |
| lysine Type A | 46.66, 131.44, 183.90 |
| lysine Type B | 48.39, 117.40, 133.68, 189.55 |
| lysine Type C | 127.80, 186.84 |
| lysine Type D | 93.90, 132.60, 166.81, 181.85 |

TABLE 2a-continued

Observed DSC thermogram endothermic transition temperatures of various salts of Compound 1.

| Form of Compound 1 | Temperature(s) (° C.) |
| --- | --- |
| ammonium Type A | 75.83, 144.23 |
| ammonium Type B | 78.13, 141.99 |
| ammonium Type C | 87.55, 127.83, 144.32 |
| ammonium Type D | 87.91, 125.76, 143.36 |
| Mg Type A | 95.70, 136.50 |
| Mg Type B | 70.65, 137.99 |
| Ca Type A | 127.19 |
| Ca Type B | Not Collected |
| Ca Type C | Not Collected |

Definitions

Certain terms, whether used alone or as part of a phrase or another term, are defined below.

The articles "a" and "an" refer to one or to more than one of the grammatical object of the article.

Numerical values relating to measurements are subject to measurement errors that place limits on their accuracy. For this reason, all numerical values provided herein, unless otherwise indicated, are to be understood as being modified by the term "about." Accordingly, the last decimal place of a numerical value provided herein indicates its degree of accuracy. Where no other error margins are given, the maximum margin is ascertained by applying the rounding-off convention to the last decimal place or last significant digit when a decimal is not present in the given numerical value.

The term "amelioration" means a lessening of severity of at least one indicator of a condition or disease, such as a delay or slowing in the progression of one or more indicators of a condition or disease. The severity of indicators may be determined by subjective or objective measures which are known to those skilled in the art.

The terms "composition" and "pharmaceutical composition" refer to a mixture of at least one compound described herein with a pharmaceutically acceptable carrier. The pharmaceutical composition facilitates administration of the compound to a patient or subject. Multiple techniques of administering a compound exist including, but not limited to, intravenous, oral, aerosol, parenteral, ophthalmic, nasal, pulmonary, and topical administration.

The terms "effective amount" and "therapeutically effective amount" refer to an amount of therapeutic compound, such as a compound described herein, administered to a subject, either as a single dose or as part of a series of doses, which is effective to produce a desired therapeutic effect. In general, the therapeutically effective amount can be estimated initially either in cell culture assays or in mammalian animal models, for example, in non-human primates, mice, rabbits, dogs, or pigs. The animal model may also be used to determine the appropriate concentration range and route of administration. Such information can then be used to determine useful doses and routes for administration in non-human subjects and human subjects.

The term "pharmaceutically acceptable carrier" means a pharmaceutically acceptable material, composition or carrier, such as a liquid filler, solid filler, stabilizer, dispersing agent, suspending agent, diluent, excipient, thickening agent, solvent, or encapsulating material, involved in carrying or transporting at least one compound described herein within or to the patient such that the compound may perform its intended function. A given carrier must be "acceptable" in the sense of being compatible with the other ingredients of a particular formulation, including the compounds described herein, and not injurious to the patient. Other ingredients that may be included in the pharmaceutical compositions described herein are known in the art and described, for example, in "Remington's Pharmaceutical Sciences" (Genaro (Ed.), Mack Publishing Co., 1985), the entire content of which is incorporated herein by reference.

The term "refractory disease" refers to a disease that continues to progress during treatment with a pharmaceutical ingredient other than the compounds provided herein, partially responds to the other treatment, or transiently responds to the other treatment. The term may be applied to each of the diseases referred to herein.

The terms "treatment" or "treating" refer to the application of one or more specific procedures used for the amelioration of a disease. A "prophylactic" treatment, refers to reducing the rate of progression of the disease or condition being treated, delaying the onset of that disease or condition, or reducing the severity of its onset.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the described subject matter and does not pose a limitation on the scope of the subject matter otherwise claimed. No language in the specification should be construed as indicating any non-claimed element essential to practicing the described subject matter.

Groupings of alternative elements or embodiments of this disclosure are not to be construed as limitations. Each group member may be referred to and claimed individually or in any combination with other members of the group or other elements found herein. Furthermore, a recited member of a group may be included in, or excluded from, another recited group for reasons of convenience or patentability. When any such inclusion or exclusion occurs, the specification is deemed to contain the group as modified thus fulfilling the written description of all Markush groups used in the appended claims.

References have been made to patents and printed publications throughout this specification, each of which are individually incorporated herein by reference in their entirety.

It is to be understood that the embodiments of this disclosure are illustrative. Accordingly, the present disclosure is not limited to that precisely as shown and described.

Compounds

In some embodiments, provided herein are a Tris salt of Compound 1 and polymorphs thereof (e.g., solid forms, amorphous forms, and crystalline forms). The Tris salt forms of Compound 1 may be included in any compositional form, including liquid, gel, syrup, powder, or solid form.

Each polymorph described herein can be uniquely identified by several different analytical parameters, either alone or in combination, including x-ray diffraction (XRD) patterning (e.g., x-ray powder diffraction (XRPD)), differential scanning calorimetry (DSC), thermogravimetric analysis (TGA), or melting point (MP), to name a few.

The Tris salt forms of Compound 1 provided herein are useful in various processes for the preparation of pharmaceutical compositions comprising one or more of the salt forms. Accordingly, the salts and polymorphs provided herein, as well as compositions comprising them, are useful in modulating RXR, and thereby are useful in treating diseases associated with RXR modulation.

Broadly, provided herein are Tris salt forms of Compound 1. In some embodiments, the salt form is a solid salt form. In some embodiments, the solid salt form is a crystalline salt form.

Figure 3:
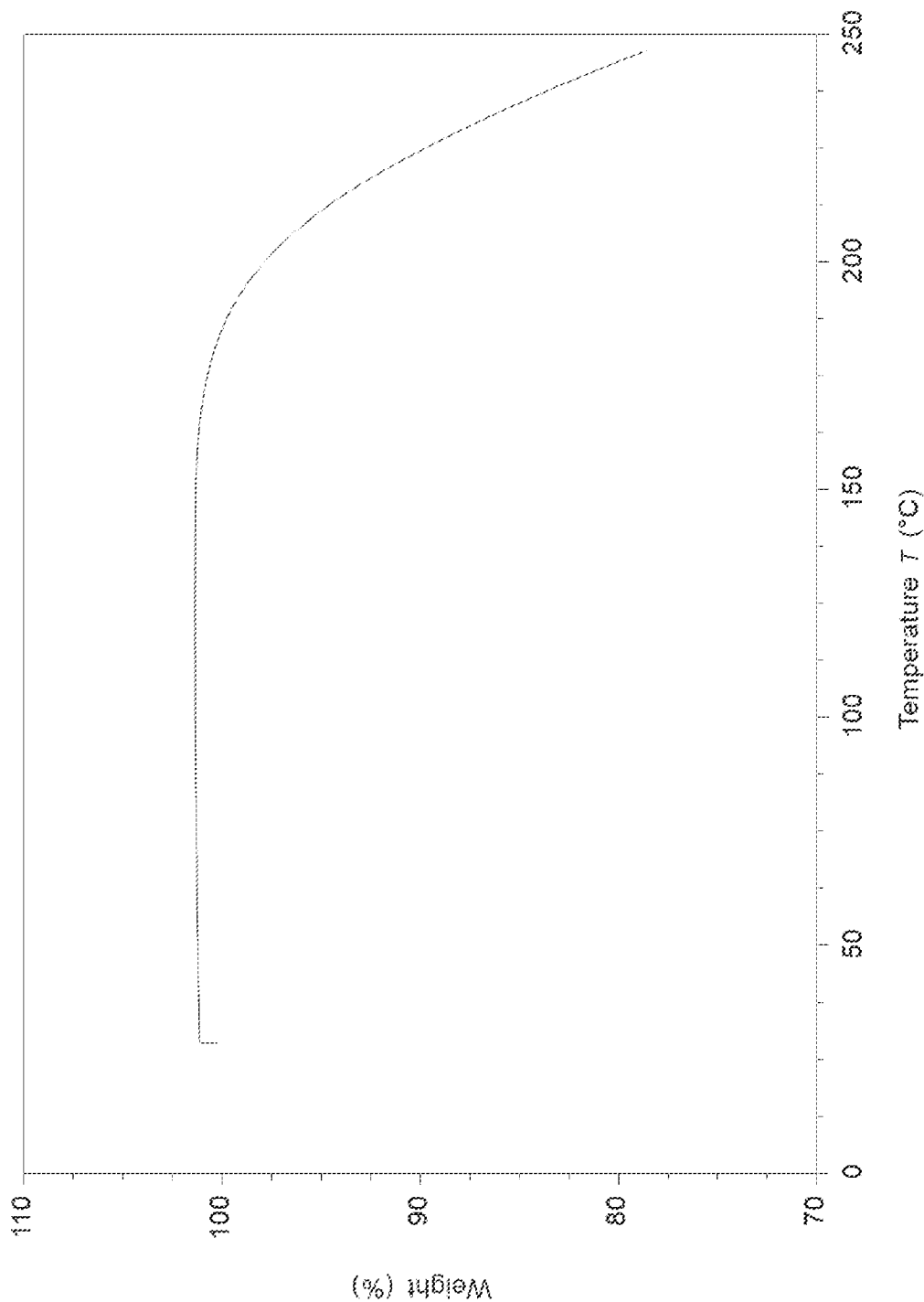
FIG. 3 shows a thermogravimetric analysis (TGA) trace of the Form A Tris salt of Compound 1.

In some embodiments, the crystalline salt form is Form A. In some embodiments, Form A is an anhydrate form. In some embodiments, Form A is characterized by data comprising one or more of the following:
  a. one or more XRPD signals, in terms of 2-theta (2θ), at 3.8, 7.6, 11.3, 18.1, or 19.6±0.2°;
  b. one or more XRPD signals, in terms of 2θ, at 10.1, 12.0, 19.0, or 24.3±0.2°;
  c. a DSC thermogram comprising an endothermic transition at 154±3° C.;
  d. TGA trace as shown in FIG. 3.

In some embodiments, the crystalline salt form is Form B. In some embodiments, Form B is a hydrate form. In some embodiments, Form B is characterized by data comprising one or more of the following:
  e. one or more XRPD signals, in terms of 2θ, at 3.9, 11.5, 18.3, 19.9, or 23.2±0.2°;
  f. one or more XRPD signals, in terms of 2θ, at 19.9, 23.2, or 26.9±0.2°;
  g. a DSC thermogram comprising an endothermic transition at 150±3° C.; or
  h. TGA trace as in FIG. 6.

Figure 4:
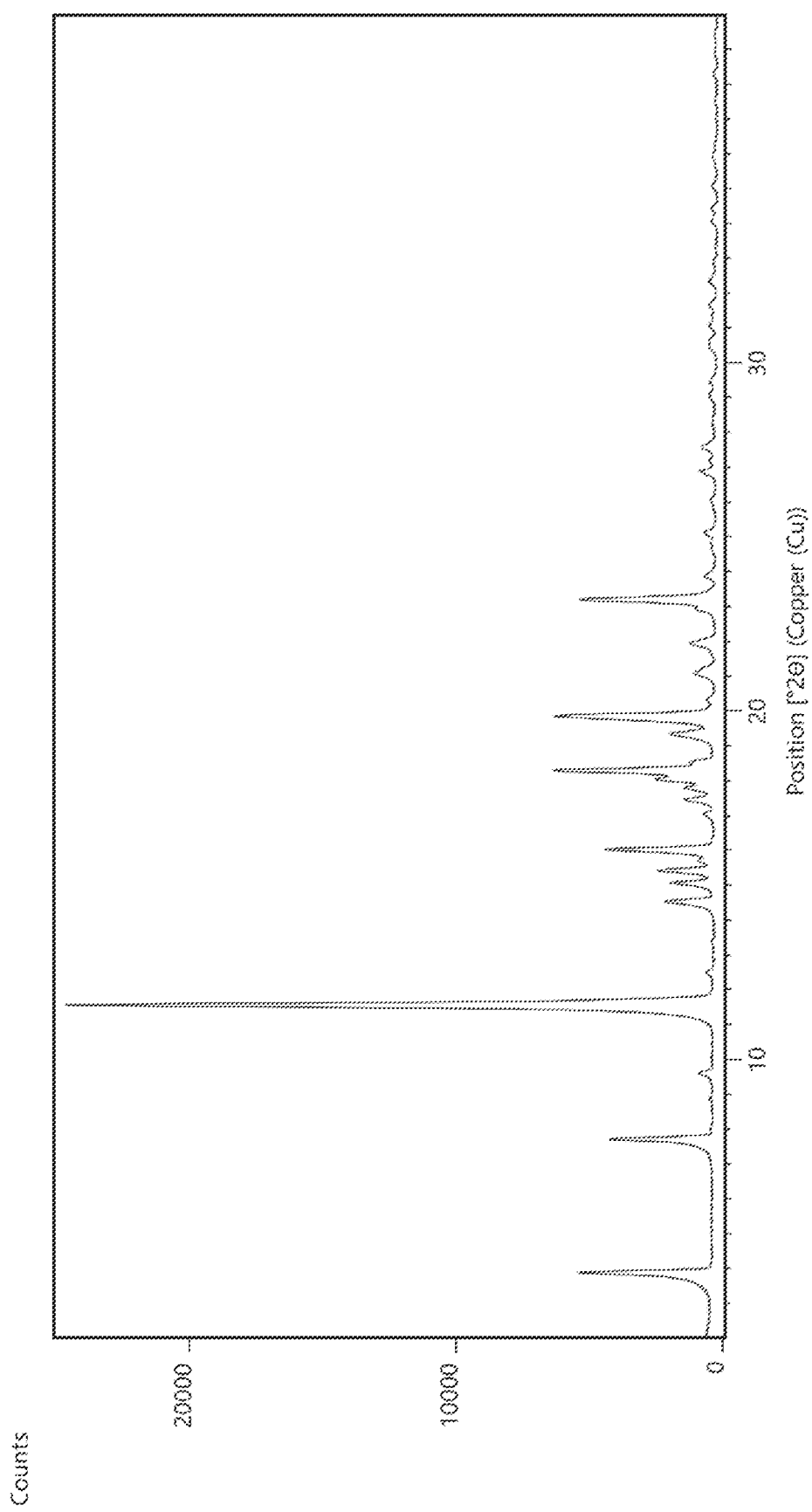
FIG. 4 shows an XRPD trace of the Form B Tris salt of Compound 1.

In some embodiments, the crystalline salt form is characterized by data comprising one, two, three or more XRPD signals, in terms of 2θ, where the XRPD signals are selected from those Form A signals in Table 4 having at least one corresponding Form B signal, ±0.2°, in Table 5. In some embodiments, the crystalline salt form comprises an XRPD profile substantially as shown in FIG. 1. In some embodiments, the crystalline salt form comprises an XRPD profile substantially as shown in FIG. 4. In some embodiments, the crystalline salt form comprises at least 50% of the XRPD signals in Table 4, in terms of 2θ, ±0.2°. In some embodiments, the crystalline salt form comprises at least 50% of the XRPD signals in Table 5, in terms of 2θ, ±0.2°.

In some embodiments, a composition provided herein includes a mixture of salt Form A and salt Form B. In some embodiments, the composition comprises a plurality of polymorphs of the Tris salt form of Compound 1, which plurality of polymorphs optionally comprise at least, or greater than, 80, 90, 95, 99, 99.5, or 99.9 mass % of Form A. In some embodiments, the composition comprises a plurality of polymorphs of the Tris salt form of Compound 1, which plurality of polymorphs optionally comprise at least, or greater than, 80, 90, 95, 99, 99.5, or 99.9 mass % of Form B.

The Tris salt of Compound 1 described herein may also be prepared as an isotopically-labeled compound wherein one or more atoms is replaced by an atom having the same atomic number, but an atomic mass or mass number different from the atomic mass or mass number predominantly found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In some embodiments, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$ $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In some embodiments, the solid forms provided herein are prepared as particles or as a compressed solid. In some embodiments, these solid forms are coated. In some embodiments, the particles comprise a mean particle size of about 10 microns or less. In some embodiments, the particles comprise a mean particle size of about 2 microns or less. In some embodiments, the particles comprise a mean particle size of about 10-20 microns or more. In some embodiments, the solid forms or particles provided herein are formulated as a suspension in liquid or as a dry powder for aerosol administration.

In some embodiments, the solid form is about, or at least about, 75, 80, 85, 90, 95, or 100% by mass of the particle.

In some embodiments, the particle comprises a particle surface wherein the particle surface comprises a coating on at least a portion of the particle surface. In some embodiments, the coating comprises a film coating. In some embodiments, the particle comprises a film coating with a polymer or co-polymer to form microcapsules, which may be used to form chewable taste-masked granules. In some embodiments, the coating comprises a polymer or co-polymer. In some embodiments, the coating comprises one or more of cellulose acetate phthalate, cellulose acetate trimellate, ethyl cellulose, glycol, hydroxy propyl cellulose, hydroxy propyl methyl cellulose, hydroxy propyl methyl cellulose phthalate, methacrylic acid co-polymer, high molecular weight polyethylene, polyvinyl alcohol, polyvinyl pyrrolidone, starch, or shellac. In some embodiments, the coating comprises a sugar. In some embodiments, the coating comprises a sugar coating. In some embodiments, the particles described herein are sugar coated. In some embodiments, the particles described herein are not sugar coated. In some embodiments, the coating comprises an enteric coating. In some embodiments, the coating is an extended release coating. In some embodiments, the coating is a sustained release coating. In some embodiments, the coating comprises a controlled release coating. In some embodiments, the coating is a delayed release coating. In some embodiments, the particles described herein may include a second coating layered atop a first coating. In some embodiments, the coating is stable below about pH 7. In some embodiments, the coating is stable below about pH 5.5. In some embodiments, the coating is stable in an acidic environment. In some embodiments, the coating is stable in gastric fluid and unstable in intestinal fluid.

In some embodiments, a dosage form comprising a plurality of particles comprises coated particles wherein the coating is selected, independently for each particle, from a coating described herein. Accordingly, in some embodiments a plurality of particles may include a mixture of enteric coated particles and extended release coated particles.

In some embodiments, the particles described herein are encapsulated within a coating.

In some embodiments of the particles described herein, the coating is 25% or less by mass of the coated particle.

In some embodiments, the particles described herein are provided as a composition, comprising a plurality of particles, which may include one or more carriers. In some embodiments, the plurality of particles is encapsulated in a capsule, a compression coating, a film coating, or a powder coating. In some embodiments, the particles or plurality of particles, whether as a powder, compressed powder, or tablet, are spray coated. In some embodiments, the plurality of particles is a loose powder within an ingestible capsule. In some embodiments, the plurality of particles is compressed into a friable solid.

In some embodiments, provided herein are dosage forms, comprising a particle, a composition, or a pharmaceutical composition described herein. In some embodiments, the dosage form comprises a plurality of the particles as a powder or as a compressed powder. In some embodiments, the dosage form comprises a plurality of the particles in a liquid suspension. As described above, the particles may be coated.

In some embodiments, the solid forms, particles, compositions, or pharmaceutical compositions described herein are housed in at least one container.

Compositions

In some embodiments, provided herein are compositions, comprising a Tris salt form of Compound 1 described herein.

In some embodiments, provided herein are pharmaceutical compositions, comprising a Tris salt form of Compound 1 described herein and a pharmaceutically acceptable carrier.

In some embodiments of the compositions provided herein, the composition further comprises thyroid hormone. In some embodiments of the compositions provided herein, the composition further comprises a therapeutically effective amount of thyroid hormone.

In some embodiments of the compositions provided herein, the composition further comprises a neurotrophic factor. In some embodiments of the compositions provided herein, the composition further comprises a therapeutically effective amount of a neurotrophic factor.

In some embodiments, the neurotrophic factor is a GLP agonist, BDNF, GDNF, NGF, NT-3, bFGF, CNTF, NT-4/5, IGF, or insulin, or a mimetic thereof, or a combination of two or more thereof. In some embodiments, the GLP agonist is, independently, selected from semaglutide, dulaglutide, exenatide, liraglutide, or lixisenatide.

Methods

In some embodiments, provided herein are methods of treating a disease in a subject in need thereof, comprising administering to the subject a therapeutically effective amount of a compound described herein. In some embodiments, the disease is an RXR-related disease. RXRs effect a diversity of cellular processes, including cellular proliferation, the immune response, lipid and glucose metabolism, and neurological disorders. In some embodiments, the disease comprises neurodegeneration. In some embodiments the neurodegeneration comprises age-related neurodegeneration. In some embodiments, the disease comprises hypoxic brain injury, a retinopathy, glaucoma, type II diabetes mellitus, Huntington's disease, migrane headache, chronic pain, or alopecia areata.

In some embodiments, provided herein are methods of promoting hair growth in a subject in need thereof, comprising administering to the subject a therapeutically effective amount of a compound described herein.

In some embodiments, the subject comprises a refractory disease. In some embodiments, the refractory disease comprises a refractory cancer.

In some embodiments, the refractory disease comprises a thyroid hormone-resistant disease.

In some embodiments, the refractory disease comprises neurotrophic factor-resistant disease.

In some embodiments of the methods provided herein, the methods further comprise administering a therapeutically effective amount of thyroid hormone.

In some embodiments of the methods provided herein, the methods further comprise administering a therapeutically effective amount of a neurotrophic factor.

In some embodiments, the neurotrophic factor is a GLP agonist, BDNF, GDNF, NGF, NT-3, bFGF, CNTF, NT-4/5, IGF, or insulin, or a mimetic thereof, or a combination of two or more thereof. In some embodiments, the neurotrophic factor is GDNF, or a GDNF mimetic, and the CNS disease is Parkinson's disease. In some embodiments, the neurotrophic factor is GDNF, or a GDNF mimetic, and the CNS disease is multiple sclerosis. In some embodiments, the neurotrophic factor is GDNF, or a GDNF mimetic, and the CNS disease is amyotrophic lateral sclerosis. In some embodiments, the neurotrophic factor is GDNF, or a GDNF mimetic, and the CNS disease is Alzheimer's disease. In some embodiments, the neurotrophic factor is BDNF and the CNS disease is Alzheimer's disease. In some embodiments, the neurotrophic factor is insulin or insulin-like growth factor, and the CNS disease is Alzheimer's disease. In some embodiments, the neurotrophic factor is BDNF and the CNS disease is multiple sclerosis. In some embodiments, the neurotrophic factor is BDNF, and the CNS disease is stroke, nervous system trauma, aging, or dementia. In some embodiments, the neurotrophic factor is BDNF, or GDNF, or insulin, or a mimetic thereof, or a combination of two or more thereof, and the CNS disease is aging-related CNS neurodegeneration. In some embodiments, the neurotrophic factor is IGF, or a mimetic thereof, and the CNS disease is Parkinson's Disease, or Alzheimer's disease, or amyotrophic lateral sclerosis, or multiple sclerosis, or aging-related neurodegeneration. In some embodiments, the neurotrophic factor or mimetic is administered by oral, parenteral, nasal, or topical routes, or by controlled release.

In some embodiments of the methods provided herein, the disease is selected from a nervous system disorder, a muscular disorder, a cellular proliferation disorder (e.g. cancer or tumor), or an autoimmune disorder. In some embodiments, the cancer is a non-solid cancer (e.g., a liquid cancer, e.g., a blood cancer). In some embodiments, the cancer or tumor is a solid cancer or tumor.

In some embodiments, the nervous system disorder is a central nervous system disorder, such as relapsing/remitting, primary progressive, and secondary progressive forms of multiple sclerosis (MS), diffuse white matter injury in pre-term infants, neuromyelitis optica, acute disseminated encephalomyelitis, Marburg multiple sclerosis, diffuse myelinoclastic sclerosis (Schilder's disease), Balo concentric sclerosis, solitary sclerosis, optic neuritis, transverse myelitis, amyotrophic lateral sclerosis (ALS), leukodystrophy (multiple variants, e.g. adrenoleukodystrophy, adrenomyeloneuropathy), Parkinson's disease, Alzheimer's disease, progressive supranuclear palsy, stroke, seizure disorders, CNS trauma including traumatic brain injury and traumatic spinal cord injury, radiation induced neuroinflammation, radiation somnolence syndrome, Devic's disease, inflammatory demyelinating diseases, CNS neuropathies, central pontine myelinolysis, Tabes dorsalis (syphilitic myelopathy), progressive multifocal leukoencephalopathy, leukodystrophy, depression, schizophrenia, epilepsy, dementias, and cachexia related to cancer, AIDS, chronic kidney disease, and advanced age.

In some embodiments, the central nervous system disorder is a demyelination-related disorder such as multiple sclerosis, radiation-induced central nervous system inflammation, Alzheimer's disease or Parkinson's disease.

In some embodiments, the nervous system disorder is a peripheral nervous system disorder such as Guillain-Barré Syndrome, acute inflammatory demyelinating polyneuropathy, chronic inflammatory demyelinating polyneuropathy, demyelinating diabetic neuropathy, progressive inflammatory neuropathy, drug- or toxin-induced neuropathy, such as chemotherapy-induced neuropathy or organophosphate-induced neuropathy, anti-MAG peripheral neuropathy, Charcot-Marie-Tooth Disease, or copper deficiency.

In some embodiments, the muscle disorder is a muscle wasting disorder. In some embodiments, the muscle disorder is selected from acid maltase deficiency, atony, atrophy, ataxia, Becker Muscular Dystrophy (BMD), cardiac muscle ischemia, cardiac muscle infarction, a cardiomyopathy, carnitine deficiency, carnitine palmitoyltransferase deficiency, Central Core Disease (CCD), centronuclear (myotubular) myopathy, cerebral palsy, compartment syndromes, channelopathies, Congenital Muscular Dystrophy (CMD), corticosteroid myopathy, cramps, dermatomyositis, distal muscular dystrophy, Duchenne Muscular Dystrophy (DMD), dystrophinopathies, Emery-Dreifuss Muscular Dystrophy (EDMD), Facioscapulohumeral Muscular Dystrophy (FSHD), fibromyalgia, fibrositis, Limb Girdle Muscular Dystrophy (LGMD), McArdle syndrome, muscular dystrophy, muscle fatigue, myasthenia gravis, myofascial pain syndrome, myopathy, myotonia, Myotonic Muscular Dystrophy type 1, Myotonic Muscular Dystrophy type 2, Nemaline myopathy, Oculopharyngeal Muscular Dystrophy (OCM), myoglobinuria, paramyotonia congenita (Eulenberg's disease), polymyositis, rhabdomyolysis, sarcoglycanopathies, or spasms.

In some embodiments, the muscular disorder is a myopathy such as dermatomyositis, inclusion body myositis, or polymyositis.

In some embodiments, the muscular disorder is due to cancers, HIV/AIDS, COPD, chronic steroid use, fibromyalgia, or skeletal muscle myopathies.

In certain embodiments for treating an autoimmune disorder, the methods treats an autoimmune disease selected from the group consisting of acute disseminated encephalomyelitis (ADEM), Addison's disease, an allergy, allergic rhinitis, anti-phospholipid antibody syndrome (APS), an arthritis, asthma, acquired immunodeficiency syndrome (AIDS), autoimmune hemolytic anemia, autoimmune hepatitis, autoimmune inner ear disease, bullous pemphigoid, celiac disease, Chagas disease, chronic obstructive pulmonary disease (COPD), diabetes mellitus type 1 (IDDM), endometriosis, a gastrointestinal disorder, a glomerulonephritis, Goodpasture's syndrome, Graves' disease, Guillain-Barré syndrome (GBS), Hashimoto's thyroiditis, hidradenitis suppurativa, idiopathic thrombocytopenic purpura, interstitial nephritis, interstitial cystitis, a lupus, morphea, multiple sclerosis (MS), myasthenia gravis, a myopathy, myositis, narcolepsy, neuromyotonia, pemphigus vulgaris, pernicious anaemia, primary biliary cirrhosis, psoriasis, psoriatic arthritis, a pulmonary fibrosis, recurrent disseminated encephalomyelitis, rheumatic fever, schizophrenia, scleroderma, Sjögren's syndrome, a skin disorder, tenosynovitis, uveitis, a vasculitis, or vitiligo.

In certain embodiments, the disease does not include multiple sclerosis, i.e. the subject receiving treatment does not have, or has not been diagnosed with, multiple sclerosis.

In certain embodiments, the arthritis is monoarthritis, oligoarthritis, polyarthritis, osteoarthritis, rheumatoid arthritis, juvenile idiopathic arthritis, septic arthritis, spondyloarthropathy, gout, pseudogout, or Still's disease.

In some embodiments, the gastrointestinal disorder is an irritable bowel disease or an inflammatory bowel disease. In other embodiments, the inflammatory bowel disease is Crohn's disease or ulcerative colitis.

In some embodiments, the lupus is discoid lupus erythematosus, drug-induced lupus erythematosus, lupus nephritis, neonatal lupus, subacute cutaneous lupus erythematosus, or systemic lupus erythematosus.

In some embodiments, the autoimmune disorder is a myopathy with an autoimmune component such as dermatomyositis, inclusion body myositis, or polymyositis.

In some embodiments, the skin disorder is dermatitis, eczema, statis dermatitis, hidradenitis suppurativa, psoriasis, rosacea, or scleroderma.

In some embodiments, the vasculitis is Buerger's disease, cerebral vasculitis, Churg-Strauss arteritis, cryoglobulinemia, essential cryoglobulinemic vasculitis, giant cell arteritis, Golfer's vasculitis, Henoch-Schonlein purpura, hypersensitivity vasculitis, Kawasaki disease, microscopic polyarteritis/polyangiitis, polyarteritis nodosa, polymyalgia rheumatica (PMR), rheumatoid vasculitis, Takayasu arteritis, or Wegener's granulomatosis.

In some embodiments, the autoimmune disease is multiple sclerosis, psoriasis, rheumatoid arthritis, glomerulonephritis, pulmonary fibrosis, interstitial nephritis, or an inflammatory bowel disease.

While the methods as described refer to the compounds described herein, it is to be understood that the compounds may be used in conjunction with these methods in the form of a composition or a pharmaceutical composition as well.

Actual dosage levels of the active ingredients (e.g. the compounds of the formulae provided herein), the compositions, or the pharmaceutical compositions provided herein may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health, and prior medical history of the patient being treated, and like factors well-known in the medical arts. A medical doctor, e.g., physician or veterinarian, having ordinary skill in the art may readily determine and prescribe the effective amount of the pharmaceutical composition required. For example, the physician or veterinarian could start doses of the compounds employed in the pharmaceutical composition at levels lower than that required in order to achieve the desired therapeutic effect and gradually increase the dosage until the desired effect is achieved.

Administration of a compound, a composition, or a combination disclosed herein includes a variety of enteral or parenteral approaches selected from, without limitation: oral administration in any acceptable form, such as, e.g., tablet, liquid, capsule, powder, or the like; topical administration in any acceptable form, such as, e.g., drops, spray, creams, gels or ointments; buccal, nasal, and/or inhalation administration in any acceptable form; rectal administration in any acceptable form; vaginal administration in any acceptable form; intravascular administration in any acceptable form, such as, e.g., intravenous bolus injection, intravenous infusion, intra-arterial bolus injection, intra-arterial infusion and catheter instillation into the vasculature; peri- and intra-tissue administration in any acceptable form, such as, e.g., intraperitoneal injection, intramuscular injection, subcutaneous injection, subcutaneous infusion, intraocular injection, retinal injection, or sub-retinal injection or epidural injection; intravesicular administration in any acceptable form, such as, e.g., catheter instillation; and by placement device, such as, e.g., an implant, a stent, a patch, a pellet, a catheter, an osmotic pump, a suppository, a bioerodible delivery system, a non-bioerodible delivery system or another implanted extended or slow release system.

A compound, a composition, or a combination disclosed herein can be administered to a mammal using a variety of routes. Routes of administration of include, without limitation, oral, nasal, rectal, intravaginal, parenteral, buccal, sublingual, or topical. In some embodiments, the oral or nasal route of administration is an oral inhalational or nasal inhalational route of administration. The compounds for use as described herein may be formulated for administration by any suitable route to achieve the particular method being applied. In some embodiments, routes of administration suitable for treating a demyelination-related disorder as disclosed herein include both local and systemic administration. Local administration results in significantly more delivery of a compound, a composition, or a combination to a specific location as compared to the entire body of the mammal, whereas, systemic administration results in delivery of a compound, a composition, or a combination to essentially the entire body of the individual. Routes of administration suitable for or treating a demyelination-related disorder as disclosed herein also include both central and peripheral administration. Central administration results in delivery of a compound, a composition, or a combination to essentially the central nervous system of the individual and includes, e.g., nasal administration, intrathecal administration, epidural administration as well as a cranial injection or implant. In some embodiments, central administration is used to administer the compound, composition, or combinations described herein.

Central administration by the nasal route, which targets drug absorption through the vascular plexus of the nasal cavity, is distinct from administration by nasal inhalation, which delivers drug through the pulmonary system. Whereas the latter typically uses liquid or dry powder aerosols with mean particle sizes less than 10 microns, and in some embodiments around 2 microns or less, central administration is typically accomplished using mean particle sizes of 10-20 microns or larger. Mists and aerosols can be generated using nebulizers, dry powder inhalers, pressurized aerosols, and atomization pumps, the latter being preferred. It is also feasible to use nose drops for central administration by the nasal route.

Peripheral administration results in delivery of a compound, a composition, or a combination to essentially any area of an individual outside of the central nervous system and encompasses any route of administration other than direct administration to the spine or brain. The actual route of administration of a compound, a composition, or a combination disclosed herein used can be determined by a person of ordinary skill in the art by taking into account factors, including, without limitation, the type of demyelination-related disorder, the location of the demyelination-related disorder, the cause of the demyelination-related disorder, the severity of the demyelination-related disorder, the duration of treatment desired, the degree of relief desired, the duration of relief desired, the particular compound, composition, or combination, the rate of excretion of the compound, composition, or combination used, the pharmacodynamics of the compound, composition, or combination used, the nature of the other compounds to be included in the composition or combination, the particular route of administration, the particular characteristics, history and risk factors of the individual, such as, e.g., age, weight, general health and the like, the response of the individual to the treatment, or any combination thereof. An effective dosage amount of a compound, a composition, or a combination disclosed herein can thus readily be determined by the person of ordinary skill in the art considering all criteria and utilizing his best judgment on the individual's behalf.

In some embodiments, provided herein are packaged compounds, packaged compositions, or packaged pharmaceutical compositions, comprising a container holding a therapeutically effective amount of a compound described herein, and instructions for using the compound in accordance with one or more of the methods provided herein.

The present compounds and associated materials can be finished as a commercial product by the usual steps performed in the present field, for example by appropriate sterilization and packaging steps. For example, the material can be treated by UV/vis irradiation (200-500 nm), for example using photo-initiators with different absorption wavelengths (e.g. Irgacure 184, 2959), preferably water-soluble initiators (e.g. Irgacure 2959). Such irradiation is usually performed for an irradiation time of 1-60 min, but longer irradiation times may be applied, depending on the specific method. The material according to the present disclosure can be finally sterile-wrapped so as to retain sterility until use and packaged (e.g. by the addition of specific product information leaflets) into suitable containers (boxes, etc.).

According to further embodiments, the present compounds can also be provided in kit form combined with other components necessary for administration of the material to the patient. For example, disclosed kits, such as for use in the treatment of cancer, can further comprise, for example, administration materials.

The kits are designed in various forms based on the specific deficiencies they are designed to treat.

The compounds or compositions provided herein may be prepared and placed in a container for storage at ambient or elevated temperature. When the compound or composition is stored in a polyolefin plastic container as compared to a polyvinyl chloride plastic container, discoloration of the compound or composition may be reduced, whether dissolved or suspended in a liquid composition (e.g., an aqueous or organic liquid solution), or as a solid. Without wishing to be bound by theory, the container may reduce exposure of the container's contents to electromagnetic radiation, whether visible light (e.g., having a wavelength of about 380-780 nm) or ultraviolet (UV) light (e.g., having a wavelength of about 190-320 nm (UV B light) or about 320-380 nm (UV A light)). Some containers also include the capacity to reduce exposure of the container's contents to infrared light, or a second component with such a capacity. The containers that may be used include those made from a polyolefin such as polyethylene, polypropylene, polyethylene terephthalate, polycarbonate, polymethylpentene, polybutene, or a combination thereof, especially polyethylene, polypropylene, or a combination thereof. IN some embodiments, the container is a glass container. The container may further be disposed within a second container, for example, a paper, cardboard, paperboard, metallic film, or foil, or a combination thereof, container to further reduce exposure of the container's contents to UV, visible, or infrared light. Compounds and compositions benefiting from reduced discoloration, decomposition, or both during storage, include eye drop solutions or implants that include a compound or composition thereof provided herein. The compounds or compositions provided herein may need storage lasting up to, or longer than, three months; in some cases up to, or longer than one year. The containers may be in any form suitable to contain the contents; for example, a bag, a bottle, or a box.

The following examples further illustrate aspects of the present disclosure. However, they are in no way a limitation of the teachings or disclosure as described herein.

EXAMPLES

Salts of Compound 1 were isolated. For example, about 50 mg starting free acid (Compound 1) and the corresponding base are mixed in about 0.06-8.0 mL solvent system with a molar charge ratio of 1:1 (except Ca and Mg wherein a molar ratio of 2:1 was used). After magnetically stirring for 4 days at RT, any precipitation is isolated by centrifugation. If there is no precipitation, the clear solutions are transferred to stir at 5° C. to induce crystallization for 24 h. If still no solid, the final clear solutions are subjected to slow evaporation at RT. Any isolated solids are vacuum dried at 40° C. for 2 hours before analysis. Various isolated salts of Compound 1 were tested for solid-state properties such as solid-state stability, hygroscopicity, crystallinity, form (i.e., anhydrate, hydrate, or solvate), and solubility in artificial gastric and artificial small bowel fluids. The Tris salt of Compound 1 was selected for further analysis, in part, based on the discovery of its improved various solid-state properties relative to Compound 1.

Values in terms of 2θ and ° C. may vary from sample to sample, and from machine to machine. Thus, the values provided herein may include variation, in terms of 2θ, of ±0.2°, and variation, in terms of Centigrade, of ±3° C.

Example 1: Tris salt form crystallization. Table 3 describes a procedure for preparing crystals of Tris salt Form A. The XRPD pattern of the dry product shows that most of the resulting solids are of Form A, but there are Form B signature signals showing up with very low intensity. The DSC curve confirmed the presence of Form B in the product by exhibiting two thermal transitions, one at 149.3° C. (corresponding to Form B from salt screening) and the other at 153.9° C. (corresponding to Form A). Table 3a describes an alternate procedure for preparing crystals of Tris salt Form A.

TABLE 3

Multi-gram scale procedure for Tris salt form A crystallization.
Material and Equipment
API 90 g, Compound 1
Solvents anhydrous 2-BuOH
Crystallizer 1 L Syrris Atlas HD reactor

| Procedure | Comments |
| --- | --- |
| 1 Dissolve API in solvents (200 mg API/mL solvent) at 40° C. | API: 90.26 g |
| 2 Mix ground TRIS base solid (31.04 g) with 300 mL solvent at 25° C. | TRIS base solids grinded manually with mortar and pestle. Slurry with solid size below 200 μm |
| 3 Add 18 mL of the API solution to the above slurry at once | Achieve saturation of TRIS salt in mother liquor |
| 4 Add seeds (dry) and age for about 15 min | 3 wt % (1.08 g) |
| 5 Add API solution to the above slurry at about 1 mL/min | Stirring at 700 rpm, 25° C. |
| 6 Turn on external circulation and in-line IKA milling when the slurry reaches 600 mL volume | Pump: $N_2$ flow powered, 2.5 L/min; IKA mill: filter size: medium, fine, fine from top; 10,000 rpm |
| 7 Turn the IKA mill down to 3,000 rpm at the end of API addition | Keep the circulation running. |
| 8 Age the slurry for 16 h | Keep the circulation running. |
| 9 Cool the batch to 10° C. over 3 h | |
| 10 Filter the batch and displacement wash the cake with 2-BuOH | |
| 11 Dry the washed wet cake at 40° C. with vacuum pull for ~12 hours | Sample for $^1$H NMR, XRPD, DSC, and TGA |

Results

| | | |
| --- | --- | --- |
| Crystal Form by XRPD | | Form A + small amount of Form B |
| Yield | by solids weight | 88.9% |
| | by ML Loss | 93.5% |
| | Theoretical | 90.0% |
| TGA, mass loss up to 100° C. (water content) | | negligible |
| Product purity by HPLC | | 99.6 A % |
| Compound 1:TRIS (mole equivalents) in product by $^1$H NMR | | 1.0:1.0 |

Example 2: Preparation of Form B. Form B may be prepared according to Table 3 wherein the solvent comprises at least 3% water by volume. Form B may also be prepared according to Table 3a.

TABLE 3a

| Salt Form | Procedure |
| --- | --- |
| Form A Tris salt of Compound 1 | 1. Prepare solution A by weighing ~406.5 mg free acid (Compound 1) and dissolve it in 46 mL of Acetonitrile to obtain clear solution.<br>2. Prepare solution B by weighing ~550 mg TRIS and dissolve it in 1 mL water.<br>3. Mix entire solution A and 250 μL of Solution B and stir at RT for 4 days.<br>4. Isolate solids by positive nitrogen flow using 0.22 micron filter and vacuum dry at RT overnight, followed by 2 hour drying at 40° C. |
| Form B Tris salt of Compound 1 | 1. Prepare solution A by weighing ~510.6 mg free acid (Compound 1) and dissolve it in 6.125 mL of IPA to obtain a clear solution.<br>2. Prepare solution B by weighing ~550 mg TRIS and dissolve it in 1 mL water.<br>3. Mix entire solution A and 320 μL of Solution B and stir at RT for 4 days.<br>4. Isolate solids by positive nitrogen flow using 0.22 micron filter and vacuum dry at RT overnight, followed by 2 hour drying at 40° C. |

Example 3: XRPD analysis. A Panalytical Xpert instrument was used having the following parameters: X-Ray tube Cu (Kα); tube voltage 45 kV; tube current 40 mA; scan from 2 to 40 degrees 2θ; 0.01 degrees/step; and a scan rate of 6 degrees/minute. Results are shown in FIG. 1 and FIG. 4.

Table 4 provides a list of signals and relative intensities for the XRPD of the Form A Tris salt of Compound 1. Table 5 provides a list of signals and relative intensities for the XRPD of the Form B Tris salt of Compound 1.

TABLE 4

Observed XRPD signals and relative intensities of Tris Form A.

| Signal No. | Pos. [°2θ] ± 0.2 | Rel. Int. [%] |
| --- | --- | --- |
| 1 | 3.80 | 31.43 |
| 2 | 7.57 | 27.91 |
| 3 | 9.51 | 4.21 |
| 4 | 10.06 | 3.14 |
| 5 | 11.34 | 100.00 |
| 6 | 12.01 | 11.81 |

TABLE 4-continued

Observed XRPD signals and relative intensities of Tris Form A.

| Signal No. | Pos. [°2θ] ± 0.2 | Rel. Int. [%] |
|---|---|---|
| 7 | 14.55 | 5.97 |
| 8 | 14.68 | 6.93 |
| 9 | 15.12 | 16.12 |
| 10 | 15.51 | 12.13 |
| 11 | 16.20 | 3.34 |
| 12 | 17.29 | 12.34 |
| 13 | 17.60 | 13.07 |
| 14 | 18.10 | 20.4 |
| 15 | 18.67 | 12.49 |
| 16 | 19.03 | 3.8 |
| 17 | 19.63 | 28.75 |
| 18 | 20.16 | 8.78 |
| 19 | 20.62 | 1.79 |
| 20 | 20.94 | 2.7 |
| 21 | 21.11 | 6.32 |
| 22 | 21.73 | 0.83 |
| 23 | 22.35 | 0.75 |
| 24 | 22.74 | 11.23 |
| 25 | 23.73 | 5 |
| 26 | 23.97 | 1.7 |
| 27 | 24.26 | 2.98 |
| 28 | 24.61 | 3.52 |
| 29 | 25.53 | 1.86 |
| 30 | 26.46 | 0.14 |

TABLE 5

Observed XRPD signals and relative intensities of Tris Form B.

| Signal No. | Pos. [°2θ] ± 0.2 | Rel. Int. [%] |
|---|---|---|
| 1 | 3.89 | 19.49 |
| 2 | 7.69 | 15.95 |
| 3 | 9.59 | 2.18 |
| 4 | 11.54 | 100.00 |
| 5 | 12.52 | 1.11 |
| 6 | 14.53 | 7.41 |
| 7 | 15.07 | 6.44 |
| 8 | 15.40 | 8.61 |
| 9 | 15.68 | 2.36 |
| 10 | 16.03 | 16.04 |
| 11 | 17.04 | 1.58 |
| 12 | 17.45 | 4.64 |
| 13 | 17.79 | 4.35 |
| 14 | 18.02 | 9.13 |
| 15 | 18.30 | 24.33 |
| 16 | 18.52 | 3.87 |
| 17 | 19.36 | 6.53 |
| 18 | 19.85 | 24.48 |
| 19 | 20.32 | 1.18 |
| 20 | 21.06 | 3.16 |
| 21 | 21.22 | 1.95 |
| 22 | 21.94 | 3.85 |
| 23 | 22.90 | 3.00 |
| 24 | 23.21 | 20.62 |
| 25 | 23.88 | 1.74 |
| 26 | 24.83 | 0.70 |
| 27 | 25.06 | 1.50 |
| 28 | 26.04 | 0.71 |
| 29 | 26.87 | 2.49 |
| 30 | 27.16 | 0.81 |

Figure 2:
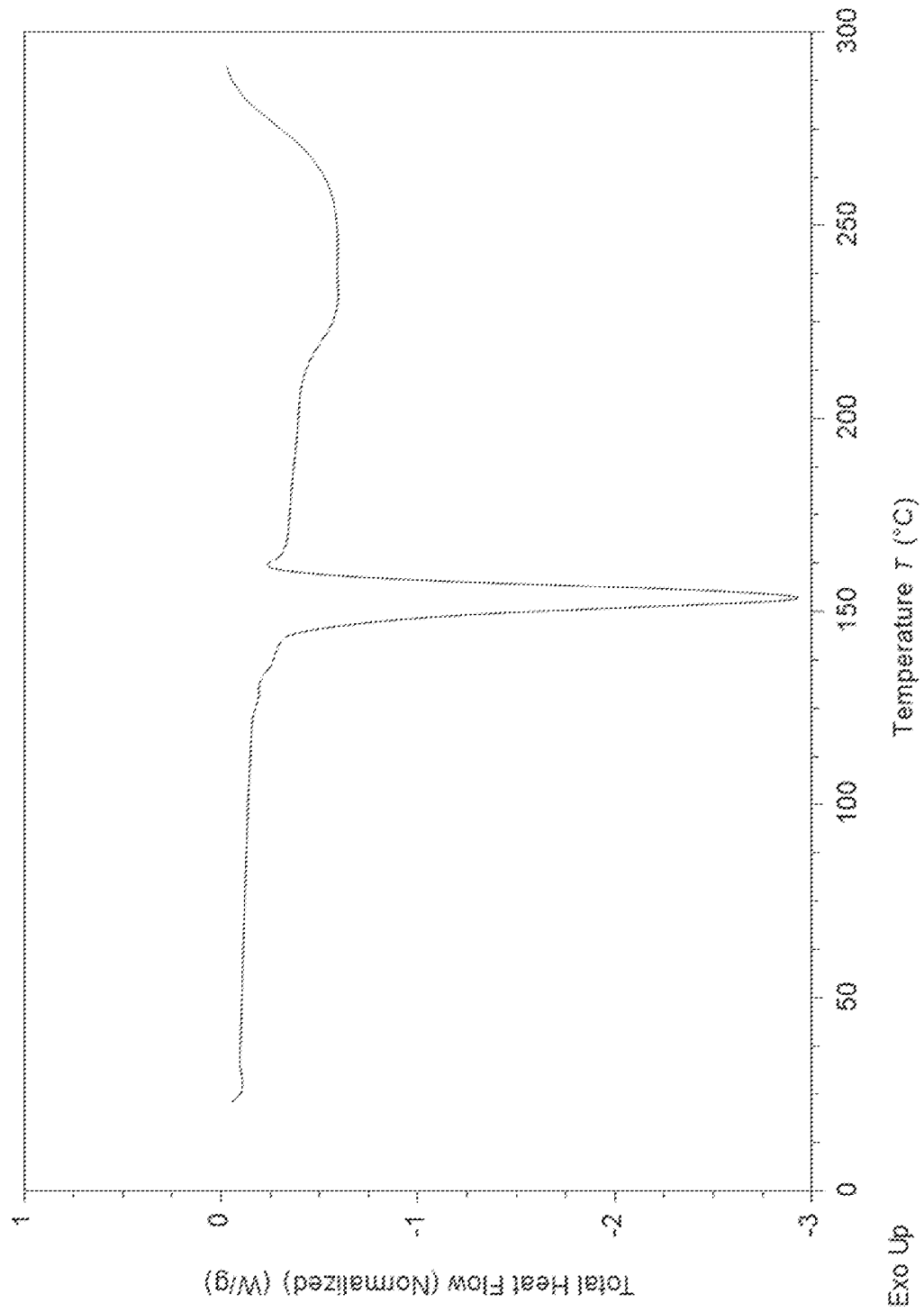
FIG. 2 shows a differential scanning calorimetry (DSC) trace of the Form A Tris salt of Compound 1.
Figure 5:
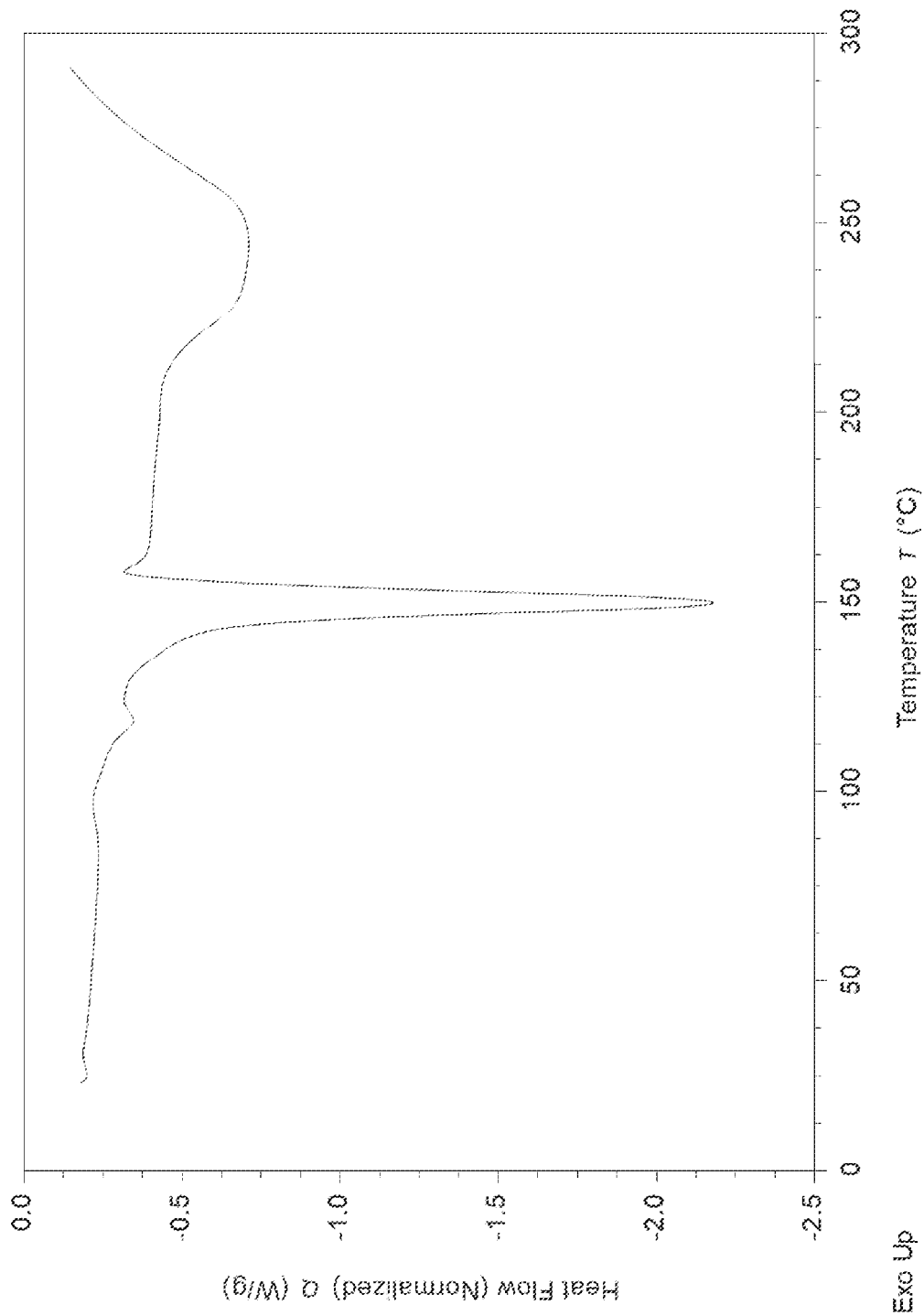
FIG. 5 shows a DSC trace of the Form B Tris salt of Compound 1.

Example 4: Differential scanning calorimetry analysis. A TA Instruments Discovery DSC (DSC-1) instrument was used having the following parameters: ramp 3° C./minute; scan from 25 to 250° C.; and a 50 mL/minute $N_2$ sweep. Results are shown in FIG. 2 and FIG. 5.

Table 6 provides a DSC endothermic transition temperature of the Form A Tris salt of Compound 1 and the Form B Tris salt of Compound 1.

TABLE 6

Observed DSC thermogram endothermic transition temperatures.

| Compound | Temperature (° C.) ± 3 |
|---|---|
| Form A Tris salt of Compound 1 | 153.50 |
| Form B Tris salt of Compound 1 | 149.67 |

Figure 6:
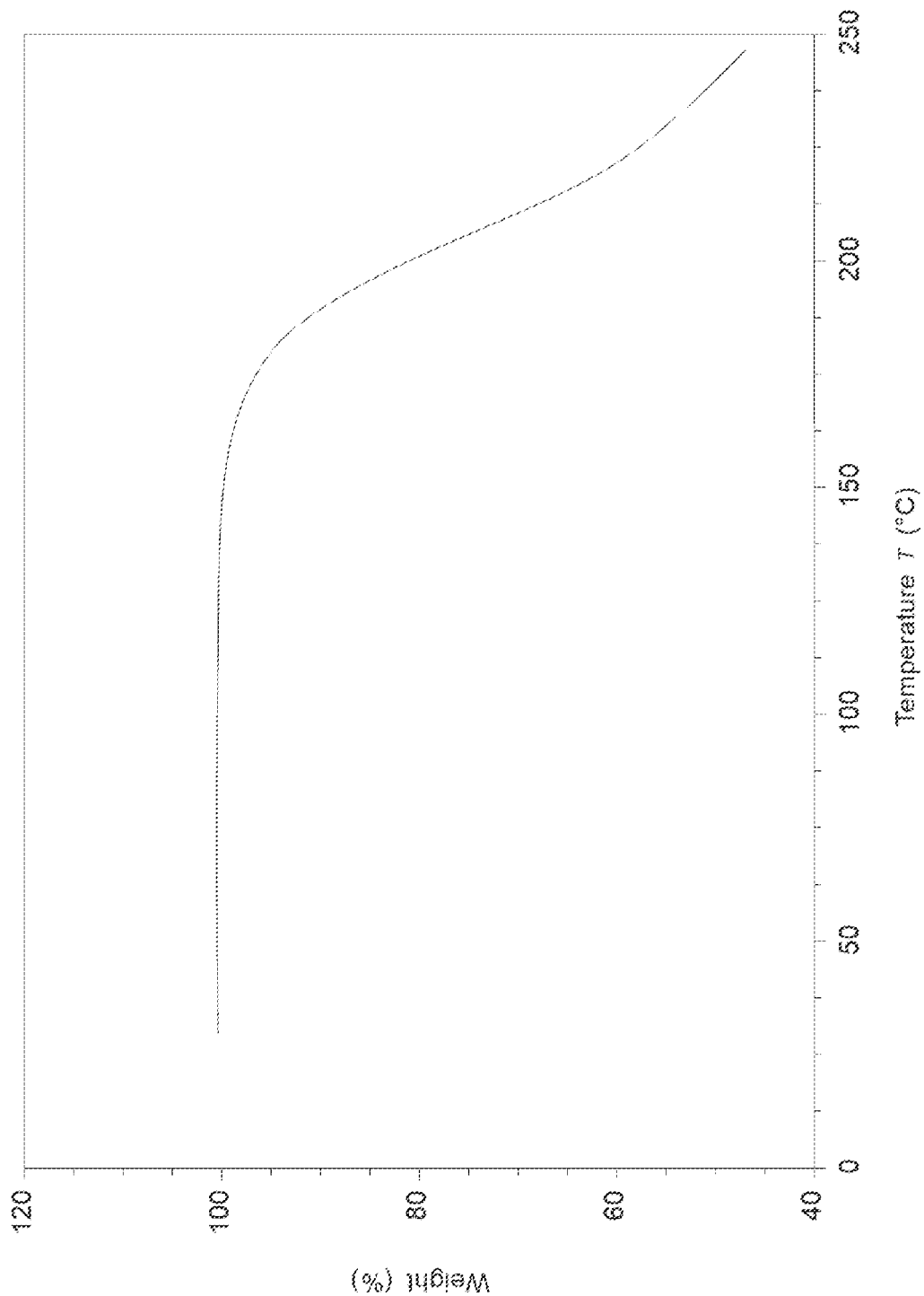
FIG. 6 shows a TGA trace of the Form B Tris salt of Compound 1.
Figure 7:
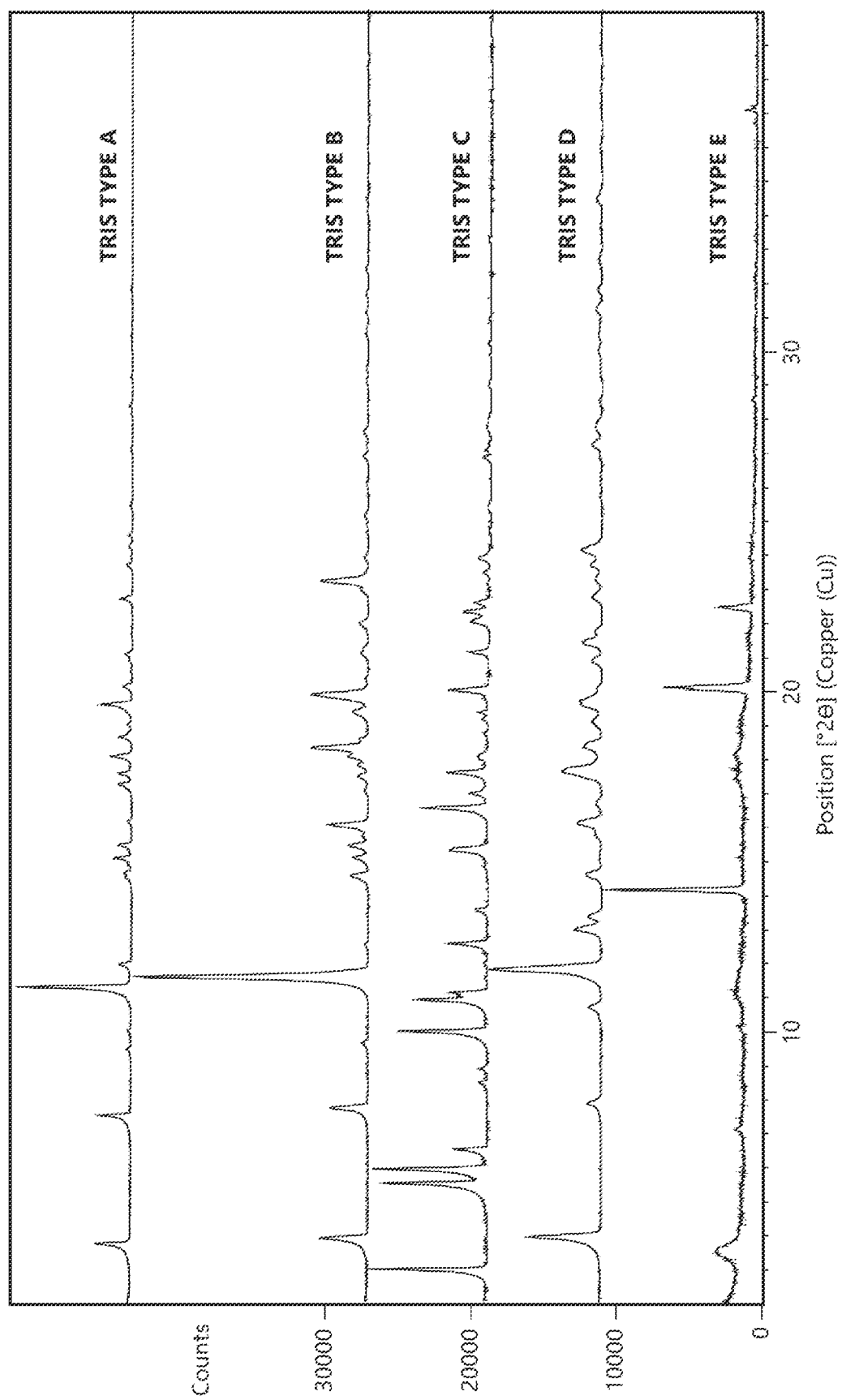
FIG. 7 shows XRPD traces of the Form A/B/C/D/E Tris salts of Compound 1.
Figure 8A:
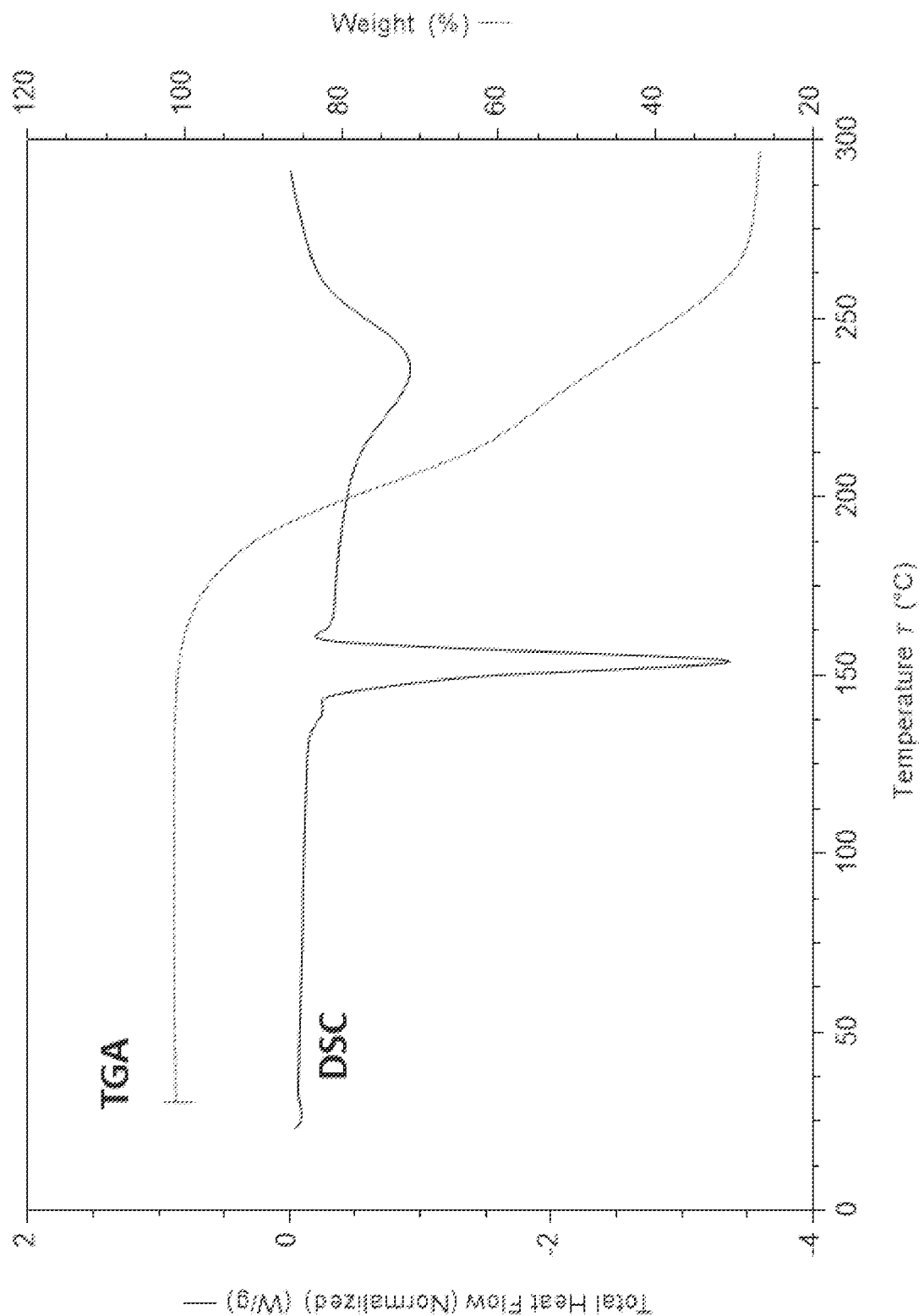
FIG. 8A shows DSC/TGA traces of the Form A Tris salt of Compound 1.
Figure 8B:
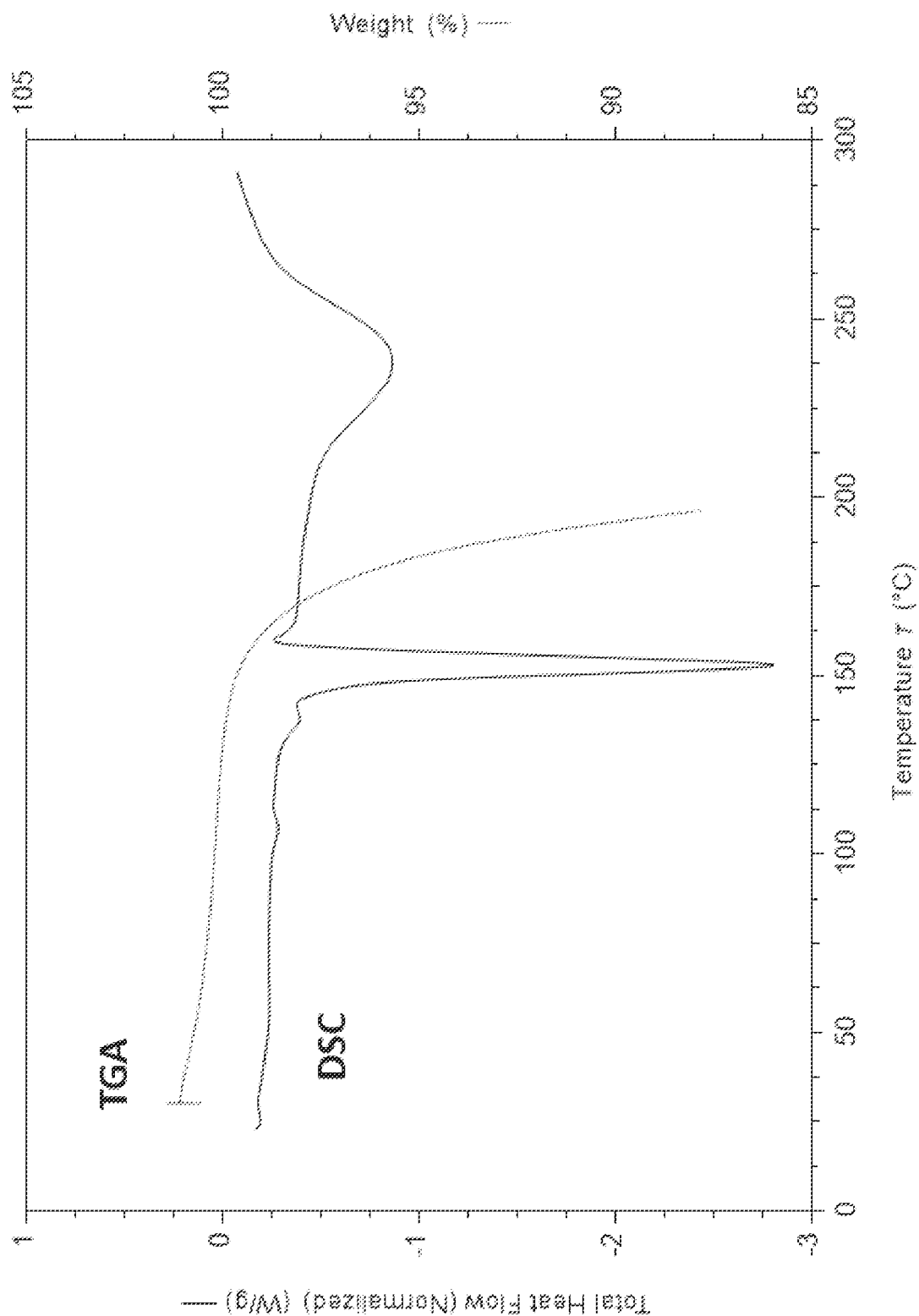
FIG. 8B shows DSC/TGA traces of the Form B Tris salt of Compound 1.
Figure 8C:
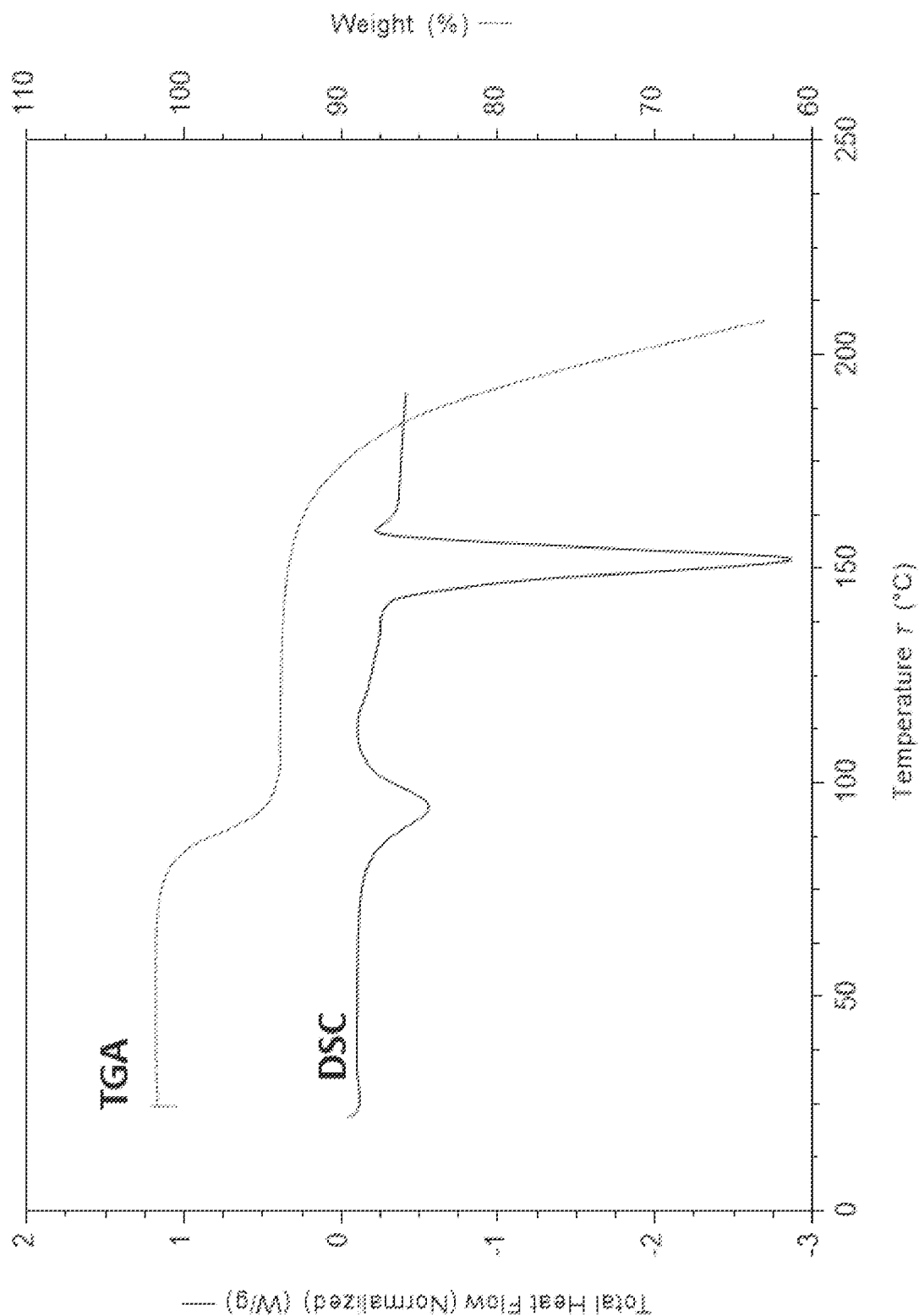
FIG. 8C shows DSC/TGA traces of the Form C Tris salt of Compound 1.
Figure 8D:
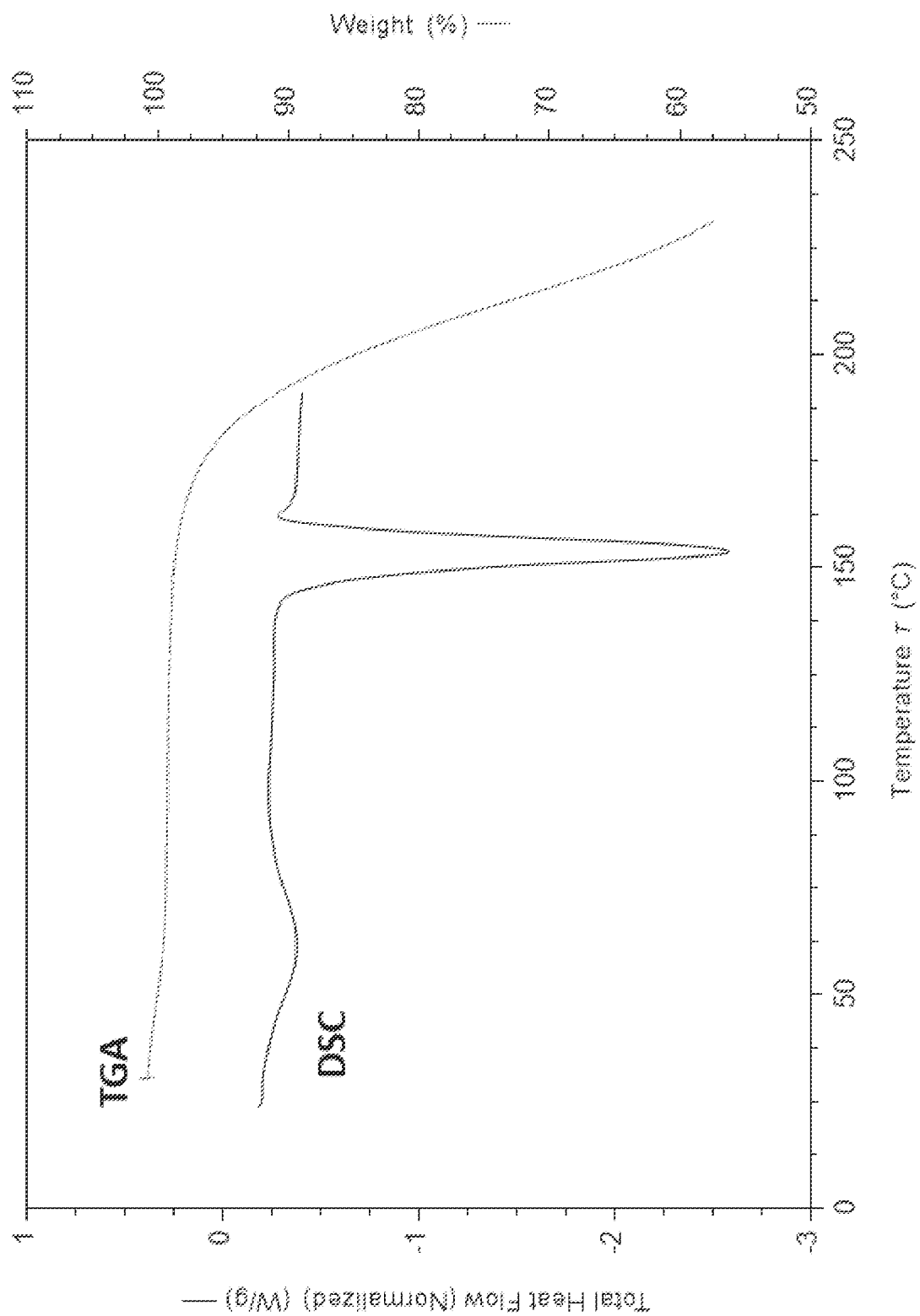
FIG. 8D shows DSC/TGA traces of the Form D Tris salt of Compound 1.
Figure 9A:
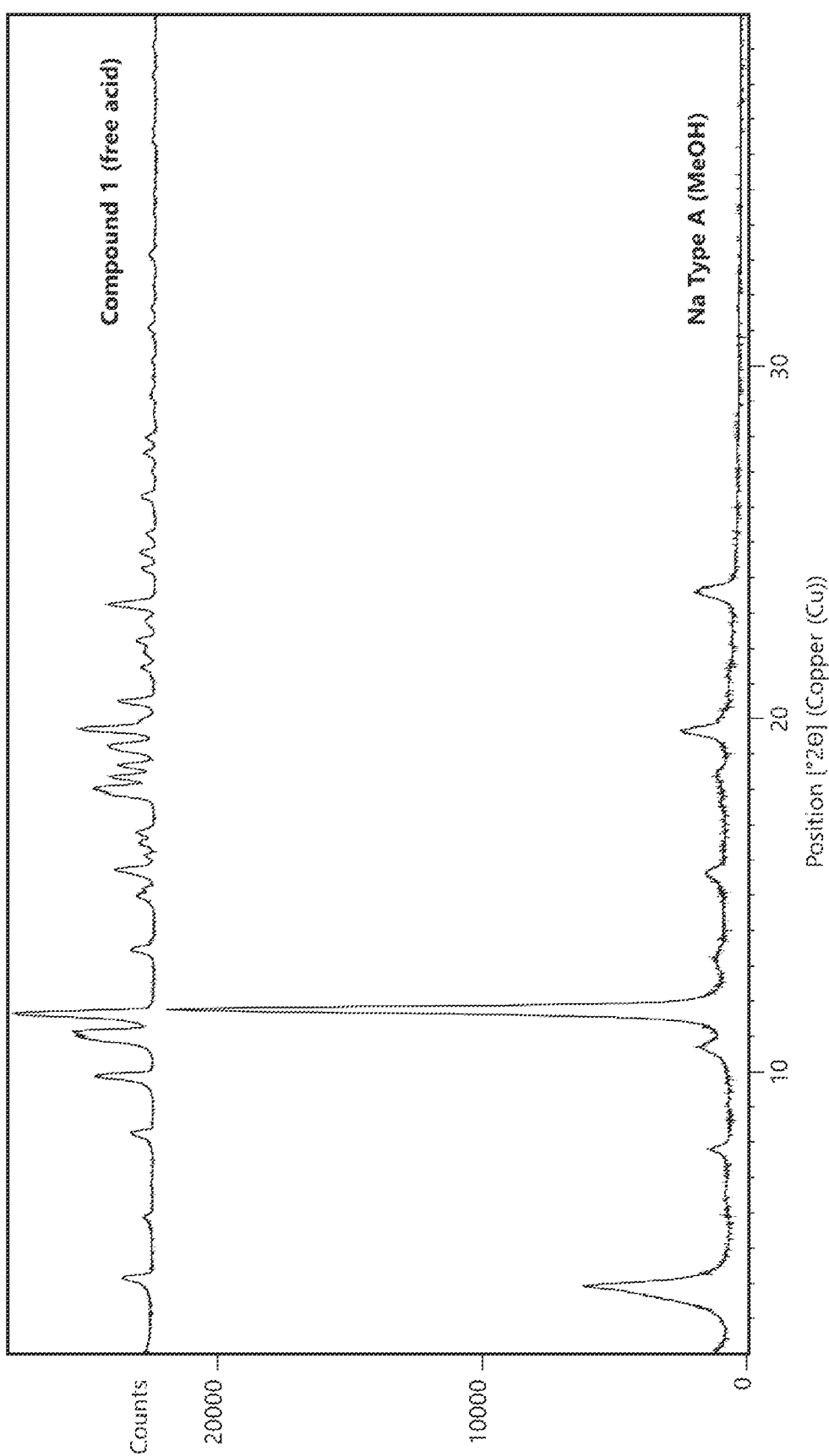
FIG. 9A shows XRPD traces of Compound 1 and the Form A sodium (Na) salt of Compound 1: Compound 1 (free acid); and Na Type A (from evaporation of methanol).
Figure 9B:
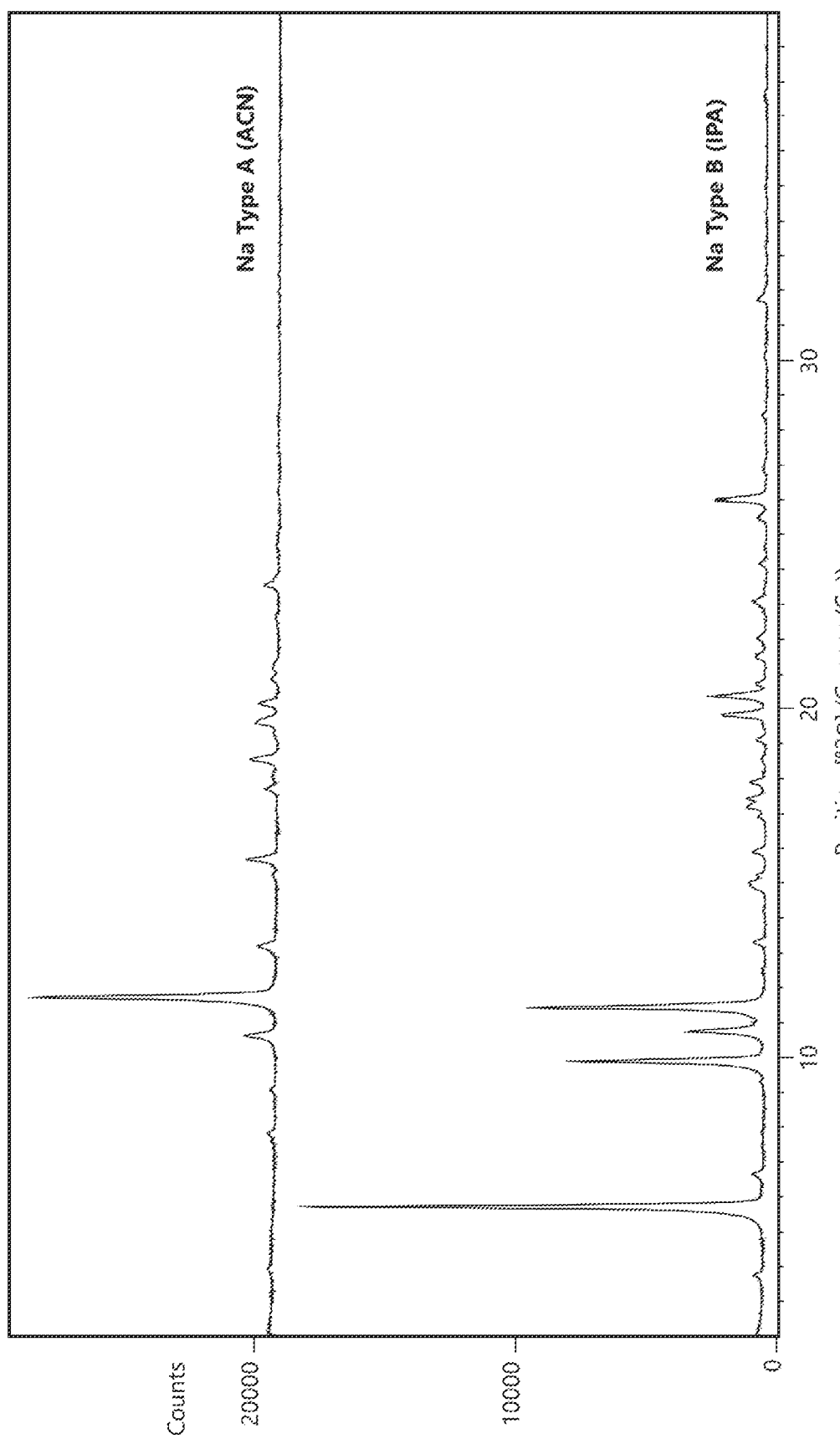
FIG. 9B shows XRPD traces of the Form A/B sodium (Na) salts of Compound 1: Na Type A (from acetonitrile); and Na Type B (from isopropanol).
Figure 10A:
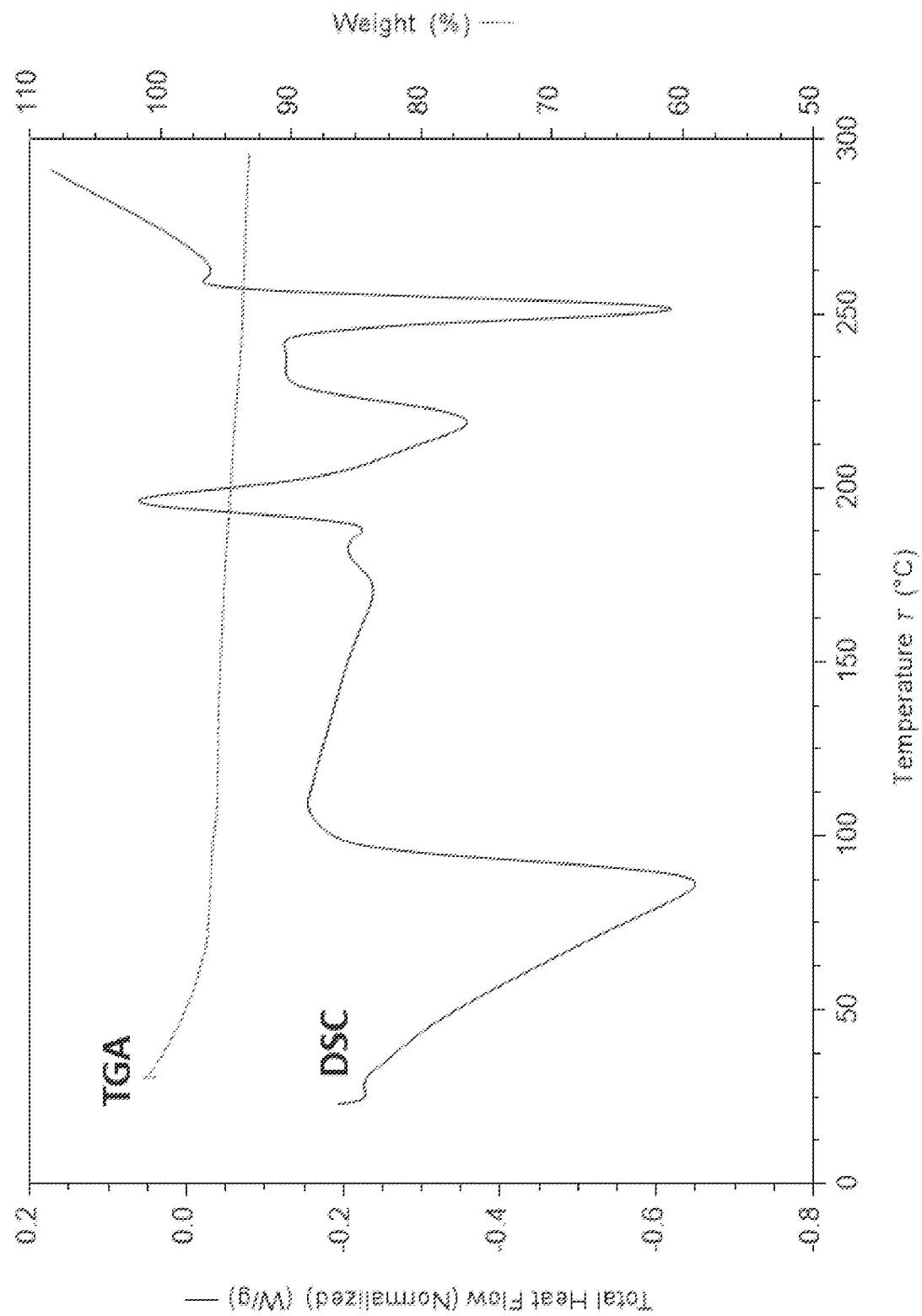
FIG. 10A shows DSC/TGA traces of the Form A sodium salt of Compound 1.
Figure 10B:
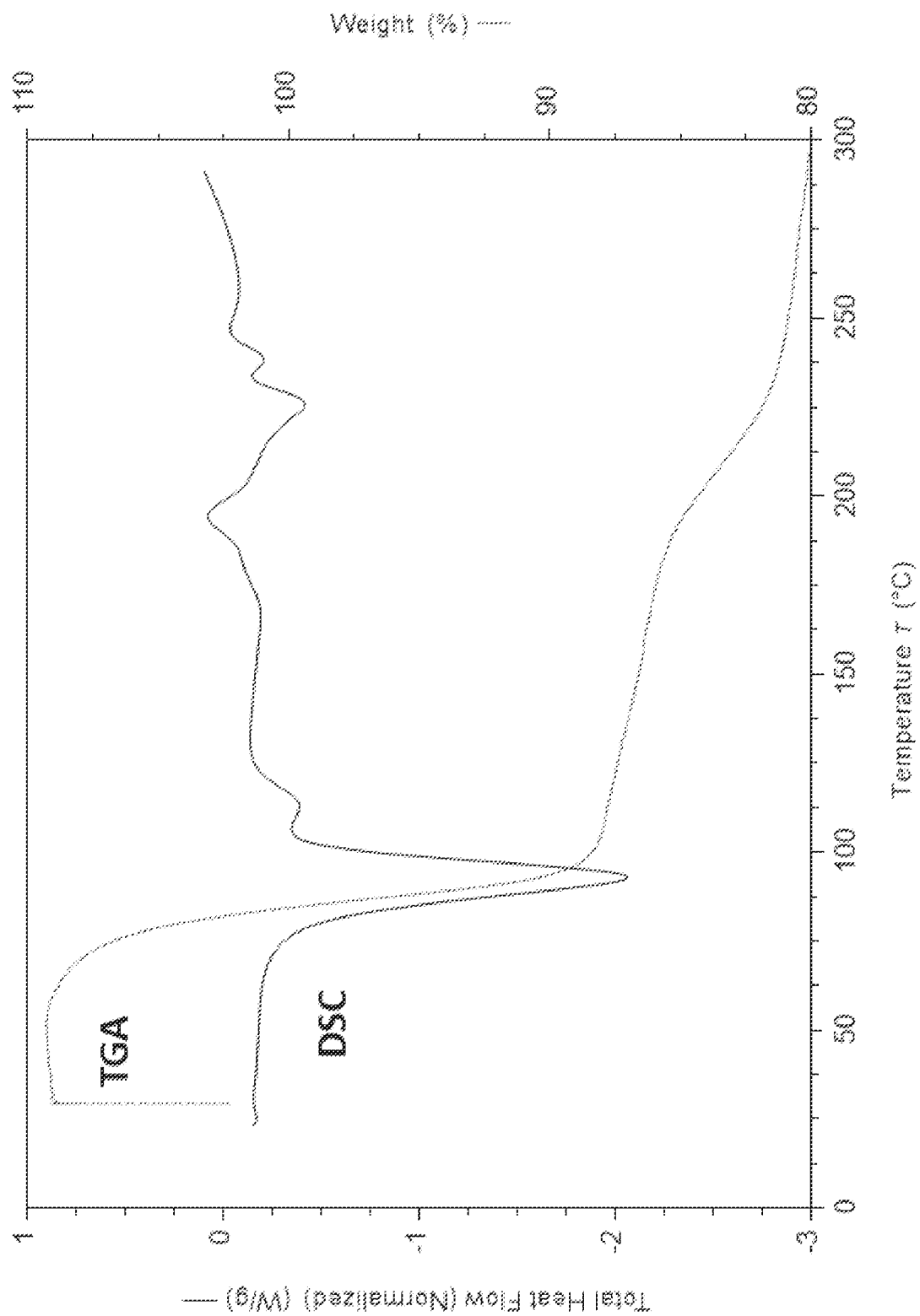
FIG. 10B shows DSC/TGA traces of the Form B sodium salt of Compound 1.
Figure 10C:
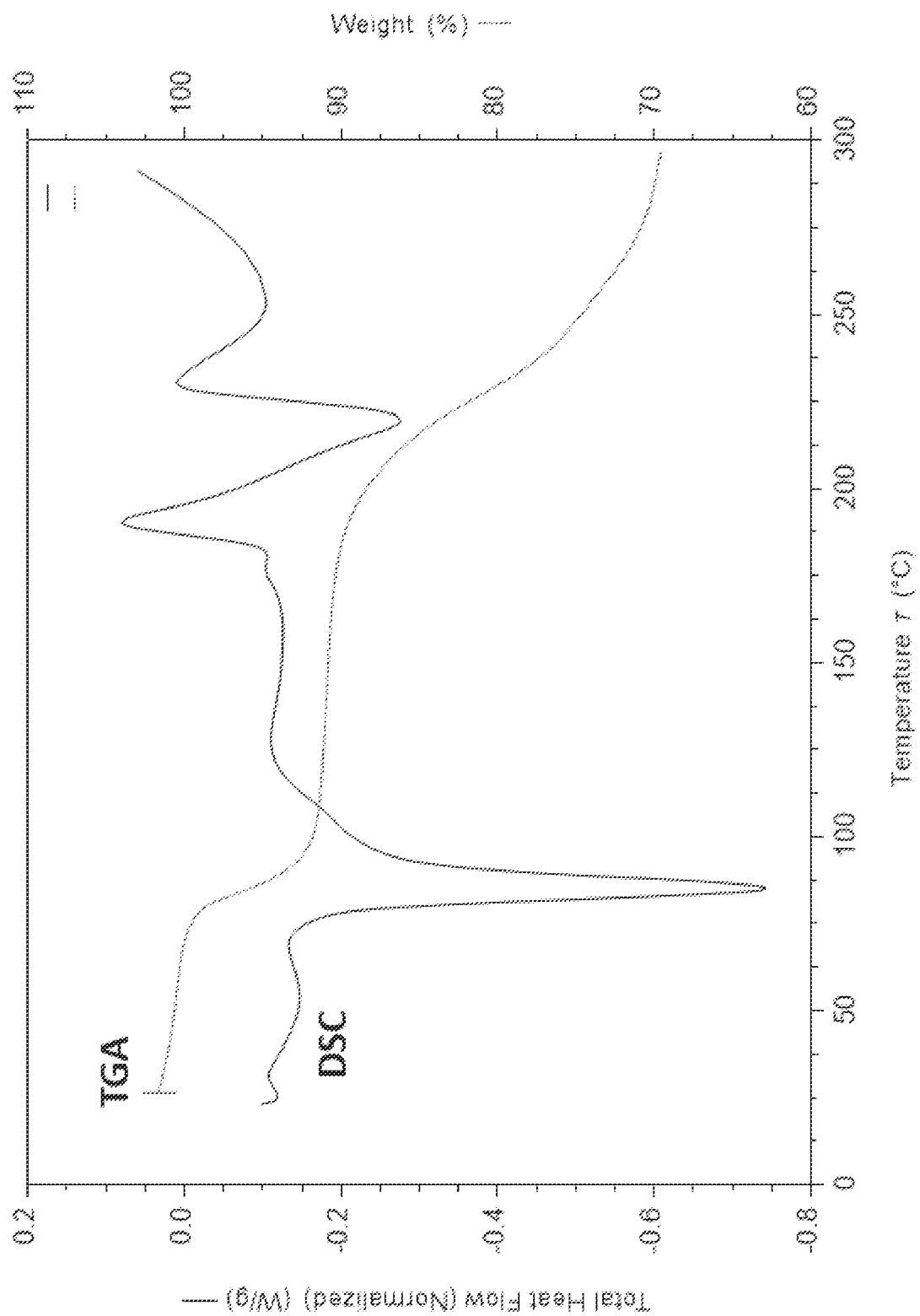
FIG. 10C shows DSC/TGA traces of the Form C sodium salt of Compound 1.
Figure 10D:
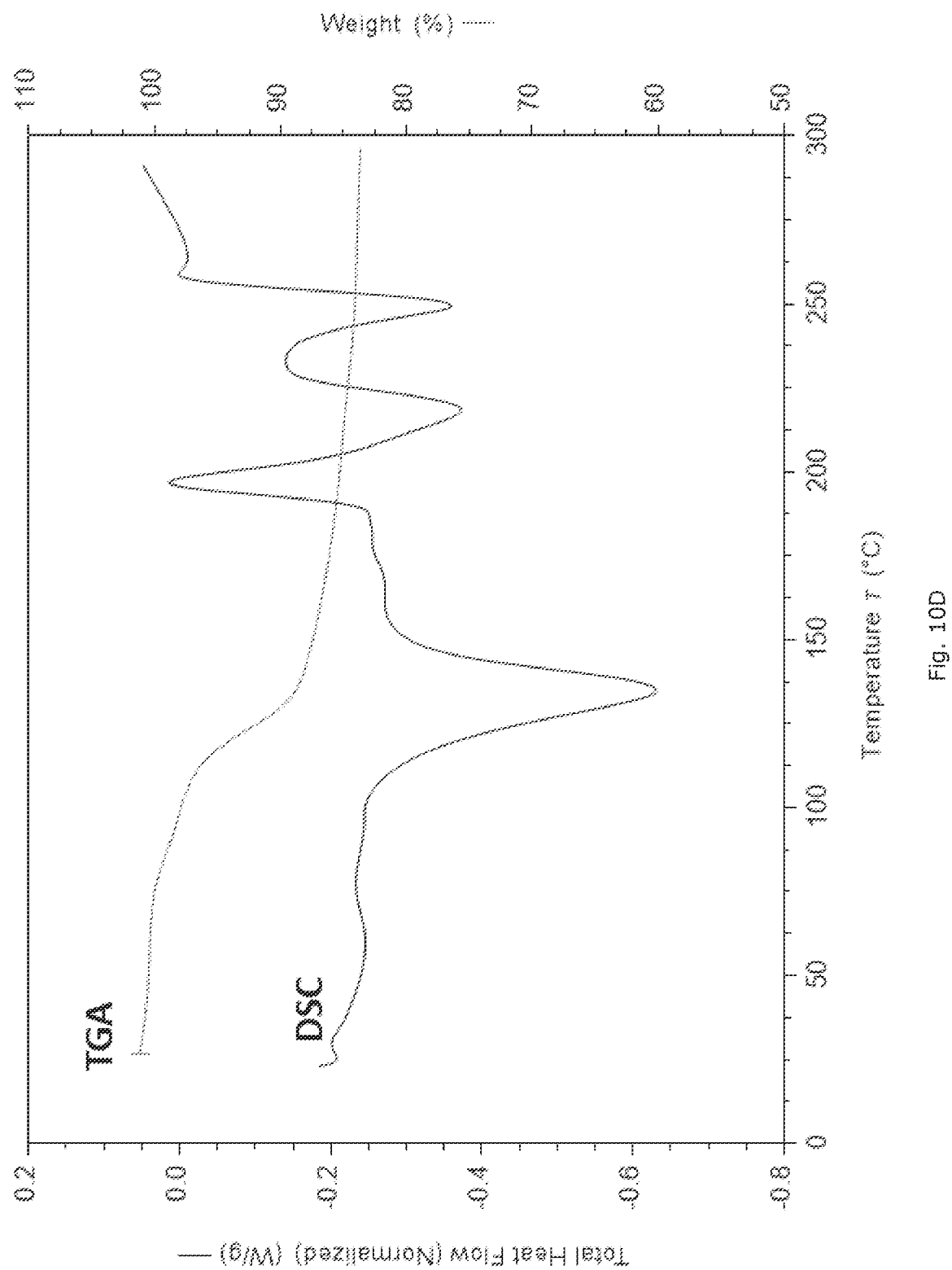
FIG. 10D shows DSC/TGA traces of the Form D sodium salt of Compound 1.
Figure 12A:
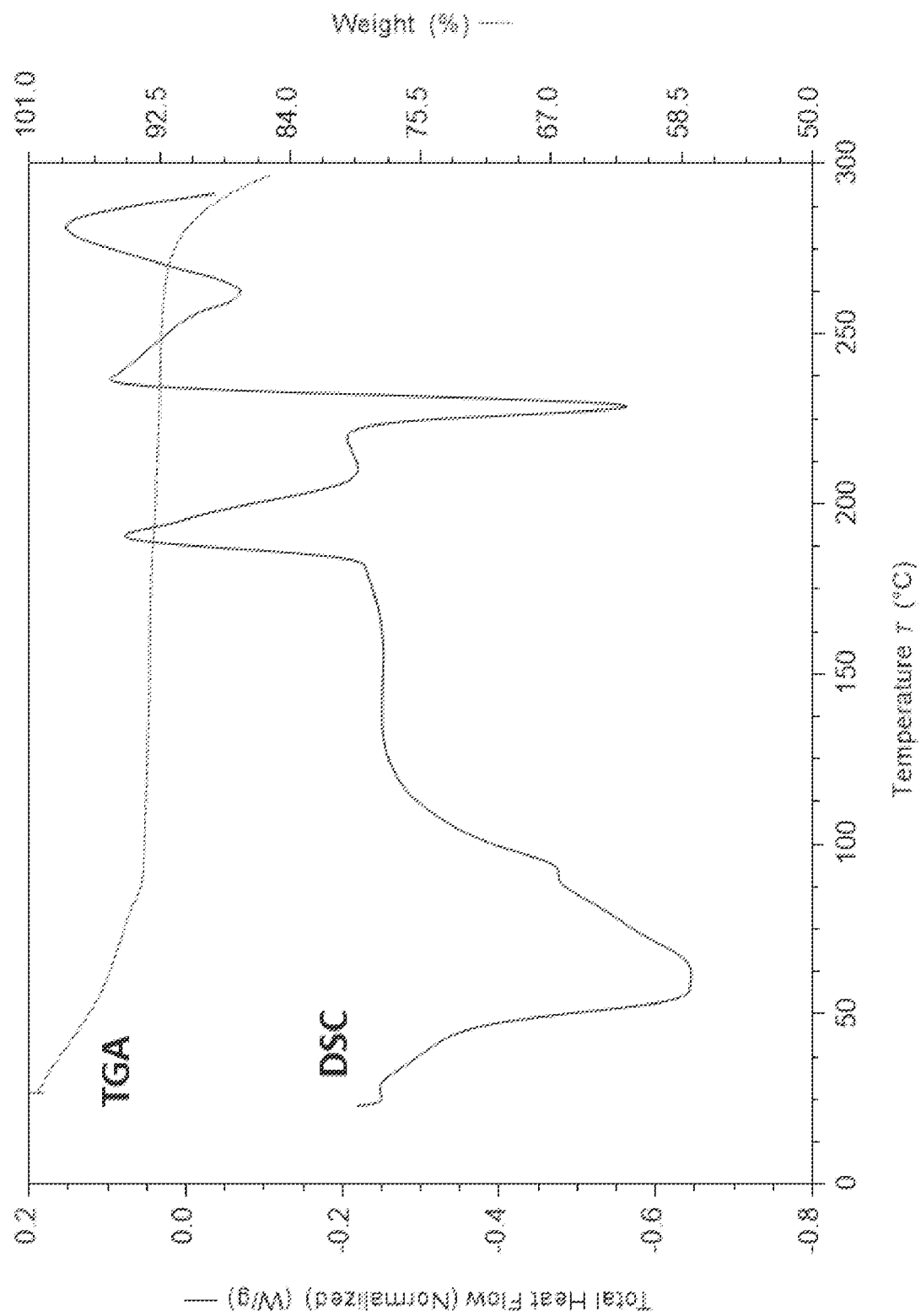
FIG. 12A shows DSC/TGA traces of the Form A potassium salt of Compound 1.
Figure 12B:
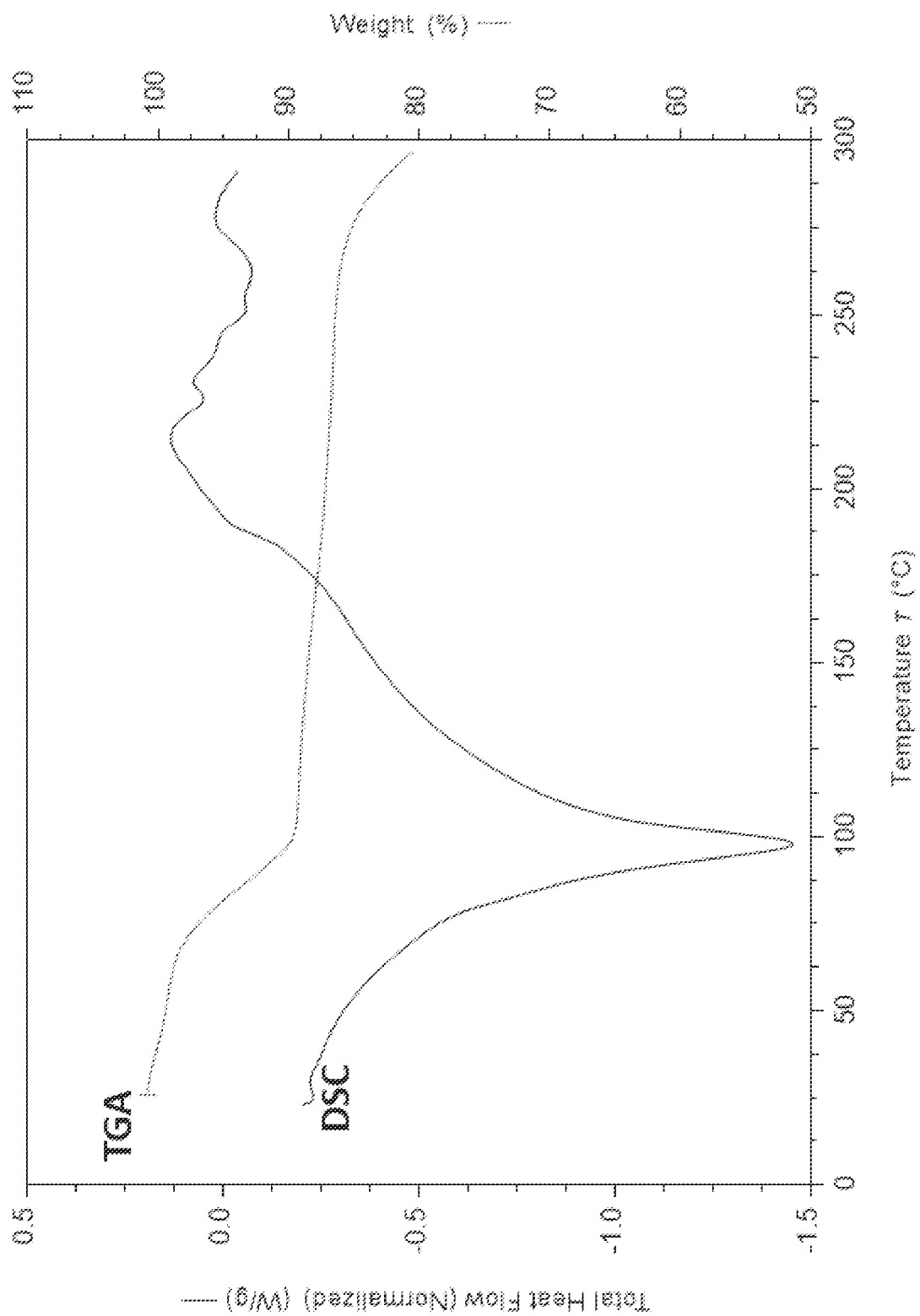
FIG. 12B shows DSC/TGA traces of the Form B potassium salt of Compound 1.
Figure 12C:
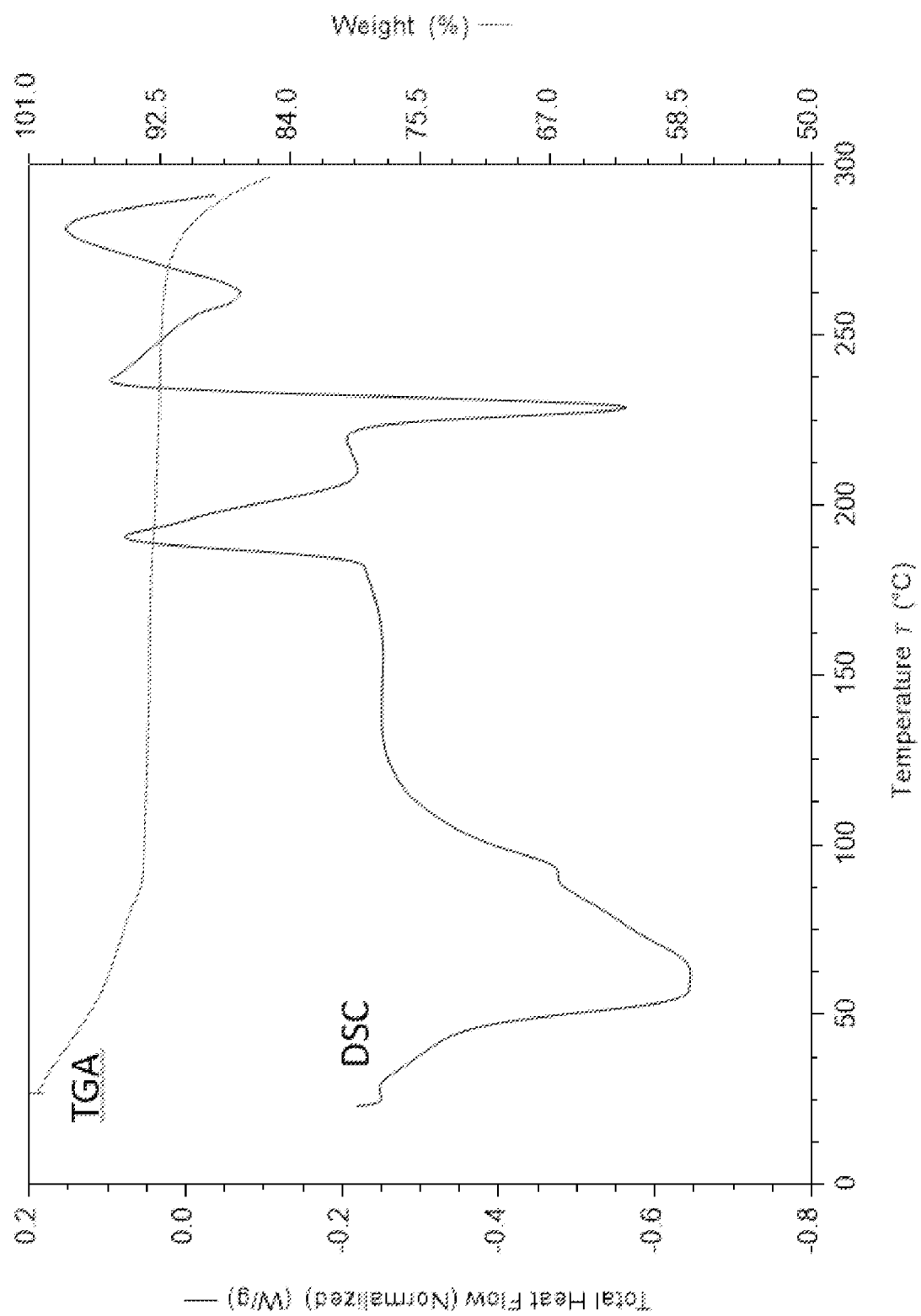
FIG. 12C shows DSC/TGA traces of the Form C potassium salt of Compound 1.
Figure 12D:
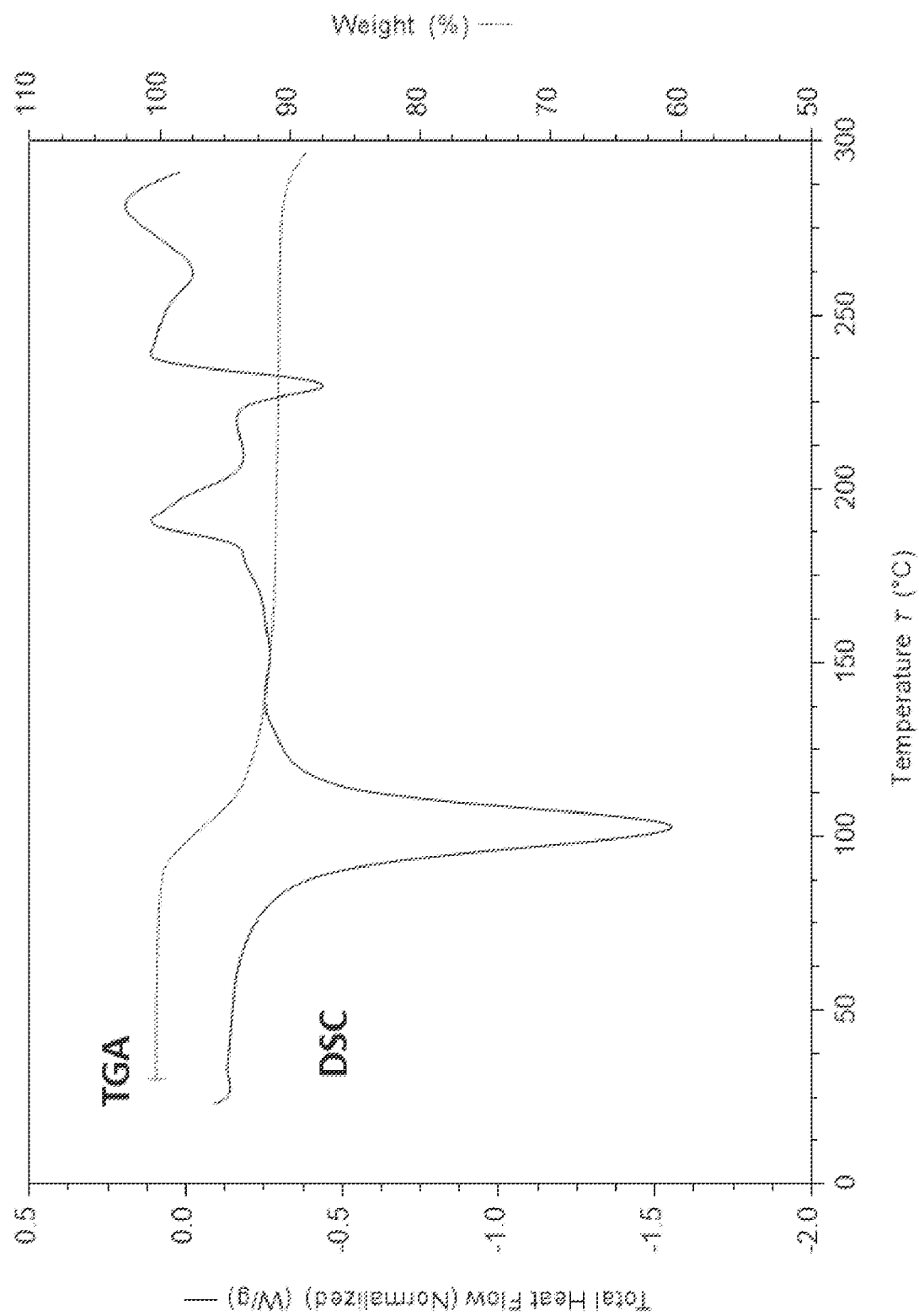
FIG. 12D shows DSC/TGA traces of the Form D potassium salt of Compound 1.
Figure 12E:
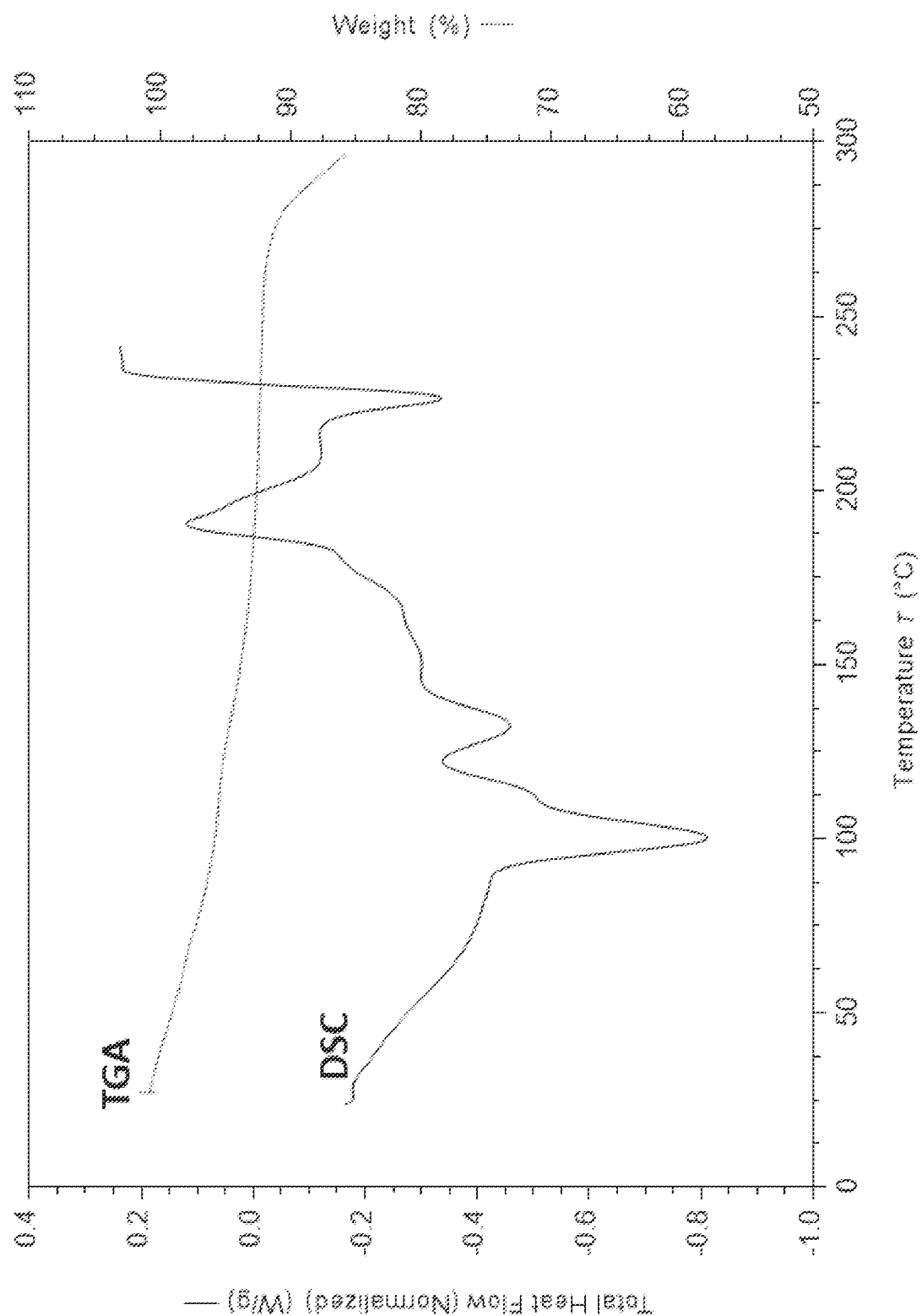
FIG. 12E shows DSC/TGA traces of the Form E potassium salt of Compound 1.
Figure 13A:
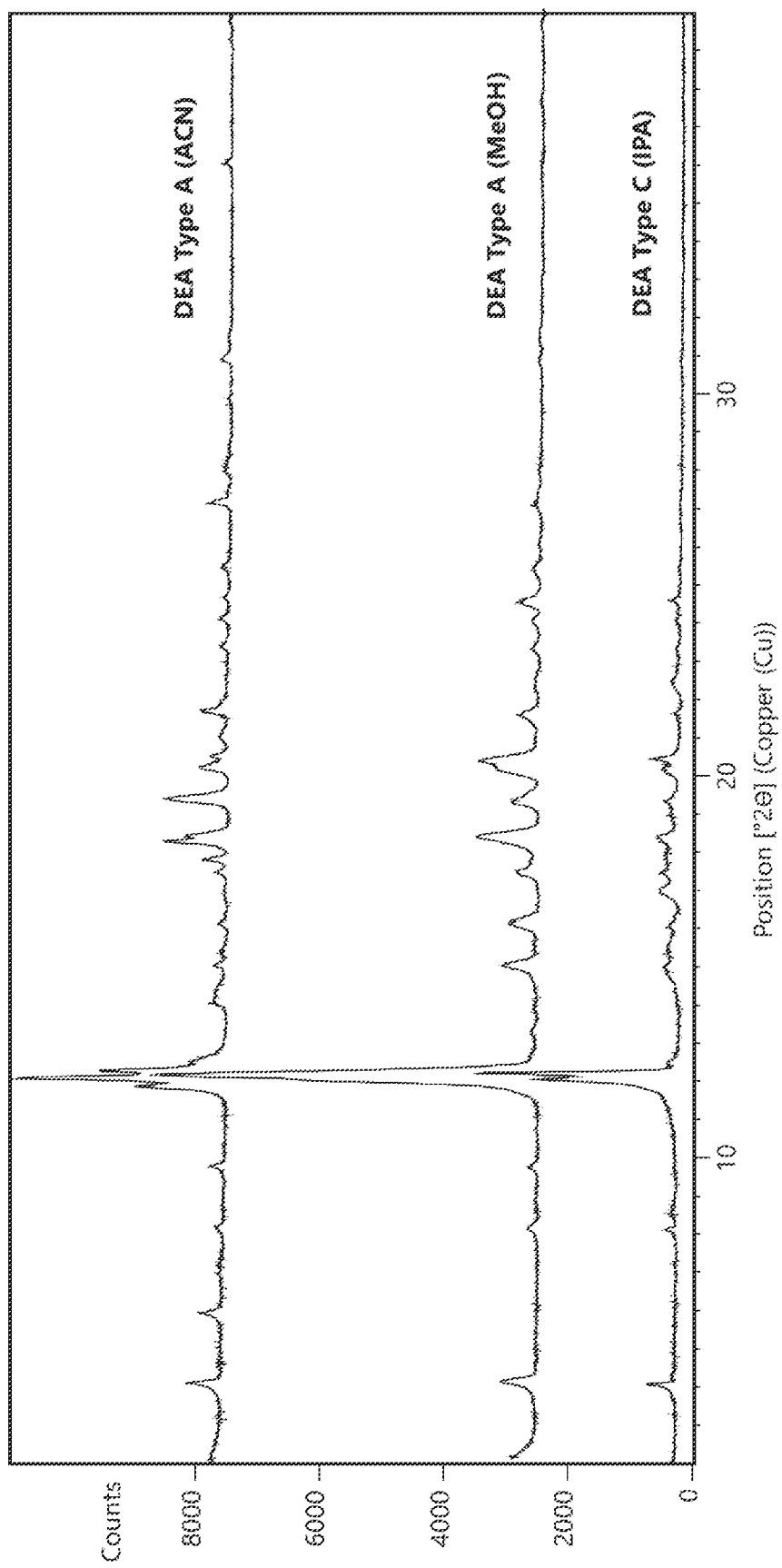
FIG. 13A shows XRPD traces of the Form A/C diethylamine (DEA) salts of Compound 1: DEA Type A (from acetonitrile); DEA Type A (from evaporation of methanol); and DEA Type C (from isopropanol).
Figure 14A:
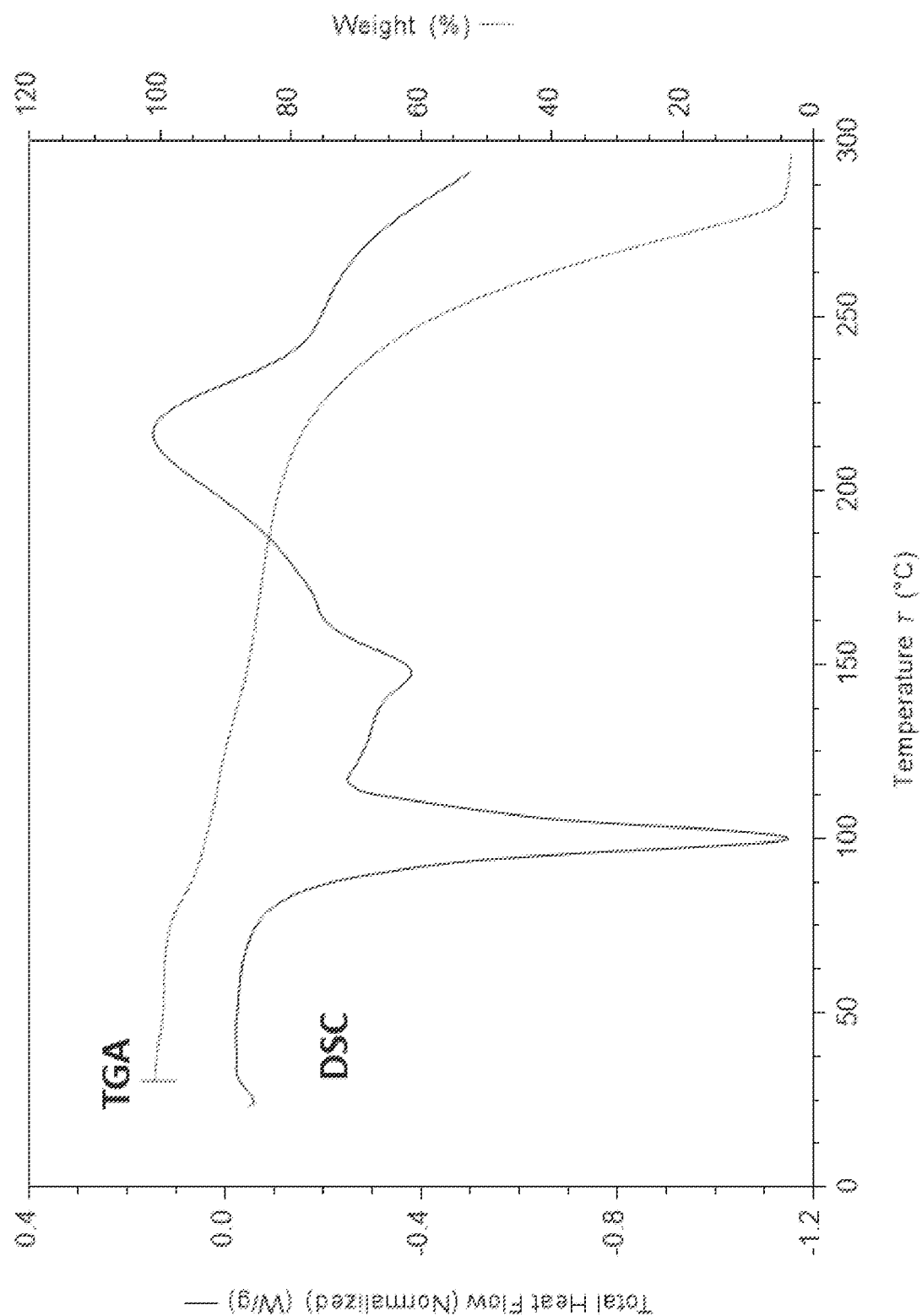
FIG. 14A shows DSC/TGA traces of the Form A diethylamine salt of Compound 1.
Figure 14B:
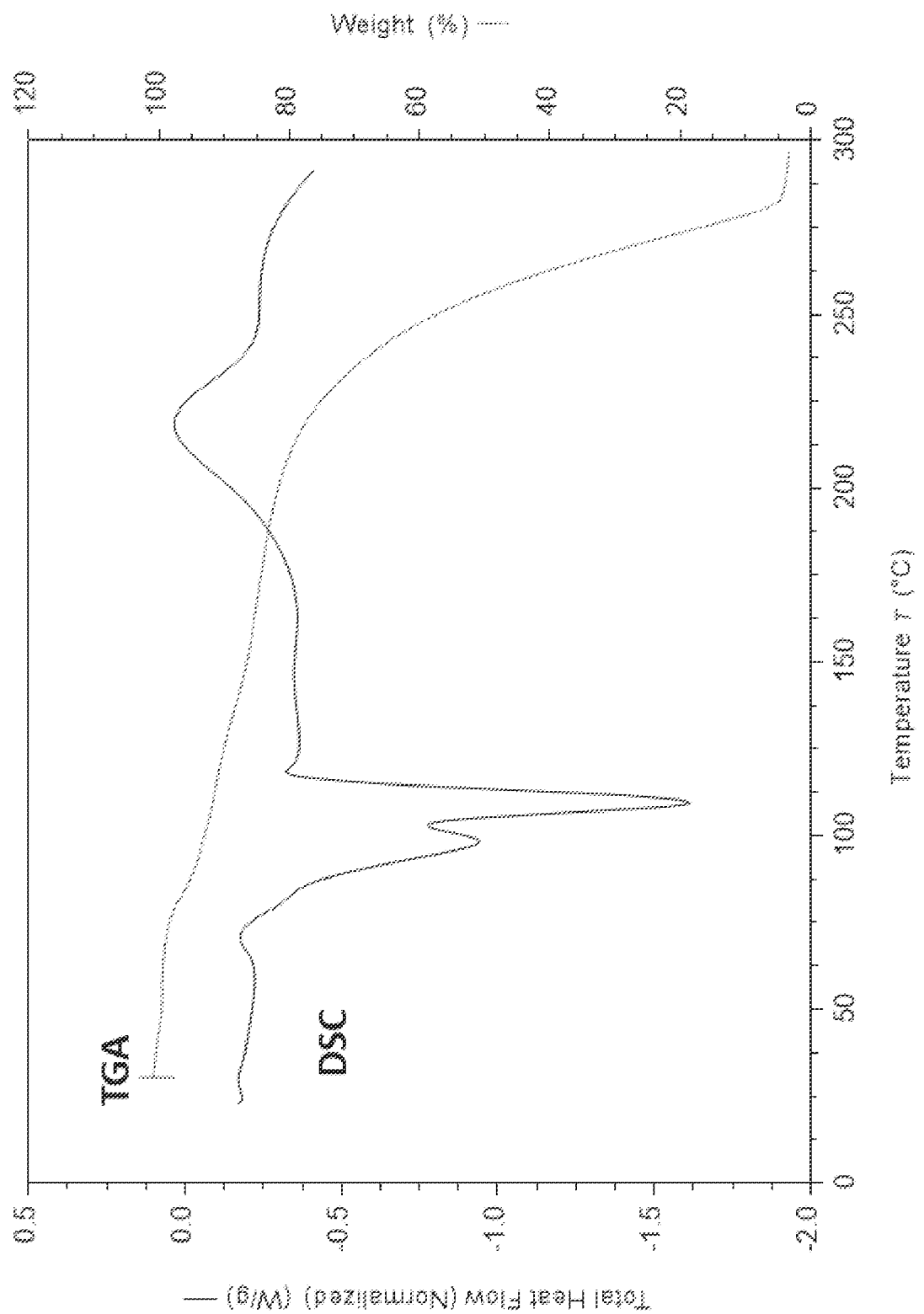
FIG. 14B shows DSC/TGA traces of the Form B diethylamine salt of Compound 1.
Figure 14C:
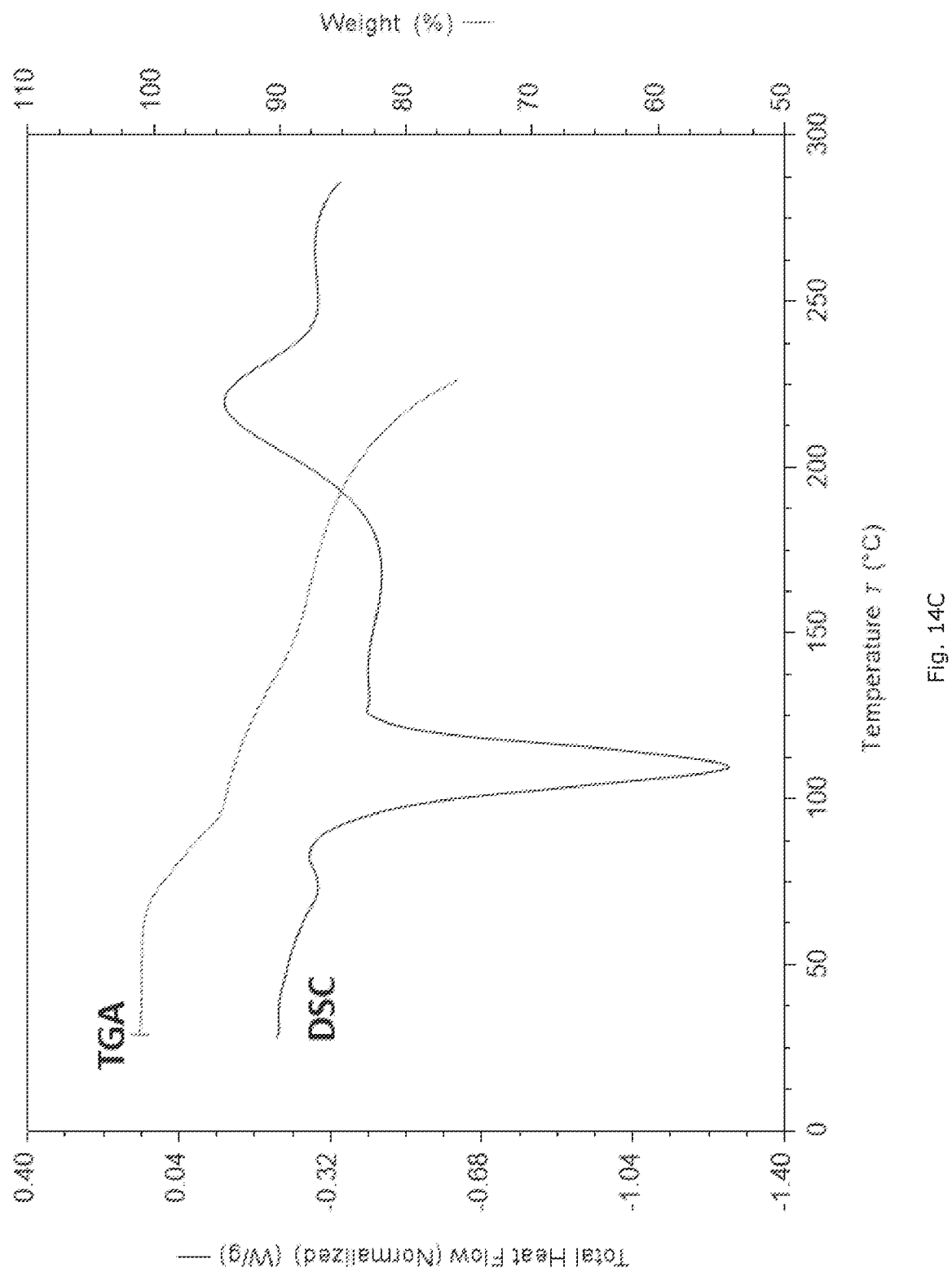
FIG. 14C shows DSC/TGA traces of the Form C diethylamine salt of Compound 1.
Figure 15A:
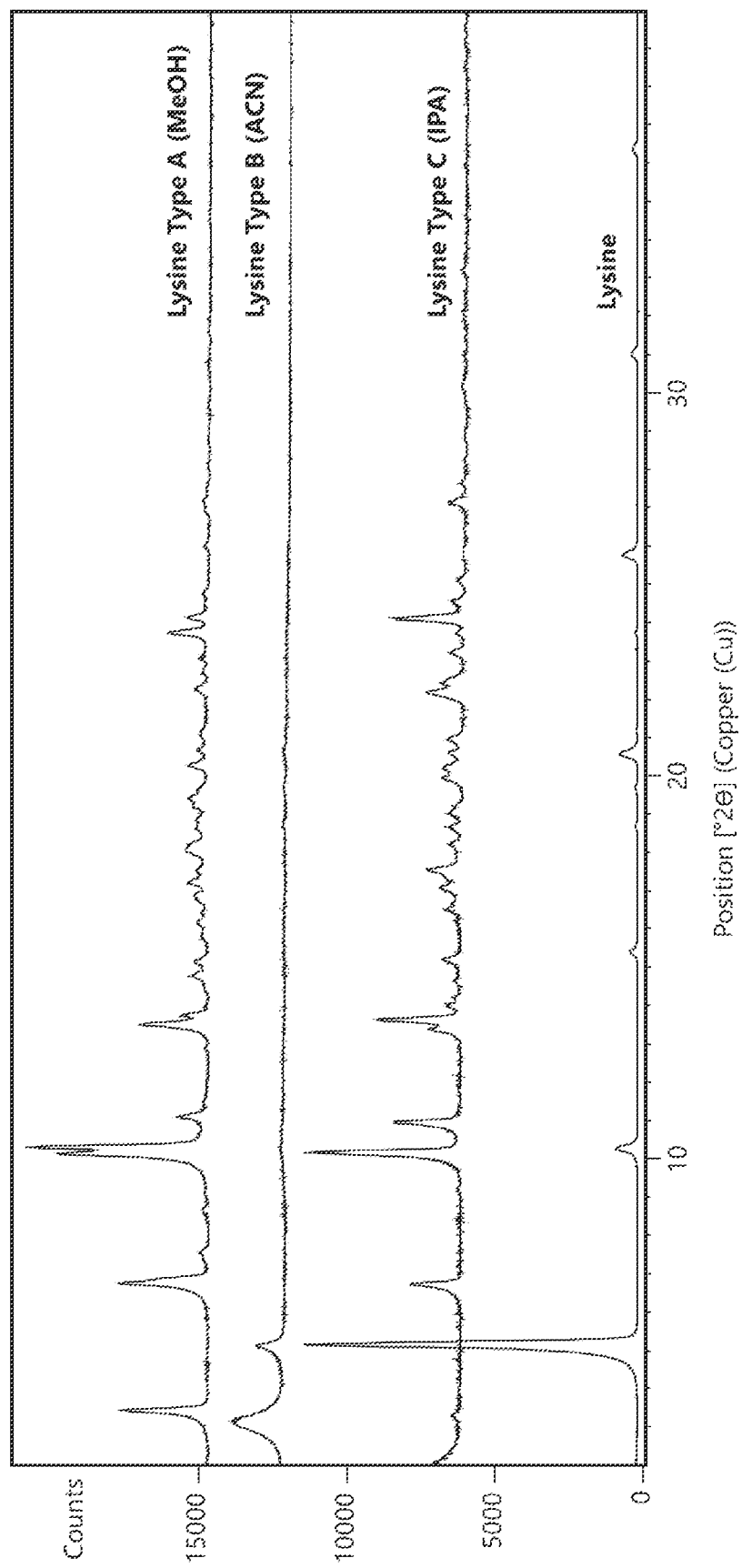
FIG. 15A shows XRPD traces of lysine and the Form A/B/C lysine salts of Compound 1: lysine; lysine Type A (from methanol); lysine Type B (from acetonitrile); and lysine Type C (from isopropanol).
Figure 15B:
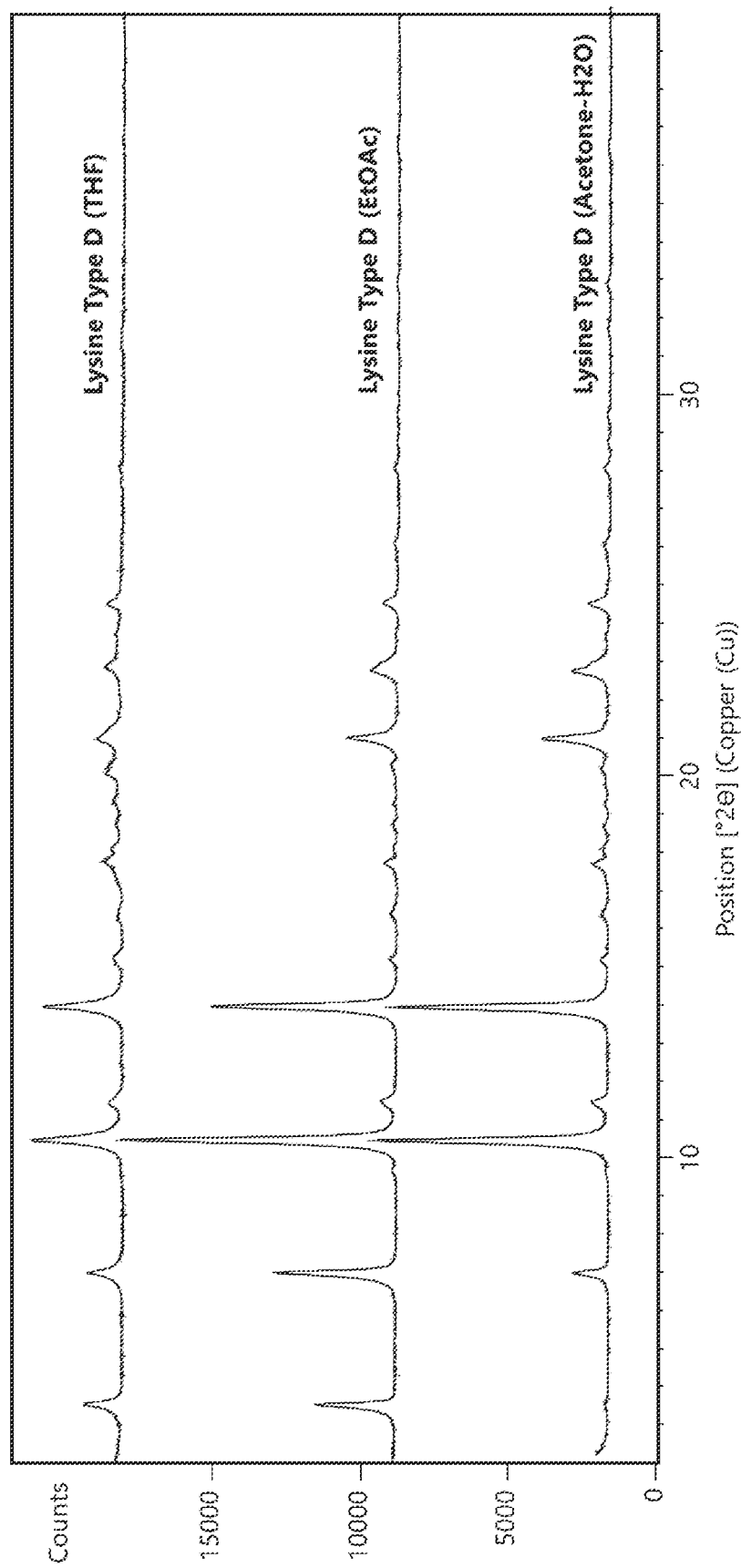
FIG. 15B shows XRPD traces of lysine and the Form D lysine salt of Compound 1: lysine Type D (from tetrahydrofuran); lysine Type D (from ethyl acetate); and lysine Type D (from acetone-$H_2O$ 5:1).
Figure 16A:
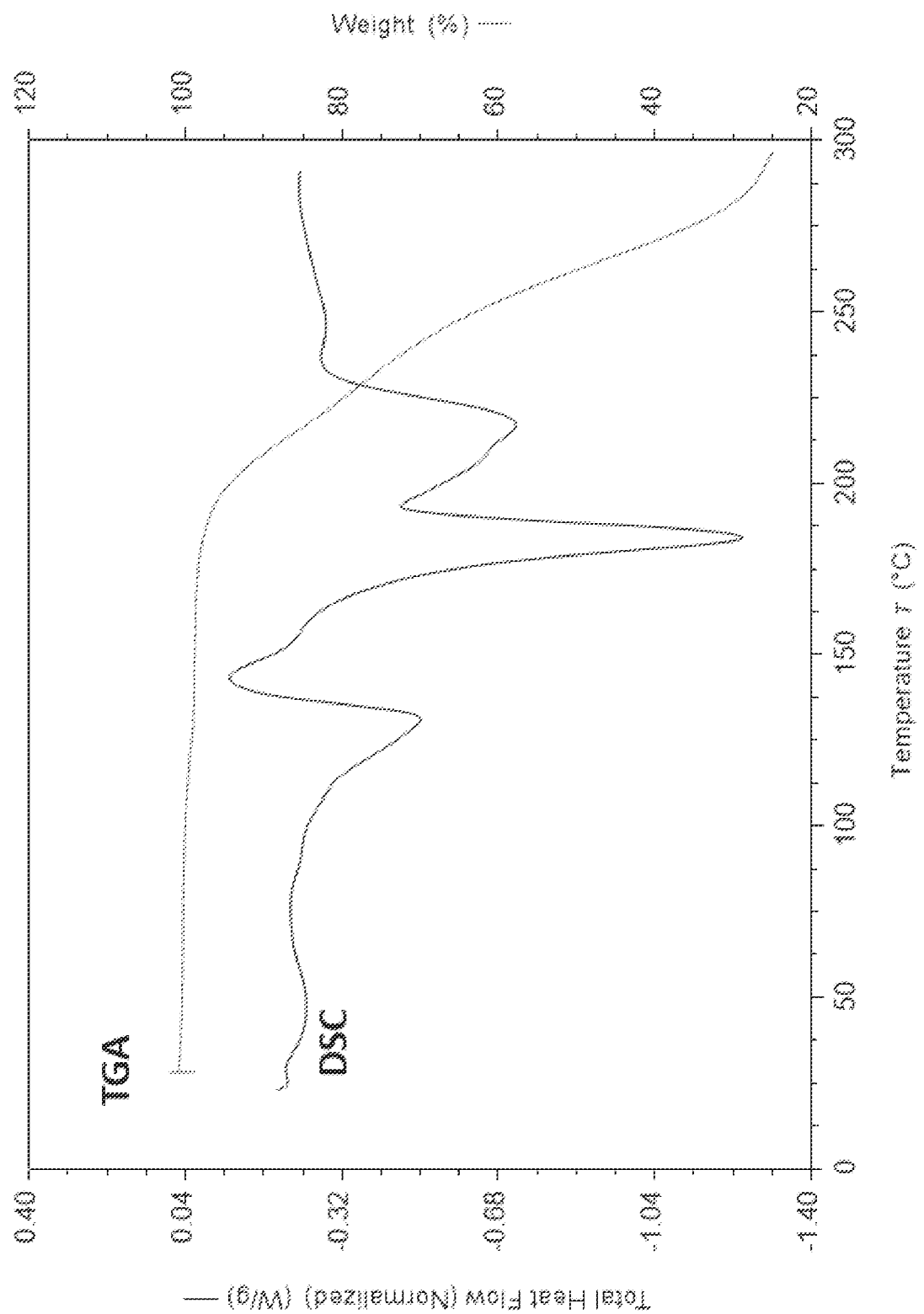
FIG. 16A shows DSC/TGA traces of the Form A lysine salt of Compound 1.
Figure 16B:
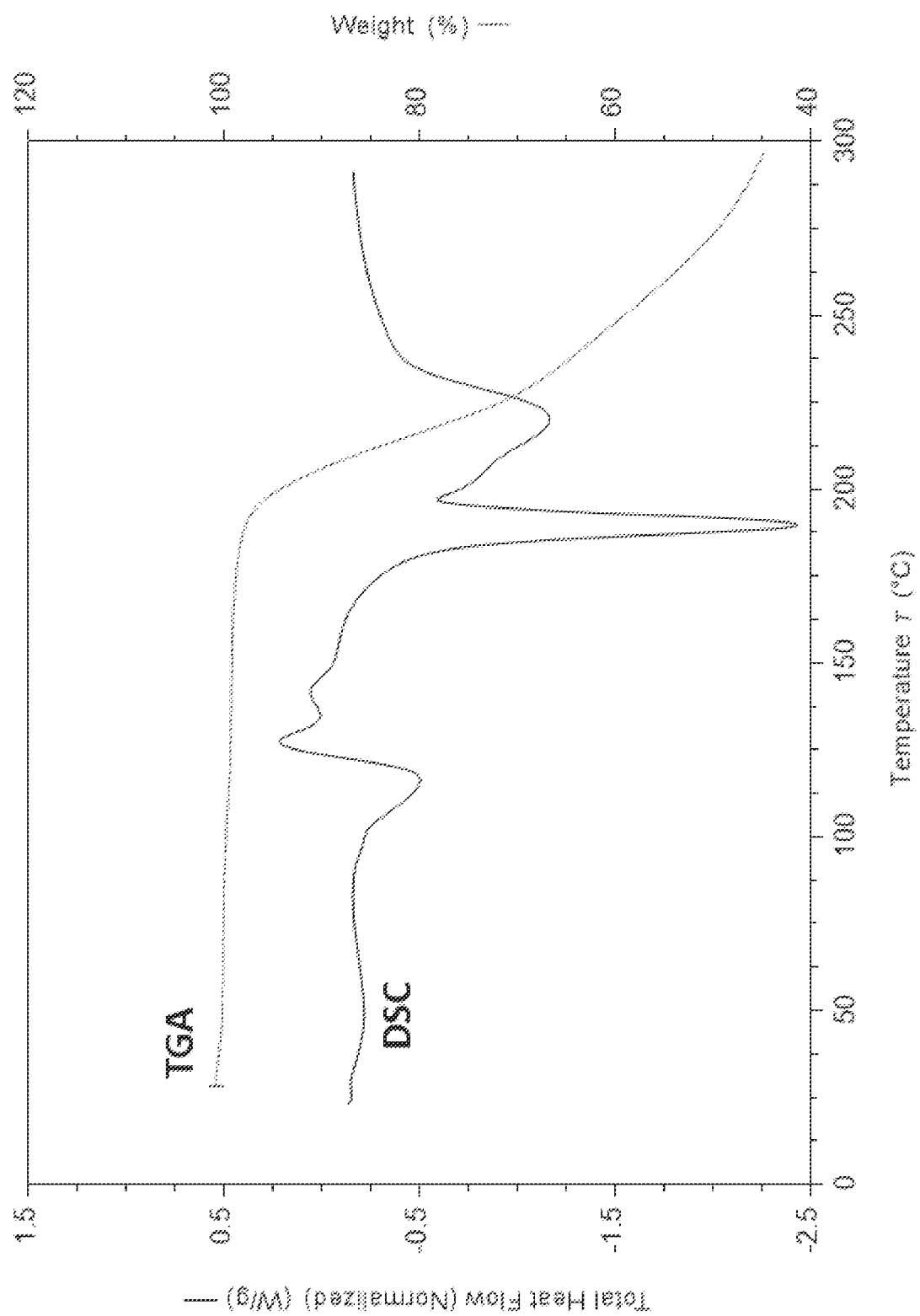
FIG. 16B shows DSC/TGA traces of the Form B lysine salt of Compound 1.
Figure 16C:
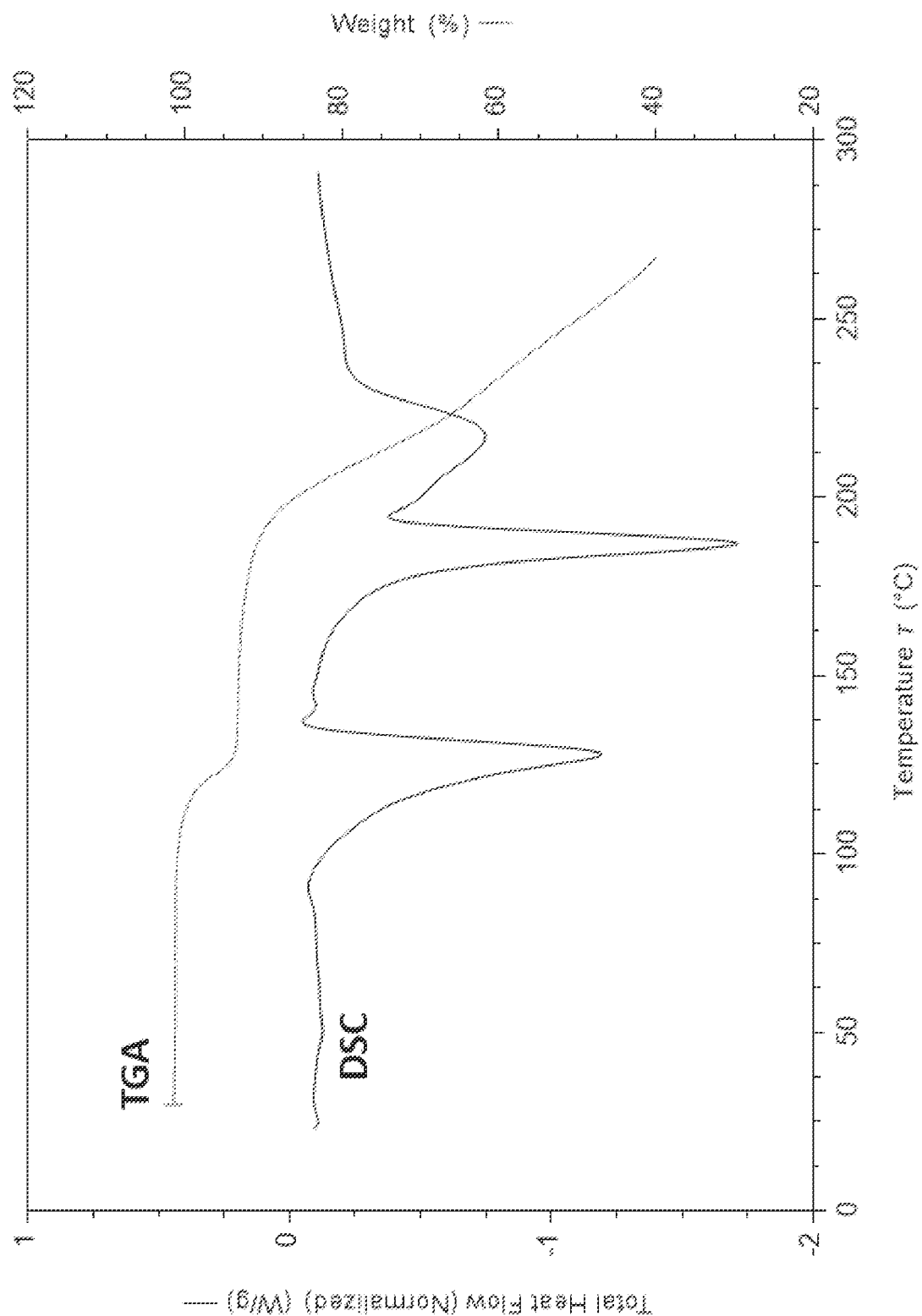
FIG. 16C shows DSC/TGA traces of the Form C lysine salt of Compound 1.
Figure 16D:
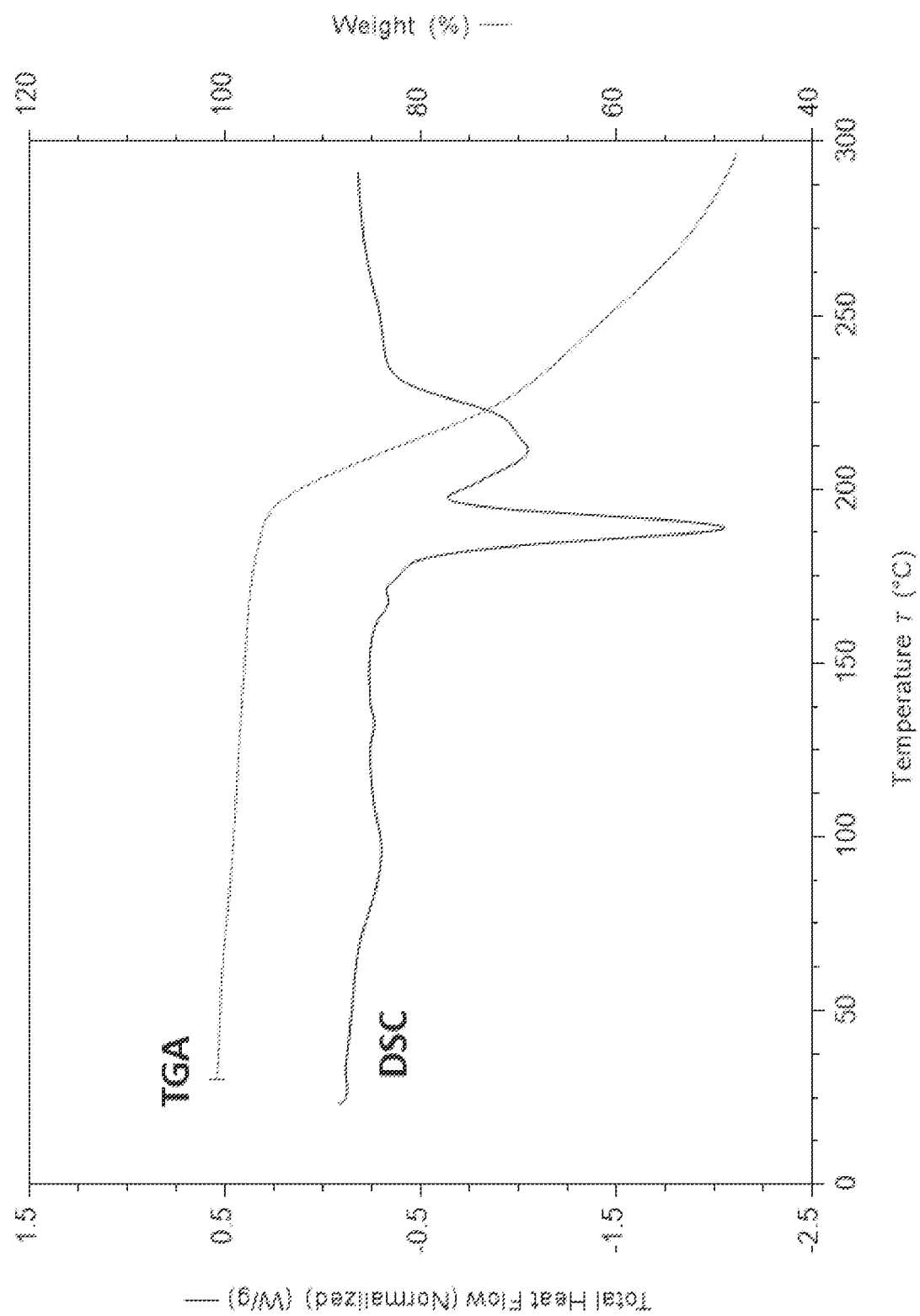
FIG. 16D shows DSC/TGA traces of the Form D lysine salt of Compound 1.
Figure 17:
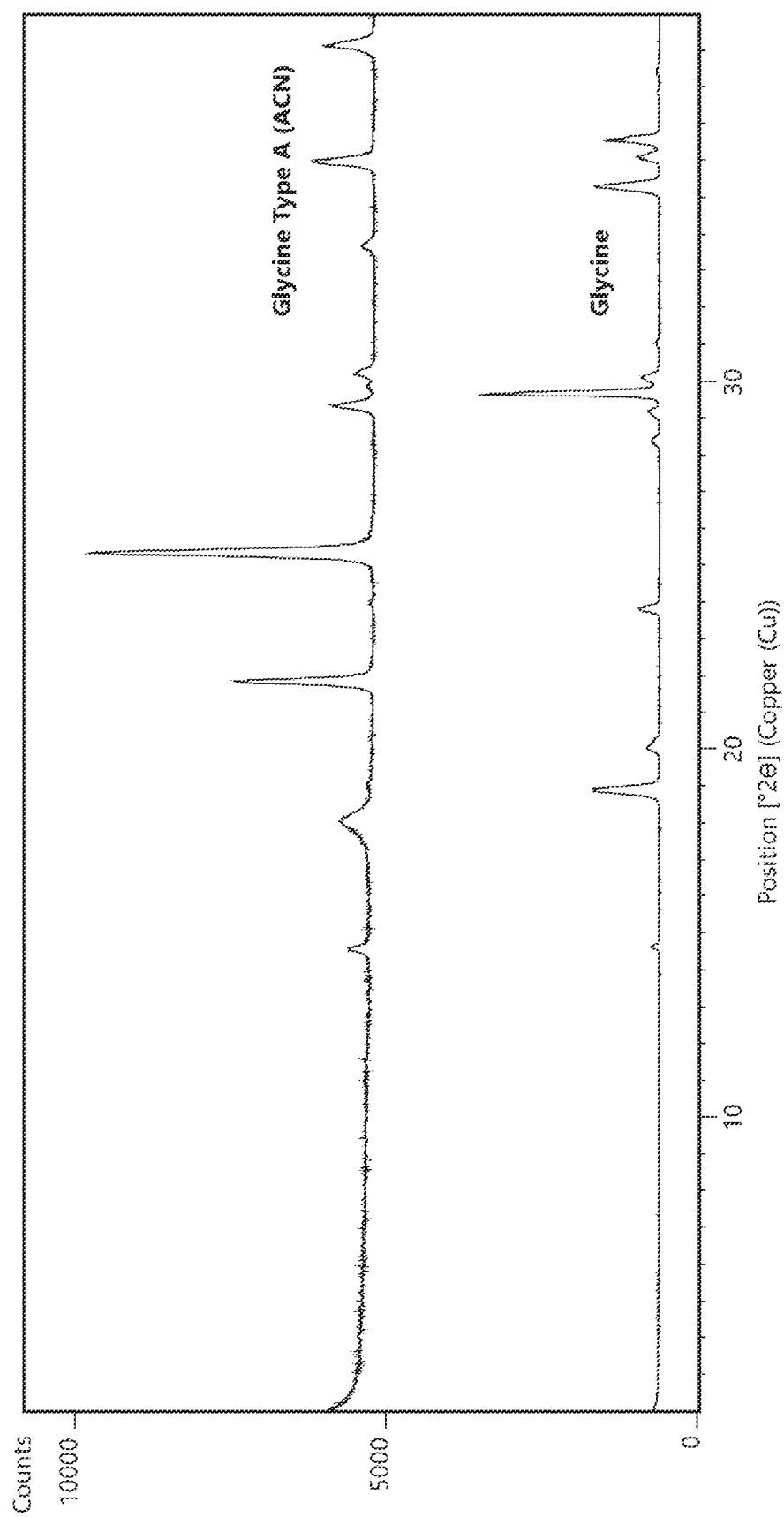
FIG. 17 shows XRPD traces of glycine and the Form A glycine salt of Compound 1: glycine; and glycine Type A (from acetonitrile).
Figure 18:
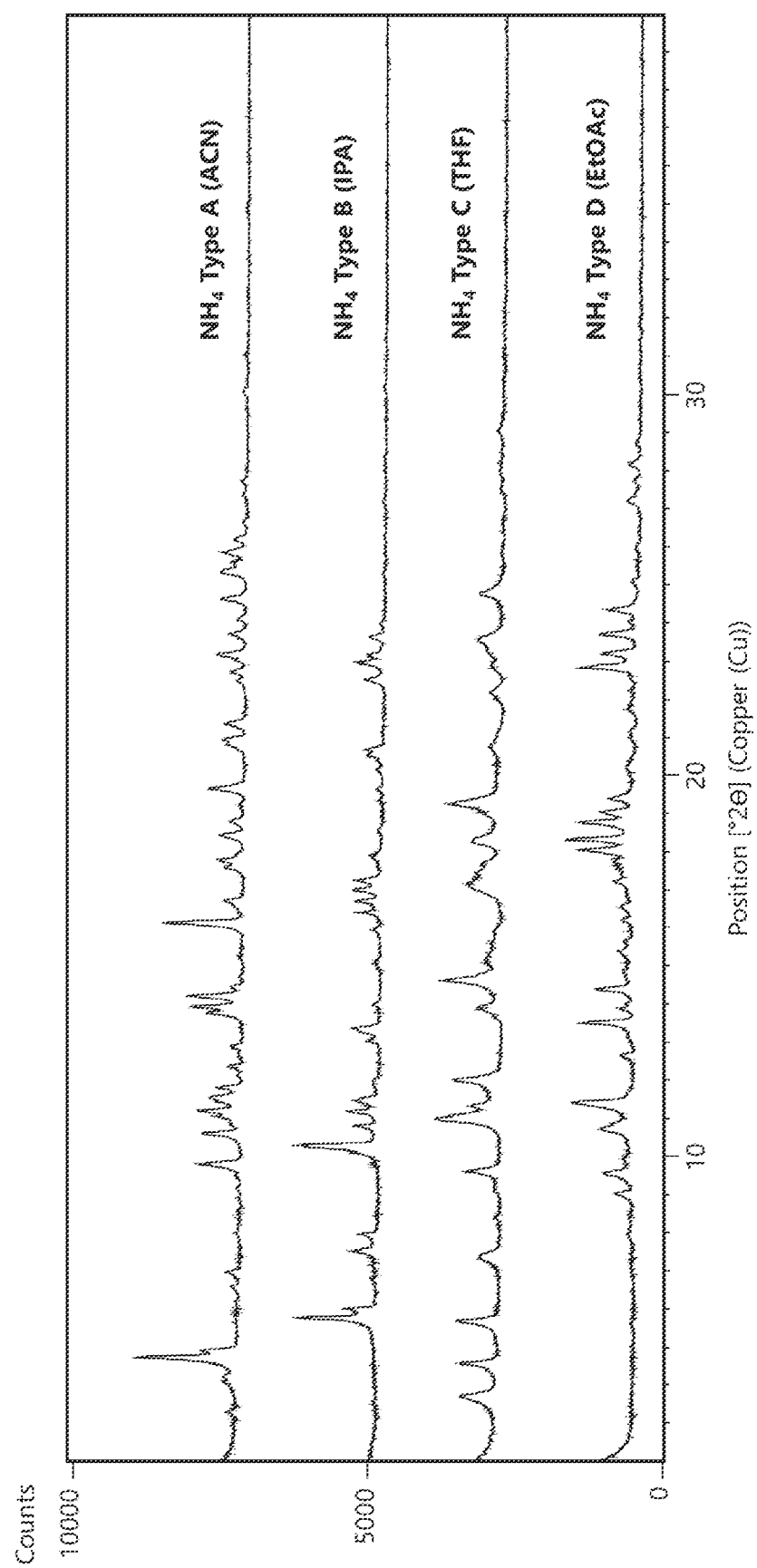
FIG. 18 shows XRPD traces of the Form A/B/C/D ammonium ($NH_4$) salts of Compound 1: $NH_4$ Type A (from acetonitrile); $NH_4$ Type B (from isopropanol); $NH_4$ Type C (from tetrahydrofuran); and $NH_4$ Type D (from ethyl acetate).
Figure 19A:
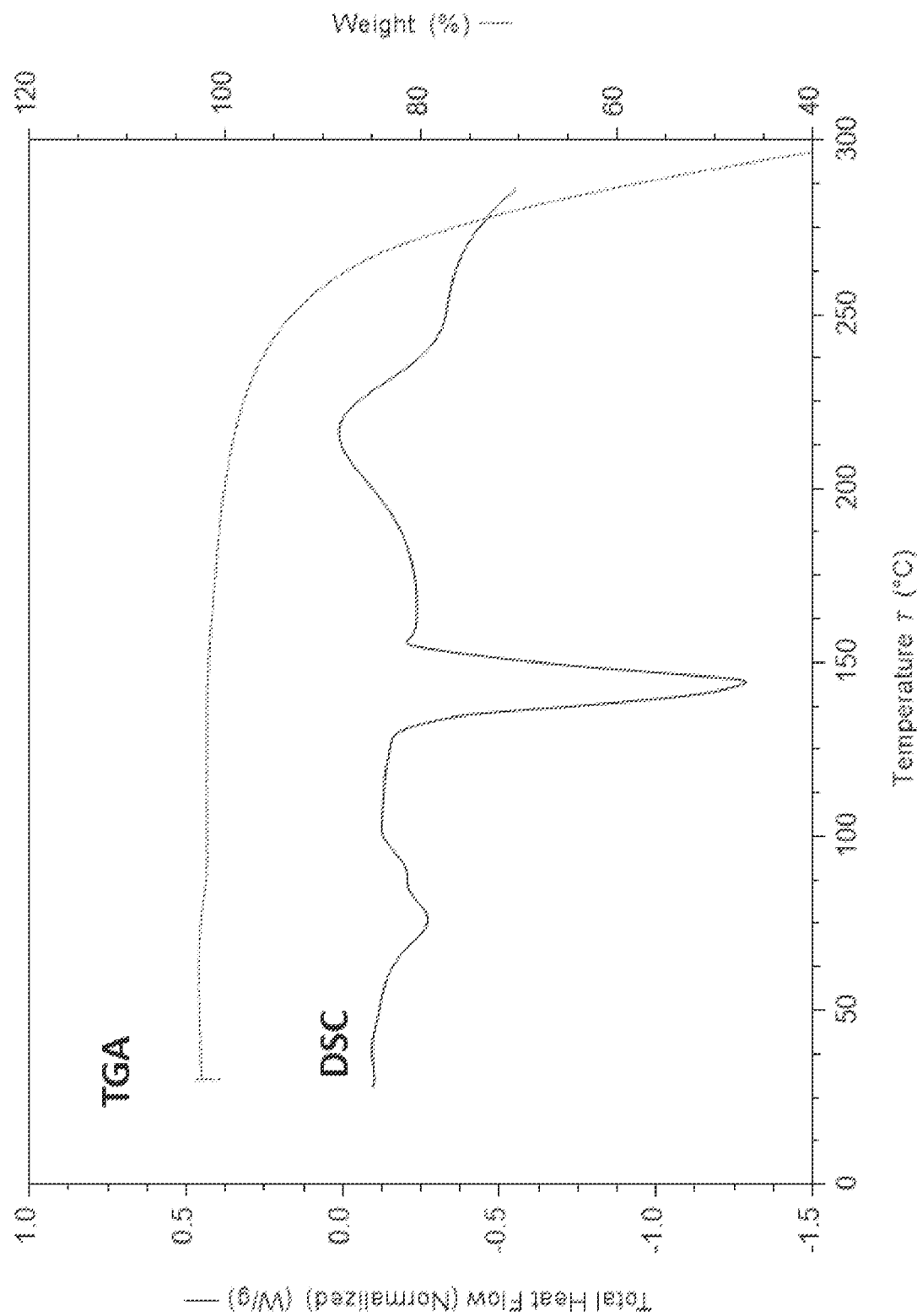
FIG. 19A shows DSC/TGA traces of the Form A ammonium salt of Compound 1.
Figure 19B:
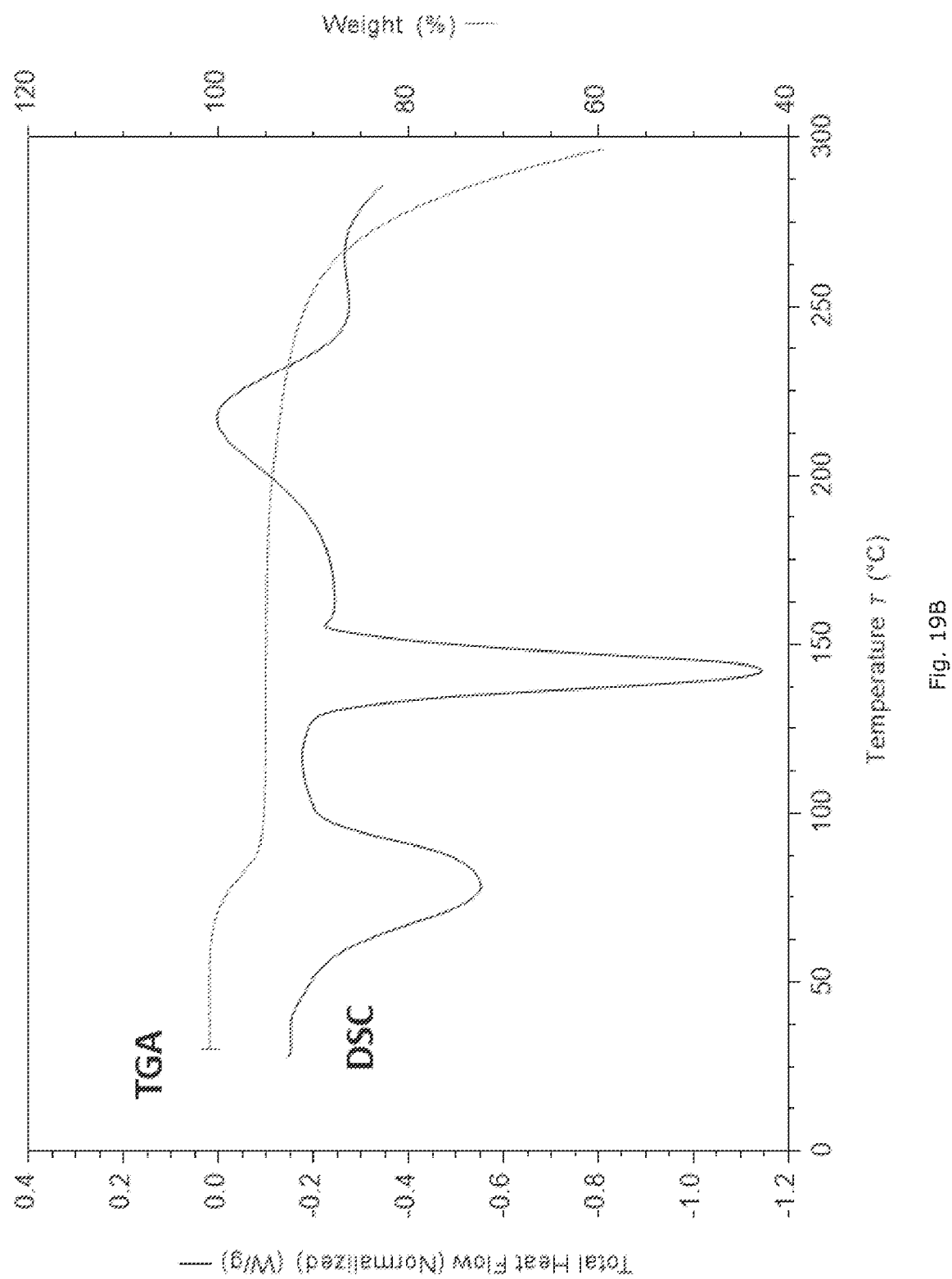
FIG. 19B shows DSC/TGA traces of the Form B ammonium salt of Compound 1.
Figure 19C:
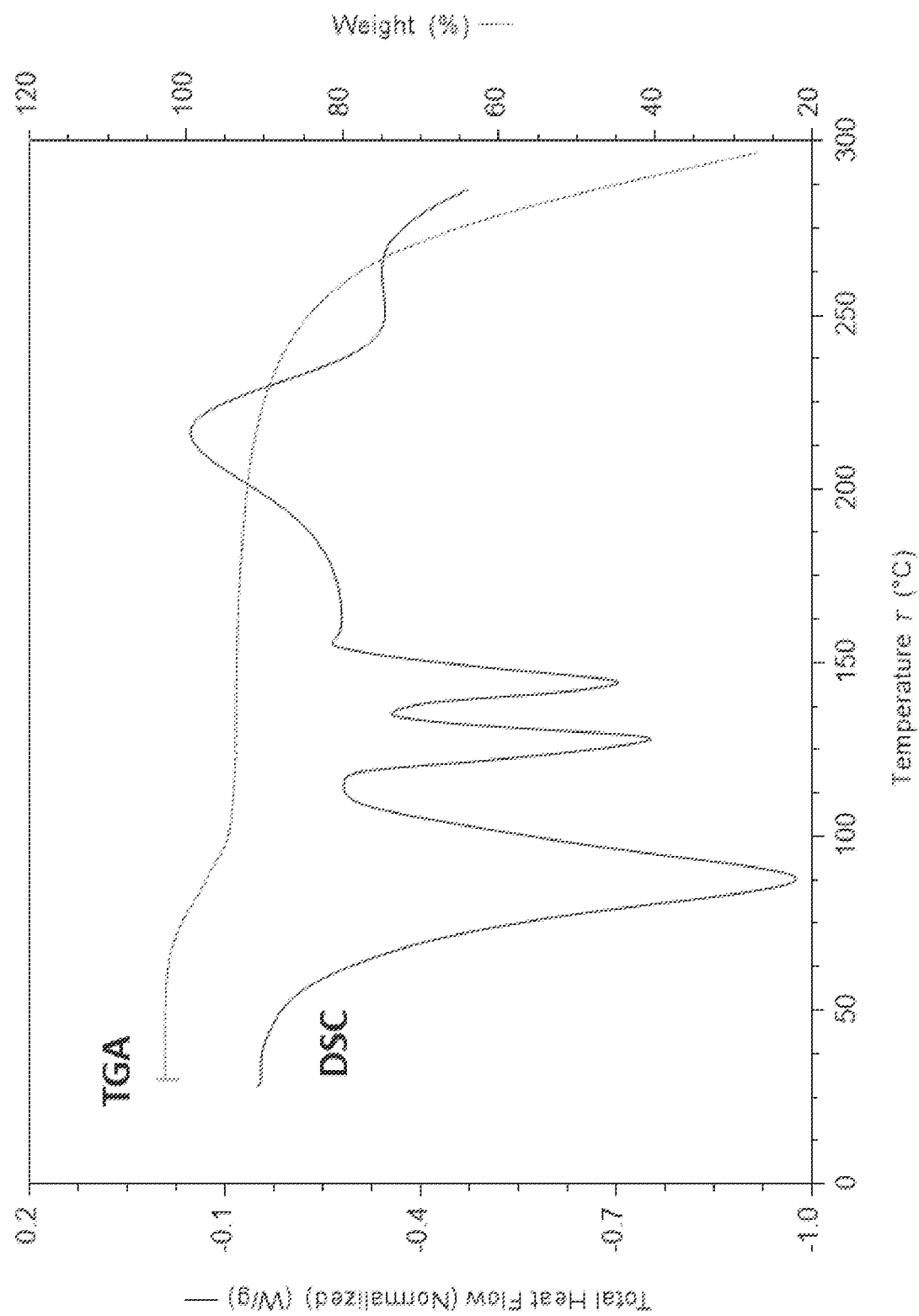
FIG. 19C shows DSC/TGA traces of the Form C ammonium salt of Compound 1.
Figure 19D:
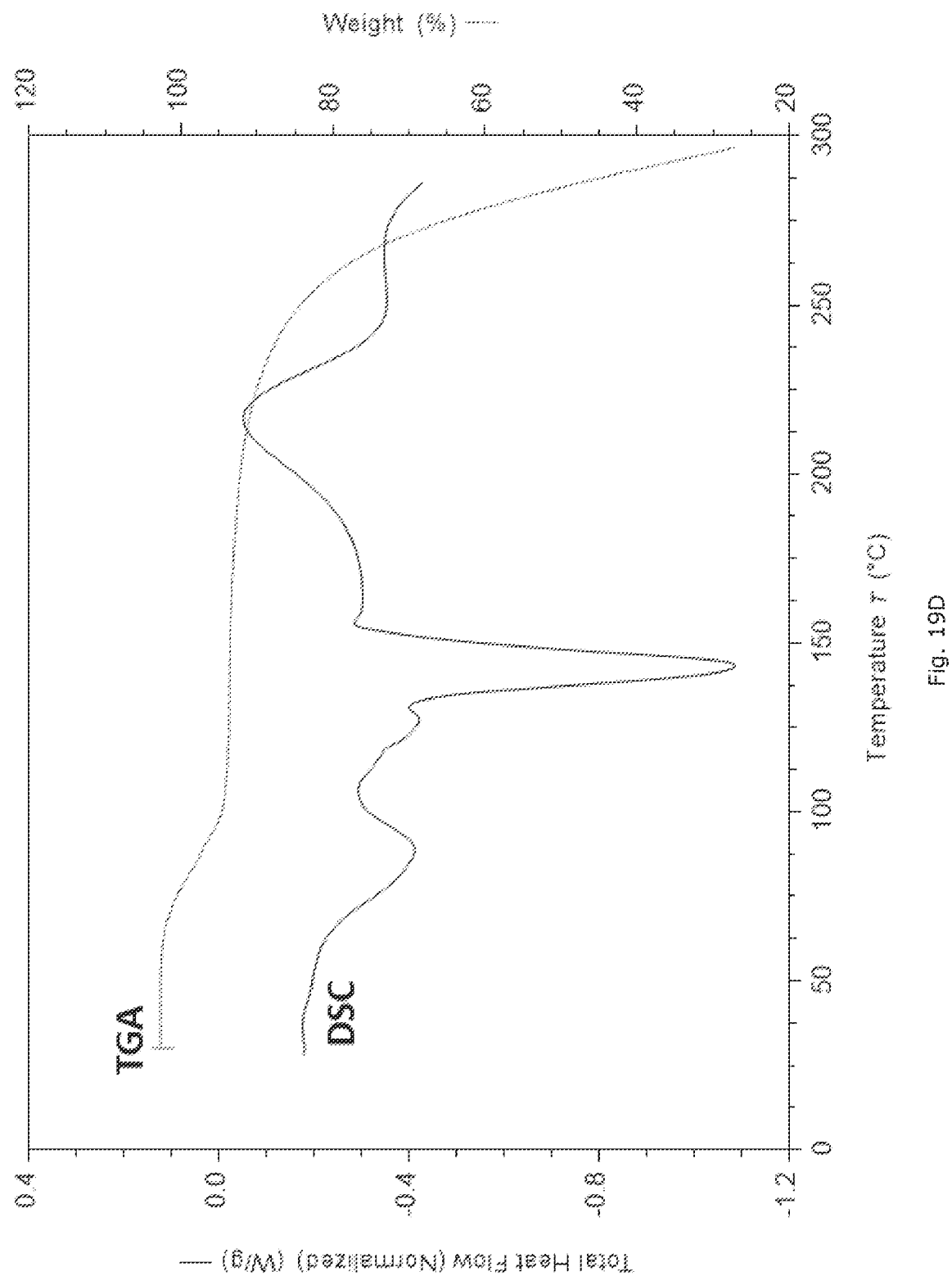
FIG. 19D shows DSC/TGA traces of the Form D ammonium salt of Compound 1.
Figure 21A:
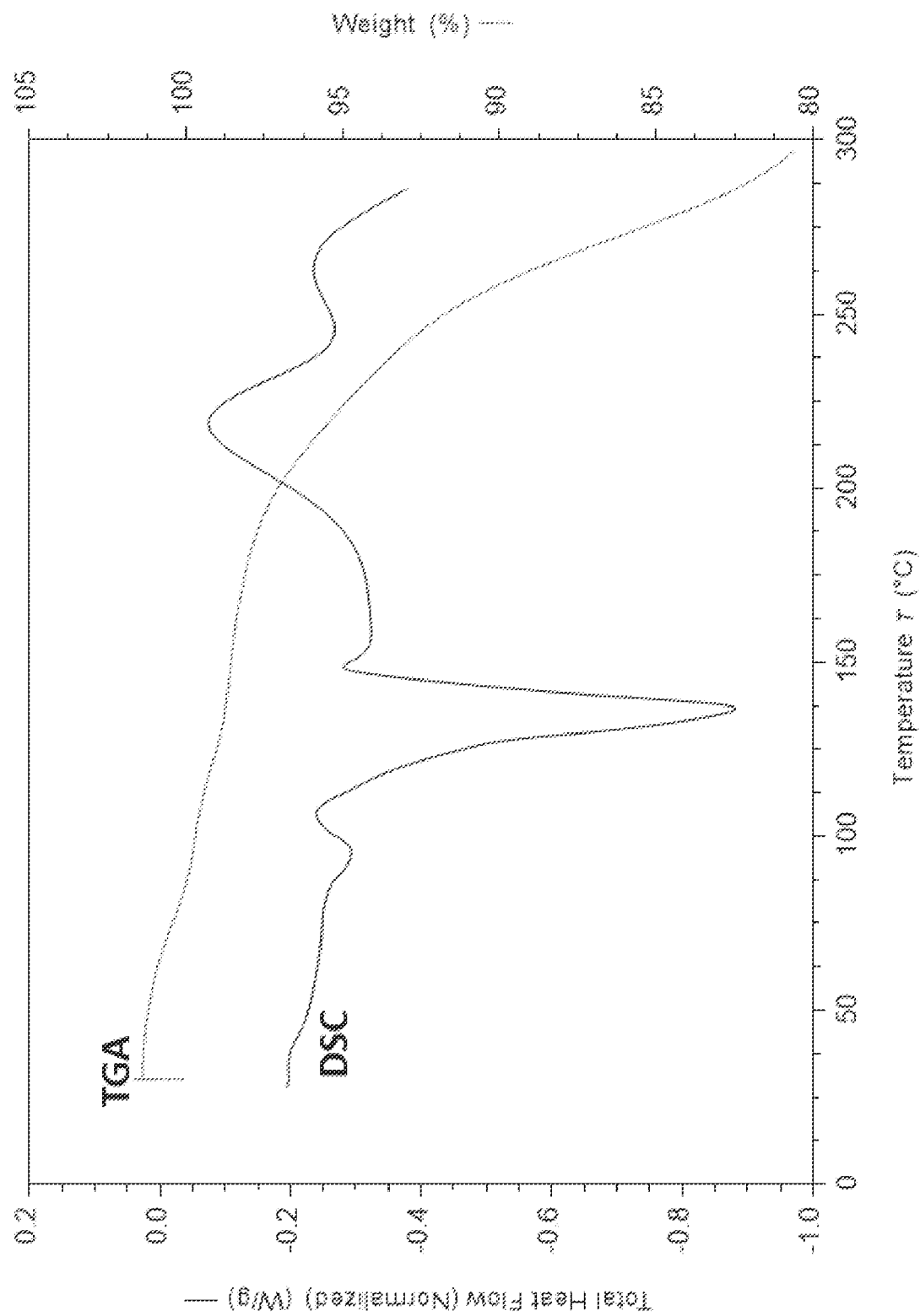
FIG. 21A shows DSC/TGA traces of the Form A magnesium salt of Compound 1.
Figure 21B:
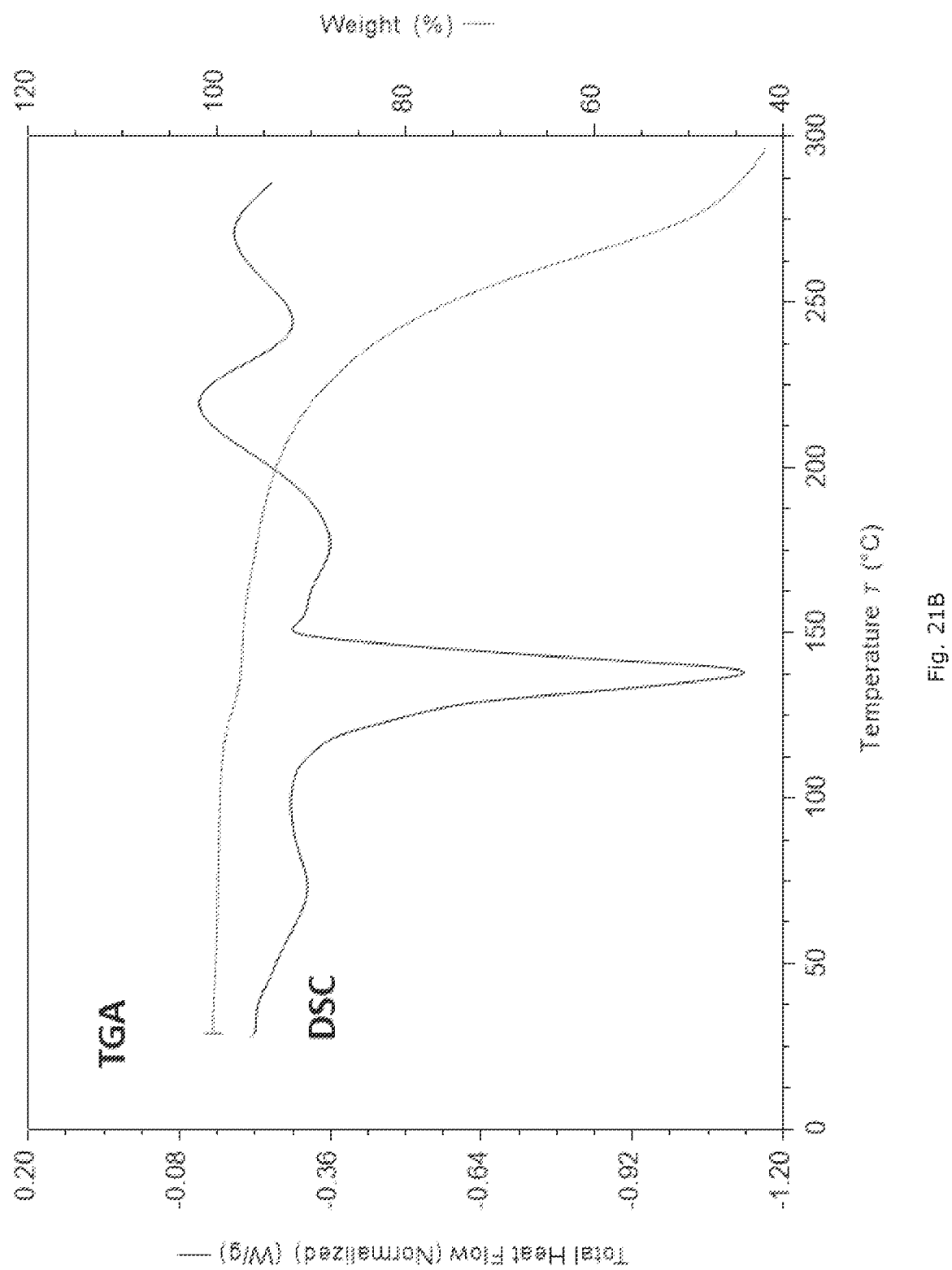
FIG. 21B shows DSC/TGA traces of the Form B magnesium salt of Compound 1.
Figure 23:
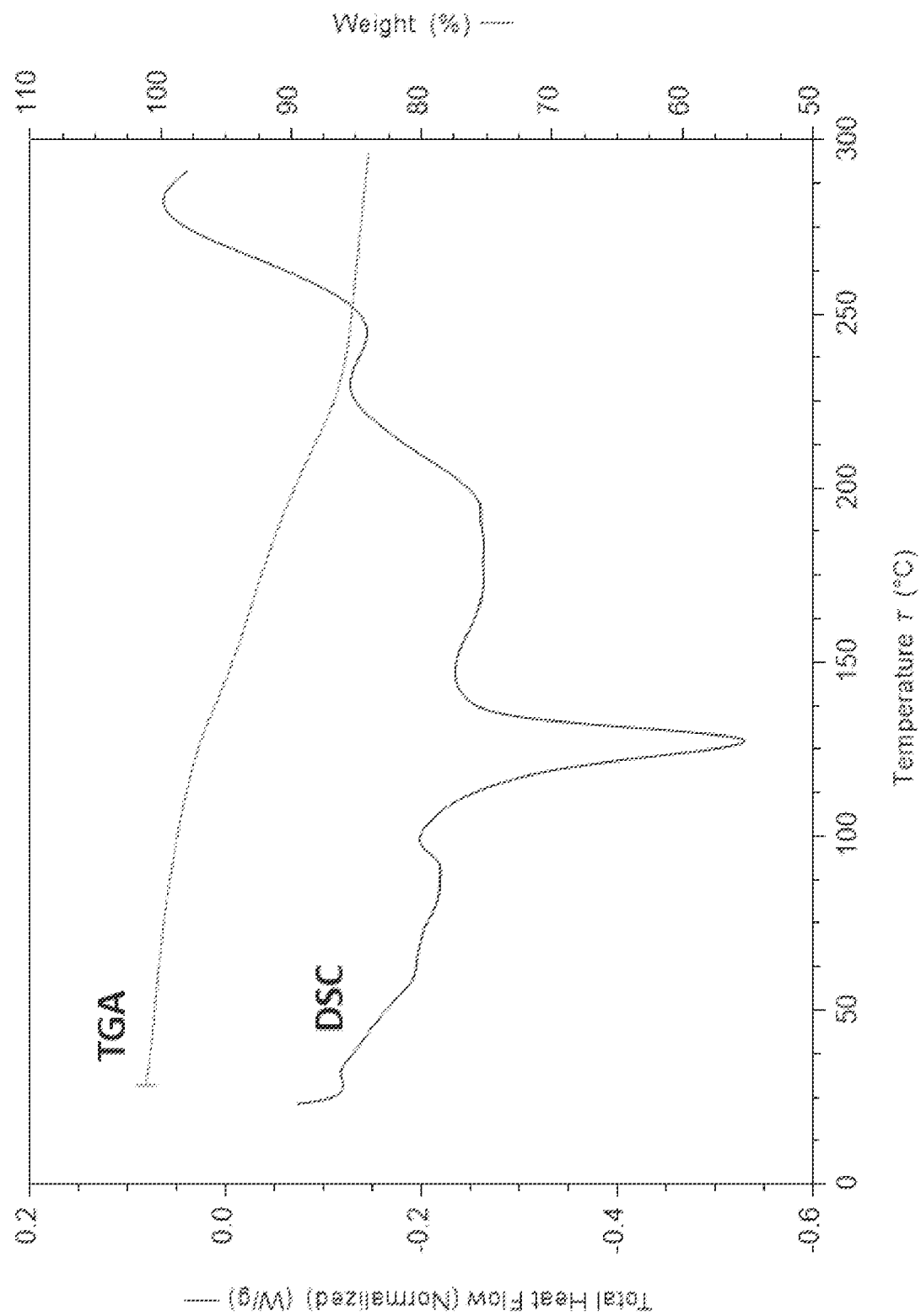
FIG. 23 shows DSC/TGA traces of the Form A calcium salt of Compound 1.

Example 5: Thermogravimetric analysis. A TA Instruments Discovery TGA instrument was used having the following parameters: ramp 10° C./minute; scan from 25 to 250° C.; and a 50 mL/minute $N_2$ sweep. Results are shown in FIG. 3 and FIG. 6.

Example 6: Polarized light microscopy. An Olympus BX51 polarized light microscope was used having the following parameters: a JENOPTIK ProgRes camera; and ProgRes Capture Pro 2.8.8 software.

Example 7: Kinetic Solubility. Kinetic solubility measurements were conducted on Compound 1 (a free acid) and Form A Tris salt of Compound 1 at 37° C. in water and three biorelevant media: synthetic gastric fluid; fed synthetic small intestinal fluid; and fasting synthetic small intestinal fluid. Results are shown in Table 1.

Example 8: Preparation of Form C Tris salt of Compound 1 and Form D Tris salt of Compound 1 (see FIG. 7, FIG. 8C, and FIG. 8D). Form C and Form D may be prepared analogous to preparing Form A, as described above, except 2-methyltetrahydrofuran is used as the solvent for Form C and methanol is used as the solvent for Form D. Form C may be a 2-MeTHF solvate and Form D may be a methanol solvate, both of which are converted to Form A by heating, for example, at 110° C.

Example 9: Salt Screening. 60 salt screening experiments were set up using 10 bases and six solvent systems. Specifically, about 50 mg starting free acid of Compound 1 and the corresponding base were mixed in 0.06-8.0 mL solvents with a molar charge ratio of 1:1 (except calcium and magnesium wherein a molar ratio of 2:1 was used). After magnetically stirring for 4 days at RT, any precipitation was isolated by centrifugation. If there was no precipitation, the clear solutions were transferred to stir at 5° C. to induce crystallization for 24 h. If still no solid, the final clear solutions were subjected to slow evaporation at RT. Any isolated solids were vacuum dried at 40° C. for 2 hrs before analysis. Crystalline salts were obtained as summarized in Table 7, namely Na salt Type A/B/C/D, K salt Type A/B/C/D/E, diethylamine salt Type A/B/C, TRIS salt Type A/B, Lysine salt Type A/B/C/D, ammonium salt Type A/B/C/D, Mg salt Type A/B and Ca Salt Type A/B/C as confirmed by XRPD, DSC and TGA; see FIGS. 7-23. Tris salt type C/D were prepared from 2-MeTHF and MeOH, respectively.

TABLE 7

| Acid | Solvent | | | | | |
|---|---|---|---|---|---|---|
| | MeOH A | Acetonitrile B | IPA C | THF D | EtOAc D | Acetone/H₂O (5:1, v/v) E |
| Blank | Free Acid Type A | Free Acid Type A | Free Acid Type A | Free Acid Type A | Free Acid Type A | Free Acid Type A |
| NaOH | Na salt Type A* | Na salt Type A | Na salt Type B | No solids | Na salt Type C# | Na Salt Type D# |
| KOH | K Salt Type C* | K salt Type A | K Salt Type D* | K salt Type B | No Solids Isolated* | K Salt Type E |
| Diethylamine (DEA) | DEA salt Type A* | DEA salt Type A | DEA salt Type C# | DEA salt Type B | DEA salt Type B | DEA salt Type B |
| TRIS | TRIS salt Type B# | TRIS salt Type A | TRIS salt Type B | TRIS salt Type B | TRIS salt Type B | TRIS salt Type B |
| Ammonium Acetate | No Solids isolated* | NH₄ salt Type A | NH₄ salt Type B | NH₄ salt Type C | NH₄ salt Type D | Free Acid + NH4 Type C |
| Lysine | Lysine salt Type A | Lysine salt Type B | Lysine salt Type C | Lysine salt Type D | Lysine salt Type D | Lysine salt Type D |
| Glycine | Free Acid Type A | Free Acid Type A | Glycine Type A | Free Acid Type A | Free Acid Type A# | Free Acid Type A |
| Mg(Ac)₂ | Mg salt Type A | Mg salt Type B | No Solids isolated* | No Solids isolated* | Free Acid + extra signals | Free Acid + extra signals |
| Choline | | | No solids isolated | | | |
| Ca(Ac)₂ | Ca salt Type A | Ca salt Type B# | Ca salt Type A + free acid | Ca salt Type A + free acid | Free Acid Type A* | Free Acid Type A | clear sample was observed after stirring at RT and solid was obtained via stirring at 5° C.
*solids were generated via evaporation at RT.

In some embodiments, the solid forms provided herein may be described by their respective XRPD signal patterns or portions thereof. For example, the solid forms may be described by one, two, three, four, or five, or more XRPD signals ±0.2° 2θ, wherein each signal is selected from those signals provided in a table herein corresponding to the solid form being described. In some embodiments, the signals used to describe the solid forms herein are selected from those signals herein having at least 100 cts. The XRPD signal pattern description of the solid forms herein may include about 5, 10, 20, 30, 40, 50, 60, 70, 80, 90, 95, or 100% of the signals included in a table of XRPD signals provided for the particular solid form being described, optionally wherein the table of XRPD signals is limited to those signals having at least 100 cts. In some embodiments, the signals used to describe the solid forms herein are selected from those signals herein having a relative intensity of at least about 0.25, 0.5, 1, 2, 3, 4, 5, 6, 7, 8, 9, 10, 15, or 20% relative intensity.

In some embodiments, the solid forms provided herein may be described by an XRPD signal pattern that includes an XRPD signal that is not within 0.2° 2θ of another solid form provided herein. For example, the solid form provided herein includes an XRPD signal at one or more of:
  2.59±0.2° 2θ (e.g., K Type C),
  5.12±0.2° 2θ (e.g., Lysine Type B),
  5.47±0.2° 2θ (e.g., Tris Type C),
  8.66±0.2° 2θ (e.g., Lysine Type A), or
  39.70±0.2° 2θ (e.g., Tris Type D).

In some embodiments, the solid forms provided herein may be described by an XRPD signal pattern that includes an XRPD signal that is not within 0.15° 2θ of another solid form provided herein. For example, the solid form provided herein includes an XRPD signal at one or more of:
  2.59±0.15° 2θ (e.g., K Type C),
  2.94±0.15° 2θ (e.g., Tris Type C),
  3.12±0.15° 2θ (e.g., Lysine Type B),
  4.57±0.15° 2θ (e.g., NH₄ Type C),
  4.73±0.15° 2θ (e.g., NH₄ Type A),
  5.12±0.15° 2θ (e.g., Lysine Type B),
  5.47±0.15° 2θ (e.g., Tris Type C),
  8.66±0.15° 2θ (e.g., Lysine Type A),
  26.65±0.15° 2θ (e.g., NH₄ Type A),
  35.21±0.15° 2θ (e.g., Tris Type A),
  35.71±0.15° 2θ (e.g., Na Type A),
  37.03±0.15° 2θ (e.g., Na Type B), or
  39.70±0.15° 2θ (e.g., Tris Type D).

In some embodiments, the solid forms provided herein may be described by an XRPD signal pattern that includes an XRPD signal that is not within 0.10° 2θ of another solid form provided herein. For example, the solid form provided herein includes an XRPD signal at one or more of:
  2.59±0.10° 2θ (e.g., K Type C),
  2.94±0.10° 2θ (e.g., Tris Type C),
  3.12±0.10° 2θ (e.g., Lysine Type B),
  4.57±0.10° 2θ (e.g., NH₄ Type C),
  4.73±0.10° 2θ (e.g., NH₄ Type A),
  5.12±0.10° 2θ (e.g., Lysine Type B),
  5.47±0.10° 2θ (e.g., Tris Type C),
  6.01±0.10° 2θ (e.g., NH₄ Type B),
  6.46±0.10° 2θ (e.g., Tris Type C),
  8.26±0.10° 2θ (e.g., Starting Material),
  8.66±0.10° 2θ (e.g., Lysine Type A),
  10.44±0.10° 2θ (e.g., Lysine Type D),
  12.16±0.10° 2θ (e.g., DEA Type C),
  12.65±0.10° 2θ (e.g., NH₄ Type D),
  14.39±0.10° 2θ (e.g., NH₄ Type D),
  24.95±0.10° 2θ (e.g., K Type E),
  26.65±0.10° 2θ (e.g., NH₄ Type A),
  30.63±0.10° 2θ (e.g., NH₄ Type D),
  32.84±0.10° 2θ (e.g., Tris Type B),
  33.95±0.10° 2θ (e.g., DEA Type B),
  34.07±0.10° 2θ (e.g., Tris Type B),
  35.21±0.10° 2θ (e.g., Tris Type A),
  35.71±0.10° 2θ (e.g., Na Type A),
  36.58±0.10° 2θ (e.g., Na Type C), 36.71±0.10° 2θ (e.g., Lysine Type D),
37.03±0.10° 2θ (e.g., Na Type B), or
39.70±0.10° 2θ (e.g., Tris Type D).

In some embodiments, the solid forms provided herein may be described by XRPD signal pattern that includes an XRPD signal that is not within 0.2° 2θ of another solid form provided herein when considering XRPD signals greater than 100 cts in height. For example, the solid form provided herein includes an XRPD signal at one or more of:
2.59±0.2° 2θ (e.g., K Type C),
5.12±0.2° 2θ (e.g., Lysine Type B),
5.47±0.2° 2θ (e.g., Tris Type C),
8.66±0.2° 2θ (e.g., Lysine Type A),
32.33±0.2° 2θ (e.g., Tris Type B),
34.07±0.2° 2θ (e.g., Tris Type B),
35.05±0.2° 2θ (e.g., Tris Type B),
36.41±0.2° 2θ (e.g., Starting Material),
37.61±0.2° 2θ (e.g., Tris Type D), or
39.70±0.2° 2θ (e.g., Tris Type D).

In some embodiments, the solid forms provided herein may be described by XRPD signal pattern that includes an XRPD signal that is not within 0.15° 2θ of another solid form provided herein when considering XRPD signals greater than 100 cts in height. For example, the solid form provided herein includes an XRPD signal at one or more of:
2.59±0.15° 2θ (e.g., K Type C),
2.94±0.15° 2θ (e.g., Tris Type C),
3.12±0.15° 2θ (e.g., Lysine Type B),
4.57±0.15° 2θ (e.g., NH$_4$ Type C),
4.73±0.15° 2θ (e.g., NH$_4$ Type A),
5.12±0.15° 2θ (e.g., Lysine Type B),
5.47±0.15° 2θ (e.g., Tris Type C),
8.45±0.15° 2θ (e.g., Tris Type C),
8.66±0.15° 2θ (e.g., Lysine Type A),
8.86±0.15° 2θ (e.g., Tris Type C),
32.33±0.15° 2θ (e.g., Tris Type B),
32.67±0.15° 2θ (e.g., Tris Type D),
32.84±0.15° 2θ (e.g., Tris Type B),
33.53±0.15° 2θ (e.g., Tris Type D),
34.07±0.15° 2θ (e.g., Tris Type B),
35.05±0.15° 2θ (e.g., Tris Type B),
36.41±0.15° 2θ (e.g., Starting Material),
37.61±0.15° 2θ (e.g., Tris Type D),
38.91±0.15° 2θ (e.g., Tris Type D), or
39.70±0.15° 2θ (e.g., Tris Type D).

In some embodiments, the solid forms provided herein may be described by XRPD signal pattern that includes an XRPD signal that is not within 0.10° 2θ of another solid form provided herein when considering XRPD signals greater than 100 cts in height. For example, the solid form provided herein includes an XRPD signal at one or more of:
2.59±0.10° 2θ (e.g., K Type C),
2.94±0.10° 2θ (e.g., Tris Type C),
3.12±0.10° 2θ (e.g., Lysine Type B),
4.57±0.10° 2θ (e.g., NH$_4$ Type C),
4.73±0.10° 2θ (e.g., NHa Type A),
5.12±0.10° 2θ (e.g., Lysine Type B),
5.47±0.10° 2θ (e.g., Tris Type C),
6.01±0.10° 2θ (e.g., NH$_4$ Type B),
6.46±0.10° 2θ (e.g., Tris Type C),
7.95±0.10° 2θ (e.g., NH$_4$ Type B),
8.11±0.10° 2θ (e.g., DEA Type C),
8.26±0.10° 2θ (e.g., Starting Material),
8.45±0.10° 2θ (e.g., Tris Type C),
8.66±0.10° 2θ (e.g., Lysine Type A),
8.86±0.10° 2θ (e.g., Tris Type C),
10.43±0.10° 2θ (e.g., Lysine Type D),
12.16±0.10° 2θ (e.g., DEA Type C),
12.65±0.10° 2θ (e.g., NH$_4$ Type D),
14.39±0.10° 2θ (e.g., NH$_4$ Type D),
24.95±0.10° 2θ (e.g., K Type E),
26.21±0.10° 2θ (e.g., NH$_4$ Type A),
28.18±0.10° 2θ (e.g., NH$_4$ Type D),
28.92±0.10° 2θ (e.g., Tris Type C),
29.04±0.10° 2θ (e.g., Tris Type B),
29.83±0.10° 2θ (e.g., Tris Type C),
29.97±0.10° 2θ (e.g., Tris Type D),
32.34±0.10° 2θ (e.g., Tris Type B),
32.67±0.10° 2θ (e.g., Tris Type D),
32.84±0.10° 2θ (e.g., Tris Type B),
33.53±0.10° 2θ (e.g., Tris Type D),
34.07±0.10° 2θ (e.g., Tris Type B),
35.05±0.10° 2θ (e.g., Tris Type B),
36.41±0.10° 2θ (e.g., Starting Material),
37.61±0.10° 2θ (e.g., Tris Type D),
38.91±0.10° 2θ (e.g., Tris Type D),
39.26±0.10° 2θ (e.g., Tris Type D), or
39.70±0.10° 2θ (e.g., Tris Type D).

Tables 8-37 provide lists of signals, height, and relative intensities for certain of the XRPD signal patterns of solid forms identified in Table 7.

TABLE 8

Observed XRPD signals and relative intensities of free acid Type A solid form identified in Table 7.

| No. | Pos. [°2θ] ± 0.2 | Height [cts] | Relative Intensity |
|---|---|---|---|
| 1 | 4.15 | 1112.24 | 20.94% |
| 2 | 5.88 | 280.26 | 5.28% |
| 3 | 6.80 | 35.22 | 0.66% |
| 4 | 8.26 | 812.46 | 15.30% |
| 5 | 9.88 | 2160.76 | 40.69% |
| 6 | 10.90 | 2342.58 | 44.11% |
| 7 | 11.12 | 3003.95 | 56.56% |
| 8 | 11.65 | 5310.79 | 100.00% |
| 9 | 13.47 | 857.16 | 16.14% |
| 10 | 14.99 | 636.78 | 11.99% |
| 11 | 15.72 | 1484.81 | 27.96% |
| 12 | 16.13 | 306.01 | 5.76% |
| 13 | 16.49 | 555.48 | 10.46% |
| 14 | 16.78 | 683.45 | 12.87% |
| 15 | 17.84 | 1607.22 | 30.26% |
| 16 | 18.03 | 2299.22 | 43.29% |
| 17 | 18.35 | 1645.47 | 30.98% |
| 18 | 18.68 | 1383.24 | 26.05% |
| 19 | 19.23 | 1763.46 | 33.21% |
| 20 | 19.72 | 2842.99 | 53.53% |
| 21 | 20.50 | 1401.77 | 26.39% |
| 22 | 21.47 | 500.17 | 9.42% |
| 23 | 21.91 | 376.44 | 7.09% |
| 24 | 22.23 | 687.68 | 12.95% |
| 25 | 22.78 | 338.26 | 6.37% |
| 26 | 23.25 | 1732.95 | 32.63% |
| 27 | 24.26 | 486.83 | 9.17% |
| 28 | 24.73 | 547.19 | 10.30% |
| 29 | 25.24 | 325.80 | 6.13% |
| 30 | 26.32 | 525.11 | 9.89% |
| 31 | 27.03 | 112.55 | 2.12% |
| 32 | 27.55 | 392.24 | 7.39% |
| 33 | 27.98 | 344.06 | 6.48% |
| 34 | 28.65 | 64.77 | 1.22% |
| 35 | 29.20 | 142.60 | 2.69% |
| 36 | 29.67 | 72.43 | 1.36% |
| 37 | 30.16 | 121.07 | 2.28% |
| 38 | 31.11 | 280.08 | 5.27% |
| 39 | 31.66 | 147.34 | 2.77% |
| 40 | 32.28 | 51.68 | 0.97% |
| 41 | 33.15 | 223.95 | 4.22% |
| 42 | 34.37 | 68.67 | 1.29% |

TABLE 8-continued

Observed XRPD signals and relative intensities of free acid Type A solid form identified in Table 7.

| No. | Pos. [°2θ] ± 0.2 | Height [cts] | Relative Intensity |
|---|---|---|---|
| 43 | 34.89 | 72.46 | 1.36% |
| 44 | 36.41 | 125.70 | 2.37% |
| 45 | 38.22 | 116.99 | 2.20% |
| 46 | 39.08 | 101.59 | 1.91% |

TABLE 9

Observed XRPD signals and relative intensities of Tris Type A solid form identified in Table 7.

| No. | Pos. [°2θ] ± 0.2 | Height [cts] | Relative Intensity |
|---|---|---|---|
| 1 | 3.75 | 2691.73 | 89.13% |
| 2 | 7.52 | 2170.21 | 71.86% |
| 3 | 9.48 | 354.45 | 11.74% |
| 4 | 10.03 | 253.05 | 8.38% |
| 5 | 11.30 | 8523.70 | 282.25% |
| 6 | 11.99 | 1237.47 | 40.98% |
| 7 | 14.62 | 562.77 | 18.64% |
| 8 | 15.10 | 1430.73 | 47.38% |
| 9 | 15.50 | 1320.66 | 43.73% |
| 10 | 16.17 | 295.34 | 9.78% |
| 11 | 17.28 | 1289.68 | 42.71% |
| 12 | 17.59 | 1193.00 | 39.50% |
| 13 | 18.10 | 2130.38 | 70.54% |
| 14 | 18.67 | 1287.28 | 42.63% |
| 15 | 19.05 | 426.03 | 14.11% |
| 16 | 19.63 | 3019.93 | 100.00% |
| 17 | 20.16 | 924.96 | 30.63% |
| 18 | 20.62 | 187.71 | 6.22% |
| 19 | 21.09 | 521.06 | 17.25% |
| 20 | 21.71 | 78.11 | 2.59% |
| 21 | 22.36 | 89.21 | 2.95% |
| 22 | 22.75 | 1083.96 | 35.89% |
| 23 | 23.72 | 525.07 | 17.39% |
| 24 | 24.27 | 313.19 | 10.37% |
| 25 | 24.62 | 330.74 | 10.95% |
| 26 | 25.49 | 207.77 | 6.88% |
| 27 | 26.42 | 14.37 | 0.48% |
| 28 | 27.14 | 140.23 | 4.64% |
| 29 | 28.41 | 313.89 | 10.39% |
| 30 | 29.28 | 107.12 | 3.55% |
| 31 | 30.16 | 99.01 | 3.28% |
| 32 | 30.79 | 122.95 | 4.07% |
| 33 | 31.81 | 164.27 | 5.44% |
| 34 | 33.05 | 40.19 | 1.33% |
| 35 | 33.49 | 69.52 | 2.30% |
| 36 | 33.83 | 87.72 | 2.90% |
| 37 | 34.32 | 44.79 | 1.48% |
| 38 | 35.21 | 53.06 | 1.76% |
| 39 | 37.45 | 74.67 | 2.47% |

TABLE 10

Observed XRPD signals and relative intensities of Tris Type B solid form identified in Table 7.

| No. | Pos. [°2θ] ± 0.2 | Height [cts] | Relative Intensity |
|---|---|---|---|
| 1 | 3.87 | 5099.14 | 20.63% |
| 2 | 7.70 | 3937.12 | 15.93% |
| 3 | 8.87 | 92.36 | 0.37% |
| 4 | 9.59 | 521.66 | 2.11% |
| 5 | 11.55 | 24721.42 | 100.00% |

TABLE 10-continued

Observed XRPD signals and relative intensities of Tris Type B solid form identified in Table 7.

| No. | Pos. [°2θ] ± 0.2 | Height [cts] | Relative Intensity |
|---|---|---|---|
| 6 | 12.49 | 281.58 | 1.14% |
| 7 | 13.35 | 71.72 | 0.29% |
| 8 | 14.51 | 1888.61 | 7.64% |
| 9 | 15.05 | 1629.27 | 6.59% |
| 10 | 15.41 | 2140.39 | 8.66% |
| 11 | 16.01 | 4163.15 | 16.84% |
| 12 | 17.02 | 404.50 | 1.64% |
| 13 | 17.45 | 1154.54 | 4.67% |
| 14 | 17.77 | 1095.89 | 4.43% |
| 15 | 18.28 | 6171.72 | 24.97% |
| 16 | 18.51 | 955.25 | 3.86% |
| 17 | 19.33 | 1677.98 | 6.79% |
| 18 | 19.84 | 6106.30 | 24.70% |
| 19 | 20.30 | 302.78 | 1.22% |
| 20 | 21.07 | 776.82 | 3.14% |
| 21 | 21.93 | 961.28 | 3.89% |
| 22 | 23.19 | 5207.87 | 21.07% |
| 23 | 23.86 | 434.67 | 1.76% |
| 24 | 25.10 | 415.76 | 1.68% |
| 25 | 26.04 | 175.55 | 0.71% |
| 26 | 26.86 | 598.63 | 2.42% |
| 27 | 27.56 | 538.94 | 2.18% |
| 28 | 29.04 | 237.35 | 0.96% |
| 29 | 29.43 | 225.79 | 0.91% |
| 30 | 30.44 | 266.15 | 1.08% |
| 31 | 31.06 | 276.26 | 1.12% |
| 32 | 31.62 | 281.56 | 1.14% |
| 33 | 32.34 | 267.70 | 1.08% |
| 34 | 32.84 | 123.36 | 0.50% |
| 35 | 34.07 | 210.45 | 0.85% |
| 36 | 34.41 | 206.11 | 0.83% |
| 37 | 35.05 | 169.00 | 0.68% |
| 38 | 35.90 | 157.35 | 0.64% |
| 39 | 37.50 | 71.33 | 0.29% |
| 40 | 38.27 | 124.93 | 0.51% |
| 41 | 38.89 | 65.05 | 0.26% |
| 42 | 39.41 | 65.39 | 0.26% |

TABLE 11

Observed XRPD signals and relative intensities of Tris Type C solid form identified in Table 7.

| No. | Pos. [°2θ] ± 0.2 | Height [cts] | Relative Intensity |
|---|---|---|---|
| 1 | 2.94 | 5777.76 | 86.22% |
| 2 | 5.47 | 6075.21 | 90.65% |
| 3 | 5.89 | 6701.57 | 100.00% |
| 4 | 6.46 | 2113.91 | 31.54% |
| 5 | 8.45 | 933.26 | 13.93% |
| 6 | 8.86 | 861.55 | 12.86% |
| 7 | 9.96 | 6086.56 | 90.82% |
| 8 | 10.90 | 4301.50 | 64.19% |
| 9 | 11.11 | 2434.40 | 36.33% |
| 10 | 11.53 | 475.86 | 7.10% |
| 11 | 12.54 | 2929.91 | 43.72% |
| 12 | 13.50 | 987.67 | 14.74% |
| 13 | 14.81 | 534.20 | 7.97% |
| 14 | 15.30 | 2884.43 | 43.04% |
| 15 | 16.52 | 4401.03 | 65.67% |
| 16 | 16.96 | 1323.54 | 19.75% |
| 17 | 17.56 | 3005.88 | 44.85% |
| 18 | 18.04 | 946.22 | 14.12% |
| 19 | 18.71 | 490.92 | 7.33% |
| 20 | 19.30 | 737.96 | 11.01% |
| 21 | 19.98 | 2891.52 | 43.15% |
| 22 | 21.10 | 1427.56 | 21.30% |
| 23 | 22.01 | 1396.34 | 20.84% |

TABLE 11-continued

Observed XRPD signals and relative intensities of
Tris Type C solid form identified in Table 7.

| No. | Pos. [°2θ] ± 0.2 | Height [cts] | Relative Intensity |
|---|---|---|---|
| 24 | 22.29 | 1832.08 | 27.34% |
| 25 | 22.55 | 1223.69 | 18.26% |
| 26 | 23.09 | 329.21 | 4.91% |
| 27 | 23.44 | 569.14 | 8.49% |
| 28 | 23.87 | 912.81 | 13.62% |
| 29 | 25.40 | 322.87 | 4.82% |
| 30 | 26.81 | 550.69 | 8.22% |
| 31 | 27.73 | 376.51 | 5.62% |
| 32 | 27.98 | 265.93 | 3.97% |
| 33 | 28.92 | 242.01 | 3.61% |
| 34 | 29.83 | 168.43 | 2.51% |
| 35 | 30.17 | 243.65 | 3.64% |
| 36 | 30.87 | 127.95 | 1.91% |
| 37 | 31.56 | 93.82 | 1.40% |
| 38 | 33.24 | 151.96 | 2.27% |
| 39 | 33.74 | 101.76 | 1.52% |
| 40 | 34.56 | 68.47 | 1.02% |
| 41 | 37.43 | 55.54 | 0.83% |
| 42 | 39.33 | 84.36 | 1.26% |

TABLE 12

Observed XRPD signals and relative intensities of
Tris Type D solid form identified in Table 7.

| No. | Pos. [°2θ] ± 0.2 | Height [cts] | Relative Intensity |
|---|---|---|---|
| 1 | 3.93 | 7760.81 | 62.92% |
| 2 | 7.85 | 1525.58 | 12.37% |
| 3 | 10.67 | 1346.42 | 10.92% |
| 4 | 11.79 | 12334.99 | 100.00% |
| 5 | 12.96 | 2924.14 | 23.71% |
| 6 | 13.33 | 1454.24 | 11.79% |
| 7 | 14.56 | 1750.94 | 14.19% |
| 8 | 15.09 | 203.53 | 1.65% |
| 9 | 15.71 | 632.80 | 5.13% |
| 10 | 16.08 | 2718.37 | 22.04% |
| 11 | 16.65 | 632.08 | 5.12% |
| 12 | 17.60 | 4359.12 | 35.34% |
| 13 | 18.34 | 1939.67 | 15.72% |
| 14 | 19.06 | 1027.41 | 8.33% |
| 15 | 19.52 | 2109.92 | 17.11% |
| 16 | 19.65 | 2397.96 | 19.44% |
| 17 | 20.05 | 505.87 | 4.10% |
| 18 | 20.84 | 1075.47 | 8.72% |
| 19 | 21.39 | 2055.49 | 16.66% |
| 20 | 21.72 | 781.56 | 6.34% |
| 21 | 22.74 | 1029.95 | 8.35% |
| 22 | 23.23 | 734.22 | 5.95% |
| 23 | 23.68 | 1296.42 | 10.51% |
| 24 | 24.10 | 2183.08 | 17.70% |
| 25 | 25.67 | 196.57 | 1.59% |
| 26 | 26.06 | 183.49 | 1.49% |
| 27 | 26.33 | 136.22 | 1.10% |
| 28 | 27.19 | 1109.15 | 8.99% |
| 29 | 27.70 | 743.40 | 6.03% |
| 30 | 28.47 | 215.27 | 1.75% |
| 31 | 29.36 | 201.66 | 1.63% |
| 32 | 29.97 | 443.62 | 3.60% |
| 33 | 30.42 | 421.52 | 3.42% |
| 34 | 31.17 | 683.64 | 5.54% |
| 35 | 31.75 | 444.25 | 3.60% |
| 36 | 32.67 | 317.23 | 2.57% |
| 37 | 33.53 | 118.37 | 0.96% |
| 38 | 34.42 | 571.07 | 4.63% |
| 39 | 35.95 | 215.22 | 1.74% |
| 40 | 37.19 | 152.24 | 1.23% |
| 41 | 37.61 | 172.89 | 1.40% |
| 42 | 38.15 | 100.17 | 0.81% |
| 43 | 38.91 | 130.68 | 1.06% |
| 44 | 39.26 | 117.34 | 0.95% |
| 45 | 39.70 | 110.40 | 0.90% |

TABLE 13

Observed XRPD signals and relative intensities of
Tris Type E solid form identified in Table 7.

| No. | Pos. [°2θ] ± 0.2 | Height [cts] | Relative Intensity |
|---|---|---|---|
| 1 | 3.60 | 426.06 | 17.64% |
| 2 | 7.19 | 152.75 | 6.32% |
| 3 | 14.23 | 2415.67 | 100.00% |
| 4 | 17.61 | 161.34 | 6.68% |
| 5 | 18.22 | 223.69 | 9.26% |
| 6 | 20.18 | 1676.40 | 69.40% |
| 7 | 21.59 | 33.24 | 1.38% |
| 8 | 22.54 | 622.77 | 25.78% |
| 9 | 28.65 | 61.37 | 2.54% |
| 10 | 37.19 | 134.09 | 5.55% |

TABLE 14

Observed XRPD signals and relative intensities
of Na Type A solid form identified in Table 7.

| No. | Pos. [°2θ] ± 0.2 | Height [cts] | Relative Intensity |
|---|---|---|---|
| 1 | 3.93 | 120.49 | 1.67% |
| 2 | 7.82 | 215.83 | 3.00% |
| 3 | 9.09 | 131.66 | 1.83% |
| 4 | 10.63 | 926.69 | 12.88% |
| 5 | 11.73 | 7197.32 | 100.00% |
| 6 | 13.19 | 554.63 | 7.71% |
| 7 | 15.22 | 128.99 | 1.79% |
| 8 | 15.68 | 907.37 | 12.61% |
| 9 | 17.71 | 347.01 | 4.82% |
| 10 | 18.07 | 140.20 | 1.95% |
| 11 | 18.55 | 828.47 | 11.51% |
| 12 | 19.61 | 677.64 | 9.42% |
| 13 | 20.16 | 568.51 | 7.90% |
| 14 | 20.86 | 206.84 | 2.87% |
| 15 | 21.16 | 191.31 | 2.66% |
| 16 | 22.63 | 91.38 | 1.27% |
| 17 | 23.56 | 453.31 | 6.30% |
| 18 | 24.70 | 83.04 | 1.15% |
| 19 | 26.24 | 50.59 | 0.70% |
| 20 | 31.97 | 34.34 | 0.48% |
| 21 | 32.48 | 44.41 | 0.62% |
| 22 | 34.69 | 20.71 | 0.29% |
| 23 | 35.71 | 26.32 | 0.37% |
| 24 | 36.47 | 33.81 | 0.47% |

TABLE 15

Observed XRPD signals and relative intensities of Na Type B solid form identified in Table 7.

| No. | Pos. [°2θ] ± 0.2 | Height [cts] | Relative Intensity |
|---|---|---|---|
| 1 | 3.75 | 346.70 | 2.02% |
| 2 | 5.72 | 17155.10 | 100.00% |
| 3 | 6.65 | 437.03 | 2.55% |
| 4 | 7.86 | 68.41 | 0.40% |
| 5 | 9.89 | 7204.15 | 41.99% |
| 6 | 10.75 | 2874.15 | 16.75% |
| 7 | 11.44 | 8624.33 | 50.27% |
| 8 | 12.47 | 78.35 | 0.46% |
| 9 | 13.30 | 436.67 | 2.55% |
| 10 | 14.22 | 51.50 | 0.30% |
| 11 | 14.89 | 512.06 | 2.98% |
| 12 | 15.90 | 483.55 | 2.82% |
| 13 | 16.88 | 215.66 | 1.26% |
| 14 | 17.19 | 690.51 | 4.03% |
| 15 | 17.43 | 692.77 | 4.04% |
| 16 | 17.90 | 574.29 | 3.35% |
| 17 | 18.55 | 130.75 | 0.76% |
| 18 | 19.12 | 350.33 | 2.04% |
| 19 | 19.83 | 1690.33 | 9.85% |
| 20 | 20.37 | 1996.83 | 11.64% |
| 21 | 20.71 | 346.43 | 2.02% |
| 22 | 21.50 | 391.82 | 2.28% |
| 23 | 22.04 | 331.61 | 1.93% |
| 24 | 23.08 | 495.57 | 2.89% |
| 25 | 24.17 | 210.24 | 1.23% |
| 26 | 24.65 | 63.08 | 0.37% |
| 27 | 25.49 | 297.85 | 1.74% |
| 28 | 26.00 | 1780.65 | 10.38% |
| 29 | 26.90 | 96.23 | 0.56% |
| 30 | 28.43 | 149.32 | 0.87% |
| 31 | 30.11 | 103.68 | 0.60% |
| 32 | 31.00 | 41.39 | 0.24% |
| 33 | 31.76 | 292.69 | 1.71% |
| 34 | 32.58 | 28.10 | 0.16% |
| 35 | 33.22 | 53.16 | 0.31% |
| 36 | 34.22 | 35.44 | 0.21% |
| 37 | 34.96 | 47.37 | 0.28% |
| 38 | 37.03 | 29.57 | 0.17% |
| 39 | 37.59 | 97.34 | 0.57% |

TABLE 16

Observed XRPD signals and relative intensities of Na Type C solid form identified in Table 7.

| No. | Pos. [°2θ] ± 0.2 | Height [cts] | Relative Intensity |
|---|---|---|---|
| 1 | 3.35 | 2453.80 | 56.45% |
| 2 | 5.72 | 52.15 | 1.20% |
| 3 | 9.06 | 386.25 | 8.89% |
| 4 | 10.63 | 1457.04 | 33.52% |
| 5 | 11.79 | 4347.12 | 100.00% |
| 6 | 13.21 | 517.09 | 11.90% |
| 7 | 15.23 | 629.31 | 14.48% |
| 8 | 16.22 | 777.47 | 17.88% |
| 9 | 17.96 | 1377.23 | 31.68% |
| 10 | 19.22 | 1129.31 | 25.98% |
| 11 | 19.69 | 626.44 | 14.41% |
| 12 | 20.83 | 242.45 | 5.58% |
| 13 | 21.17 | 418.94 | 9.64% |
| 14 | 21.66 | 172.47 | 3.97% |
| 15 | 23.42 | 296.61 | 6.82% |
| 16 | 23.68 | 328.04 | 7.55% |
| 17 | 25.36 | 89.32 | 2.05% |
| 18 | 26.49 | 82.86 | 1.91% |
| 19 | 27.28 | 86.59 | 1.99% |
| 20 | 31.84 | 55.89 | 1.29% |
| 21 | 36.58 | 20.49 | 0.47% |

TABLE 17

Observed XRPD signals and relative intensities of Na Type D solid form identified in Table 7.

| No. | Pos. [°2θ] ± 0.2 | Height [cts] | Relative Intensity |
|---|---|---|---|
| 1 | 3.70 | 4322.91 | 27.48% |
| 2 | 7.36 | 4123.68 | 26.22% |
| 3 | 7.66 | 1441.57 | 9.16% |
| 4 | 9.17 | 826.58 | 5.25% |
| 5 | 10.57 | 1206.82 | 7.67% |
| 6 | 11.03 | 9332.42 | 59.33% |
| 7 | 11.53 | 15729.57 | 100.00% |
| 8 | 12.99 | 276.03 | 1.75% |
| 9 | 14.70 | 1273.03 | 8.09% |
| 10 | 15.52 | 432.88 | 2.75% |
| 11 | 16.66 | 102.30 | 0.65% |
| 12 | 17.60 | 258.62 | 1.64% |
| 13 | 18.09 | 656.37 | 4.17% |
| 14 | 18.42 | 374.23 | 2.38% |
| 15 | 19.31 | 1237.70 | 7.87% |
| 16 | 19.93 | 272.29 | 1.73% |
| 17 | 20.85 | 176.39 | 1.12% |
| 18 | 22.10 | 1374.28 | 8.74% |
| 19 | 23.21 | 1179.88 | 7.50% |
| 20 | 27.32 | 83.40 | 0.53% |
| 21 | 27.75 | 102.26 | 0.65% |
| 22 | 34.42 | 32.13 | 0.20% |

TABLE 18

Observed XRPD signals and relative intensities of K Type A solid form identified in Table 7.

| No. | Pos. [°2θ] ± 0.2 | Height [cts] | Relative Intensity |
|---|---|---|---|
| 1 | 11.48 | 983.26 | 100.00% |
| 2 | 14.98 | 95.93 | 9.76% |
| 3 | 15.36 | 71.85 | 7.31% |
| 4 | 15.95 | 60.19 | 6.12% |
| 5 | 17.40 | 80.27 | 8.16% |
| 6 | 18.25 | 257.70 | 26.21% |
| 7 | 19.31 | 147.54 | 15.01% |
| 8 | 19.82 | 218.64 | 22.24% |
| 9 | 21.94 | 32.89 | 3.34% |
| 10 | 23.24 | 386.45 | 39.30% |

TABLE 19

Observed XRPD signals and relative intensities of K Type B solid form identified in Table 7.

| No. | Pos. [°2θ] ± 0.2 | Height [cts] | Relative Intensity |
|---|---|---|---|
| 1 | 5.77 | 168.35 | 67.89% |
| 2 | 7.18 | 107.56 | 43.38% |

TABLE 19-continued

Observed XRPD signals and relative intensities of K Type B solid form identified in Table 7.

| No. | Pos. [°2θ] ± 0.2 | Height [cts] | Relative Intensity |
|---|---|---|---|
| 3 | 11.29 | 137.96 | 55.64% |
| 4 | 13.50 | 20.34 | 8.20% |
| 5 | 17.04 | 95.35 | 38.45% |
| 6 | 17.45 | 123.14 | 49.66% |
| 7 | 18.84 | 24.54 | 9.90% |
| 8 | 21.13 | 42.47 | 17.13% |
| 9 | 21.74 | 89.37 | 36.04% |
| 10 | 22.73 | 247.97 | 100.00% |
| 11 | 25.77 | 120.55 | 48.61% |
| 12 | 39.06 | 244.02 | 98.41% |

TABLE 20

Observed XRPD signals and relative intensities of K Type C solid form identified in Table 7.

| No. | Pos. [°2θ] ± 0.2 | Height [cts] | Relative Intensity |
|---|---|---|---|
| 1 | 2.59 | 129.65 | 30.86% |
| 2 | 3.45 | 420.18 | 100.00% |
| 3 | 9.90 | 61.35 | 14.60% |
| 4 | 11.83 | 408.29 | 97.17% |
| 5 | 13.09 | 123.80 | 29.46% |
| 6 | 13.71 | 131.97 | 31.41% |
| 7 | 14.96 | 139.72 | 33.25% |
| 8 | 16.22 | 65.40 | 15.56% |
| 9 | 17.14 | 135.80 | 32.32% |
| 10 | 17.82 | 231.61 | 55.12% |
| 11 | 18.56 | 102.00 | 24.28% |
| 12 | 19.65 | 109.88 | 26.15% |
| 13 | 20.19 | 86.38 | 20.56% |
| 14 | 23.63 | 157.85 | 37.57% |
| 15 | 24.39 | 41.75 | 9.94% |
| 16 | 25.14 | 31.61 | 7.52% |
| 17 | 30.25 | 78.81 | 18.76% |
| 18 | 31.65 | 88.30 | 21.01% |

TABLE 21

Observed XRPD signals and relative intensities of K Type D solid form identified in Table 7.

| No. | Pos. [°2θ] ± 0.2 | Height [cts] | Relative Intensity |
|---|---|---|---|
| 1 | 3.53 | 274.82 | 77.60% |
| 2 | 5.71 | 186.57 | 52.68% |
| 3 | 7.27 | 211.79 | 59.81% |
| 4 | 9.86 | 77.45 | 21.87% |
| 5 | 10.95 | 175.56 | 49.58% |
| 6 | 11.33 | 105.08 | 29.67% |
| 7 | 12.91 | 148.73 | 42.00% |
| 8 | 14.07 | 37.45 | 10.58% |
| 9 | 15.79 | 320.36 | 90.46% |
| 10 | 16.26 | 214.87 | 60.68% |
| 11 | 17.65 | 354.13 | 100.00% |
| 12 | 18.58 | 238.27 | 67.28% |
| 13 | 18.98 | 343.93 | 97.12% |
| 14 | 20.25 | 175.26 | 49.49% |
| 15 | 21.96 | 139.02 | 39.26% |
| 16 | 22.66 | 170.41 | 48.12% |
| 17 | 22.91 | 141.39 | 39.93% |
| 18 | 24.46 | 82.18 | 23.21% |
| 19 | 25.81 | 25.82 | 7.29% |
| 20 | 27.23 | 55.43 | 15.65% |
| 21 | 28.45 | 31.41 | 8.87% |
| 22 | 29.95 | 51.64 | 14.58% |
| 23 | 31.47 | 48.69 | 13.75% |
| 24 | 34.26 | 32.94 | 9.30% |

TABLE 22

Observed XRPD signals and relative intensities of K Type E solid form identified in Table 7.

| No. | Pos. [°2θ] ± 0.2 | Height [cts] | Relative Intensity |
|---|---|---|---|
| 1 | 3.63 | 285.55 | 11.03% |
| 2 | 7.14 | 562.28 | 21.71% |
| 3 | 10.69 | 2589.71 | 100.00% |
| 4 | 11.14 | 424.50 | 16.39% |
| 5 | 12.91 | 225.03 | 8.69% |
| 6 | 14.23 | 728.05 | 28.11% |
| 7 | 15.87 | 88.03 | 3.40% |
| 8 | 17.87 | 199.07 | 7.69% |
| 9 | 18.89 | 108.74 | 4.20% |
| 10 | 20.52 | 97.48 | 3.76% |
| 11 | 21.37 | 684.70 | 26.44% |
| 12 | 22.31 | 90.75 | 3.50% |
| 13 | 24.95 | 217.61 | 8.40% |
| 14 | 25.87 | 177.05 | 6.84% |
| 15 | 29.81 | 40.38 | 1.56% |
| 16 | 39.17 | 82.27 | 3.18% |

TABLE 23

Observed XRPD signals and relative intensities of DEA Type A solid form identified in Table 7

| No. | Pos. [°2θ] ± 0.2 | Height [cts] | Relative Intensity |
|---|---|---|---|
| 1 | 4.12 | 518.72 | 15.57% |
| 2 | 5.95 | 331.34 | 9.94% |
| 3 | 8.17 | 118.20 | 3.55% |
| 4 | 9.80 | 222.10 | 6.66% |
| 5 | 11.87 | 1399.55 | 42.00% |
| 6 | 12.09 | 3332.51 | 100.00% |
| 7 | 12.30 | 2008.37 | 60.27% |
| 8 | 14.08 | 200.78 | 6.02% |
| 9 | 15.04 | 183.51 | 5.51% |
| 10 | 16.14 | 141.54 | 4.25% |
| 11 | 17.48 | 163.04 | 4.89% |
| 12 | 17.81 | 400.93 | 12.03% |
| 13 | 18.27 | 964.71 | 28.95% |
| 14 | 19.43 | 925.72 | 27.78% |
| 15 | 20.22 | 455.44 | 13.67% |
| 16 | 20.53 | 277.29 | 8.32% |
| 17 | 21.03 | 140.88 | 4.23% |
| 18 | 21.69 | 435.70 | 13.07% |
| 19 | 23.39 | 141.17 | 4.24% |
| 20 | 24.13 | 151.00 | 4.53% |
| 21 | 24.71 | 81.72 | 2.45% |
| 22 | 25.55 | 106.05 | 3.18% |
| 23 | 27.15 | 357.88 | 10.74% |
| 24 | 27.99 | 92.23 | 2.77% |
| 25 | 30.90 | 152.77 | 4.58% |
| 26 | 36.03 | 117.97 | 3.54% |

TABLE 24

Observed XRPD signals and relative intensities of DEA Type B solid form identified in Table 7.

| No. | Pos. [°2θ] ± 0.2 | Height [cts] | Relative Intensity |
|---|---|---|---|
| 1 | 9.21 | 68.97 | 2.71% |
| 2 | 10.77 | 745.84 | 29.34% |
| 3 | 11.80 | 2541.77 | 100.00% |
| 4 | 13.33 | 314.56 | 12.38% |
| 5 | 15.09 | 1252.59 | 49.28% |
| 6 | 15.73 | 171.00 | 6.73% |
| 7 | 17.25 | 802.00 | 31.55% |
| 8 | 17.58 | 1530.11 | 60.20% |
| 9 | 18.08 | 399.41 | 15.71% |
| 10 | 18.89 | 524.54 | 20.64% |
| 11 | 19.69 | 1243.79 | 48.93% |
| 12 | 20.54 | 191.71 | 7.54% |
| 13 | 20.82 | 562.40 | 22.13% |
| 14 | 21.65 | 192.69 | 7.58% |
| 15 | 22.02 | 70.43 | 2.77% |
| 16 | 23.31 | 379.94 | 14.95% |
| 17 | 23.61 | 359.88 | 14.16% |
| 18 | 23.97 | 96.05 | 3.78% |
| 19 | 24.57 | 68.73 | 2.70% |
| 20 | 25.28 | 135.94 | 5.35% |
| 21 | 26.10 | 238.66 | 9.39% |
| 22 | 27.07 | 188.24 | 7.41% |
| 23 | 28.22 | 45.26 | 1.78% |
| 24 | 29.62 | 76.08 | 2.99% |
| 25 | 30.38 | 90.09 | 3.54% |
| 26 | 30.99 | 120.80 | 4.75% |
| 27 | 33.00 | 35.23 | 1.39% |
| 28 | 33.95 | 27.13 | 1.07% |
| 29 | 34.85 | 83.85 | 3.30% |
| 30 | 36.36 | 34.08 | 1.34% |
| 31 | 38.07 | 36.14 | 1.42% |

TABLE 25

Observed XRPD signals and relative intensities of DEA Type C solid form identified in Table 7.

| No. | Pos. [°2θ] ± 0.2 | Height [cts] | Relative Intensity |
|---|---|---|---|
| 1 | 4.05 | 381.97 | 18.59% |
| 2 | 8.11 | 146.25 | 7.12% |
| 3 | 12.16 | 2054.37 | 100.00% |
| 4 | 14.98 | 271.77 | 13.23% |
| 5 | 16.07 | 184.37 | 8.97% |
| 6 | 16.99 | 363.74 | 17.71% |
| 7 | 17.47 | 311.66 | 15.17% |
| 8 | 18.40 | 415.67 | 20.23% |
| 9 | 19.32 | 270.03 | 13.14% |
| 10 | 20.18 | 290.33 | 14.13% |
| 11 | 20.44 | 439.14 | 21.38% |
| 12 | 21.64 | 113.02 | 5.50% |
| 13 | 22.45 | 153.83 | 7.49% |
| 14 | 24.61 | 202.17 | 9.84% |

TABLE 26

Observed XRPD signals and relative intensities of Lysine Type A solid form identified in Table 7.

| No. | Pos. [°2θ] ± 0.2 | Height [cts] | Relative Intensity |
|---|---|---|---|
| 1 | 3.43 | 2797.43 | 47.20% |
| 2 | 6.76 | 2959.18 | 49.93% |
| 3 | 7.57 | 281.18 | 4.74% |
| 4 | 8.66 | 166.67 | 2.81% |
| 5 | 10.14 | 4958.94 | 83.67% |
| 6 | 10.31 | 5926.61 | 100.00% |
| 7 | 11.11 | 971.69 | 16.40% |
| 8 | 13.51 | 2246.65 | 37.91% |
| 9 | 14.79 | 558.65 | 9.43% |
| 10 | 15.14 | 464.33 | 7.83% |
| 11 | 15.85 | 229.69 | 3.88% |
| 12 | 16.18 | 374.36 | 6.32% |
| 13 | 16.89 | 494.29 | 8.34% |
| 14 | 17.21 | 694.07 | 11.71% |
| 15 | 18.06 | 783.56 | 13.22% |
| 16 | 19.22 | 543.72 | 9.17% |
| 17 | 19.41 | 676.84 | 11.42% |
| 18 | 20.27 | 679.04 | 11.46% |
| 19 | 20.68 | 387.62 | 6.54% |
| 20 | 21.10 | 299.00 | 5.05% |
| 21 | 22.28 | 469.67 | 7.92% |
| 22 | 22.72 | 236.74 | 3.99% |
| 23 | 23.07 | 235.69 | 3.98% |
| 24 | 23.75 | 1376.54 | 23.23% |
| 25 | 24.14 | 743.12 | 12.54% |
| 26 | 24.77 | 216.86 | 3.66% |
| 27 | 26.01 | 187.47 | 3.16% |
| 28 | 27.19 | 229.63 | 3.87% |
| 29 | 28.12 | 75.63 | 1.28% |
| 30 | 28.89 | 54.30 | 0.92% |
| 31 | 29.72 | 42.23 | 0.71% |
| 32 | 30.73 | 76.83 | 1.30% |
| 33 | 31.63 | 55.24 | 0.93% |
| 34 | 34.65 | 29.30 | 0.49% |

TABLE 27

Observed XRPD signals and relative intensities of Lysine Type B solid form identified in Table 7.

| No. | Pos. [°2θ] ± 0.2 | Height [cts] | Relative Intensity |
|---|---|---|---|
| 1 | 3.12 | 1561.94 | 100.00% |
| 2 | 5.12 | 853.52 | 54.64% |
| 3 | 18.74 | 83.72 | 5.36% |
| 4 | 19.66 | 80.95 | 5.18% |
| 5 | 20.65 | 85.89 | 5.50% |

TABLE 28

Observed XRPD signals and relative intensities of Lysine Type C solid form identified in Table 7.

| No. | Pos. [°2θ] ± 0.2 | Height [cts] | Relative Intensity |
|---|---|---|---|
| 1 | 3.28 | 77.55 | 2.69% |
| 2 | 6.73 | 949.71 | 32.93% |
| 3 | 10.17 | 2884.30 | 100.00% |
| 4 | 10.95 | 1312.09 | 45.49% |
| 5 | 13.38 | 585.84 | 20.31% |
| 6 | 13.63 | 1637.21 | 56.76% |
| 7 | 14.01 | 292.01 | 10.12% |
| 8 | 15.21 | 360.78 | 12.51% |
| 9 | 16.51 | 302.36 | 10.48% |
| 10 | 17.08 | 426.44 | 14.78% |
| 11 | 17.55 | 708.62 | 24.57% |
| 12 | 18.22 | 255.41 | 8.86% |
| 13 | 18.66 | 273.38 | 9.48% |
| 14 | 19.02 | 268.15 | 9.30% |
| 15 | 19.95 | 413.99 | 14.35% |
| 16 | 20.21 | 386.98 | 13.42% |
| 17 | 20.60 | 305.52 | 10.59% |
| 18 | 20.96 | 320.20 | 11.10% |
| 19 | 22.18 | 721.99 | 25.03% |
| 20 | 22.43 | 442.08 | 15.33% |
| 21 | 23.23 | 273.51 | 9.48% |
| 22 | 23.73 | 168.31 | 5.84% |
| 23 | 24.12 | 1321.00 | 45.80% |
| 24 | 24.54 | 237.08 | 8.22% |

TABLE 28-continued

Observed XRPD signals and relative intensities of Lysine Type C solid form identified in Table 7.

| No. | Pos. [°2θ] ± 0.2 | Height [cts] | Relative Intensity |
|---|---|---|---|
| 25 | 25.10 | 161.10 | 5.59% |
| 26 | 25.80 | 53.85 | 1.87% |
| 27 | 27.15 | 328.10 | 11.38% |
| 28 | 27.66 | 106.56 | 3.69% |
| 29 | 28.25 | 45.48 | 1.58% |
| 30 | 28.89 | 40.85 | 1.42% |
| 31 | 30.18 | 113.04 | 3.92% |
| 32 | 30.97 | 53.64 | 1.86% |
| 33 | 32.02 | 77.43 | 2.68% |
| 34 | 33.20 | 88.52 | 3.07% |
| 35 | 35.92 | 32.85 | 1.14% |

TABLE 29

Observed XRPD signals and relative intensities of Lysine Type D solid form identified in Table 7.

| No. | Pos. [°2θ] ± 0.2 | Height [cts] | Relative Intensity |
|---|---|---|---|
| 1 | 3.52 | 1250.15 | 40.62% |
| 2 | 6.96 | 1138.64 | 37.00% |
| 3 | 10.44 | 3077.81 | 100.00% |
| 4 | 11.40 | 443.04 | 14.39% |
| 5 | 13.93 | 2654.27 | 86.24% |
| 6 | 15.21 | 276.51 | 8.98% |
| 7 | 16.28 | 144.79 | 4.70% |
| 8 | 17.74 | 592.09 | 19.24% |
| 9 | 18.73 | 198.23 | 6.44% |
| 10 | 19.32 | 282.05 | 9.16% |
| 11 | 20.05 | 513.43 | 16.68% |
| 12 | 20.94 | 831.07 | 27.00% |
| 13 | 22.83 | 528.33 | 17.17% |
| 14 | 23.60 | 170.55 | 5.54% |
| 15 | 24.47 | 495.65 | 16.10% |
| 16 | 27.66 | 85.44 | 2.78% |
| 17 | 28.06 | 112.63 | 3.66% |
| 18 | 36.71 | 30.45 | 0.99% |

TABLE 30

Observed XRPD signals and relative intensities of Glycine Type A solid form identified in Table 7.

| No. | Pos. [°2θ] ± 0.2 | Height [cts] | Relative Intensity |
|---|---|---|---|
| 1 | 14.57 | 260.72 | 7.16% |
| 2 | 18.03 | 364.05 | 10.00% |
| 3 | 21.85 | 1775.00 | 48.77% |
| 4 | 23.98 | 40.16 | 1.10% |
| 5 | 25.35 | 3639.56 | 100.00% |
| 6 | 29.34 | 534.71 | 14.69% |
| 7 | 30.22 | 264.59 | 7.27% |
| 8 | 33.68 | 161.19 | 4.43% |
| 9 | 35.97 | 777.80 | 21.37% |
| 10 | 39.13 | 602.34 | 16.55% |

TABLE 31

Observed XRPD signals and relative intensities of NH₄ Type A solid form identified in Table 7.

| No. | Pos. [°2θ] ± 0.2 | Height [cts] | Relative Intensity |
|---|---|---|---|
| 1 | 3.30 | 113.95 | 6.87% |
| 2 | 4.18 | 171.22 | 10.32% |
| 3 | 4.73 | 1659.52 | 100.00% |
| 4 | 6.57 | 113.79 | 6.86% |
| 5 | 6.94 | 180.07 | 10.85% |
| 6 | 8.04 | 51.90 | 3.13% |
| 7 | 9.81 | 748.63 | 45.11% |
| 8 | 10.61 | 664.79 | 40.06% |
| 9 | 11.17 | 537.35 | 32.38% |
| 10 | 11.55 | 544.89 | 32.83% |
| 11 | 11.83 | 331.96 | 20.00% |
| 12 | 12.89 | 169.04 | 10.19% |
| 13 | 13.88 | 521.75 | 31.44% |
| 14 | 14.21 | 846.17 | 50.99% |
| 15 | 16.14 | 1339.73 | 80.73% |
| 16 | 16.71 | 320.48 | 19.31% |
| 17 | 17.56 | 267.32 | 16.11% |
| 18 | 17.74 | 364.34 | 21.95% |
| 19 | 18.43 | 399.42 | 24.07% |
| 20 | 18.80 | 240.79 | 14.51% |
| 21 | 19.66 | 604.01 | 36.40% |
| 22 | 20.95 | 376.26 | 22.67% |
| 23 | 21.37 | 336.06 | 20.25% |
| 24 | 22.50 | 157.78 | 9.51% |
| 25 | 22.73 | 265.52 | 16.00% |
| 26 | 23.18 | 486.18 | 29.30% |
| 27 | 23.73 | 271.43 | 16.36% |
| 28 | 24.12 | 148.68 | 8.96% |
| 29 | 24.64 | 433.50 | 26.12% |
| 30 | 25.36 | 441.44 | 26.60% |
| 31 | 25.86 | 377.40 | 22.74% |
| 32 | 26.21 | 214.32 | 12.91% |
| 33 | 26.65 | 71.84 | 4.33% |
| 34 | 27.73 | 96.74 | 5.83% |
| 35 | 30.09 | 80.21 | 4.83% |
| 36 | 31.07 | 36.74 | 2.21% |
| 37 | 34.87 | 20.30 | 1.22% |

TABLE 32

Observed XRPD signals and relative intensities of NH₄ Type B solid form identified in Table 7.

| No. | Pos. [°2θ] ± 0.2 | Height [cts] | Relative Intensity |
|---|---|---|---|
| 1 | 5.76 | 1086.46 | 86.31% |
| 2 | 6.01 | 427.79 | 33.98% |
| 3 | 7.52 | 390.79 | 31.04% |
| 4 | 7.95 | 269.27 | 21.39% |
| 5 | 10.28 | 1258.85 | 100.00% |
| 6 | 11.18 | 446.03 | 35.43% |
| 7 | 11.48 | 365.64 | 29.05% |
| 8 | 11.93 | 107.85 | 8.57% |
| 9 | 13.36 | 436.86 | 34.70% |
| 10 | 13.99 | 137.30 | 10.91% |
| 11 | 15.08 | 80.67 | 6.41% |
| 12 | 15.93 | 130.00 | 10.33% |
| 13 | 16.42 | 275.30 | 21.87% |
| 14 | 16.68 | 375.28 | 29.81% |
| 15 | 17.00 | 449.23 | 35.69% |
| 16 | 17.24 | 438.94 | 34.87% |
| 17 | 17.85 | 169.00 | 13.42% |
| 18 | 18.55 | 71.40 | 5.67% |
| 19 | 19.64 | 119.08 | 9.46% |
| 20 | 20.14 | 106.43 | 8.45% |
| 21 | 20.62 | 219.51 | 17.44% |
| 22 | 22.52 | 325.72 | 25.87% |
| 23 | 22.96 | 424.49 | 33.72% |
| 24 | 23.64 | 255.73 | 20.31% |
| 25 | 27.20 | 49.41 | 3.93% |
| 26 | 30.20 | 40.92 | 3.25% |

TABLE 33

Observed XRPD signals and relative intensities of $NH_4$ Type C solid form identified in Table 7.

| No. | Pos. [°2θ] ± 0.2 | Height [cts] | Relative Intensity |
|---|---|---|---|
| 1 | 3.71 | 561.45 | 52.64% |
| 2 | 4.57 | 599.42 | 56.20% |
| 3 | 5.68 | 675.10 | 63.30% |
| 4 | 7.35 | 321.98 | 30.19% |
| 5 | 8.37 | 59.24 | 5.55% |
| 6 | 9.62 | 547.09 | 51.30% |
| 7 | 10.98 | 1066.55 | 100.00% |
| 8 | 11.33 | 486.24 | 45.59% |
| 9 | 12.01 | 782.66 | 73.38% |
| 10 | 13.92 | 361.32 | 33.88% |
| 11 | 14.63 | 967.38 | 90.70% |
| 12 | 15.13 | 265.27 | 24.87% |
| 13 | 17.14 | 549.69 | 51.54% |
| 14 | 18.28 | 496.05 | 46.51% |
| 15 | 19.26 | 864.50 | 81.06% |
| 16 | 20.74 | 203.40 | 19.07% |
| 17 | 22.19 | 230.85 | 21.64% |
| 18 | 22.91 | 185.73 | 17.41% |
| 19 | 23.57 | 437.58 | 41.03% |
| 20 | 24.78 | 403.29 | 37.81% |
| 21 | 25.87 | 34.16 | 3.20% |
| 22 | 27.53 | 57.66 | 5.41% |
| 23 | 28.06 | 63.41 | 5.95% |
| 24 | 29.05 | 92.85 | 8.71% |

TABLE 34

Observed XRPD signals and relative intensities of $NH_4$ Type D solid form identified in Table 7.

| No. | Pos. [°2θ] ± 0.2 | Height [cts] | Relative Intensity |
|---|---|---|---|
| 1 | 8.00 | 83.02 | 7.30% |
| 2 | 9.03 | 331.20 | 29.13% |
| 3 | 9.56 | 513.38 | 45.16% |
| 4 | 10.73 | 591.44 | 52.02% |
| 5 | 11.41 | 1054.34 | 92.74% |
| 6 | 12.65 | 238.34 | 20.96% |
| 7 | 13.52 | 872.41 | 76.74% |
| 8 | 13.90 | 217.52 | 19.13% |
| 9 | 14.39 | 652.27 | 57.37% |
| 10 | 15.37 | 276.38 | 24.31% |
| 11 | 16.21 | 219.17 | 19.28% |
| 12 | 16.56 | 239.82 | 21.09% |
| 13 | 17.22 | 370.91 | 32.63% |
| 14 | 18.04 | 961.41 | 84.57% |
| 15 | 18.32 | 1136.86 | 100.00% |
| 16 | 18.77 | 944.80 | 83.11% |
| 17 | 19.03 | 597.49 | 52.56% |
| 18 | 19.40 | 461.92 | 40.63% |
| 19 | 20.20 | 173.47 | 15.26% |
| 20 | 21.10 | 109.30 | 9.61% |
| 21 | 21.79 | 156.86 | 13.80% |
| 22 | 22.85 | 913.88 | 80.39% |
| 23 | 23.21 | 626.43 | 55.10% |
| 24 | 23.72 | 666.55 | 58.63% |
| 25 | 24.36 | 505.97 | 44.51% |
| 26 | 25.10 | 121.34 | 10.67% |
| 27 | 25.99 | 56.53 | 4.97% |
| 28 | 27.21 | 204.21 | 17.96% |
| 29 | 27.72 | 97.66 | 8.59% |
| 30 | 28.18 | 176.90 | 15.56% |
| 31 | 28.74 | 59.49 | 5.23% |
| 32 | 30.63 | 16.51 | 1.45% |
| 33 | 32.95 | 17.61 | 1.55% |

TABLE 35

Observed XRPD signals and relative intensities of Mg Type A solid form identified in Table 7.

| No. | Pos. [°2θ] ± 0.2 | Height [cts] | Relative Intensity |
|---|---|---|---|
| 1 | 4.07 | 158.68 | 24.36% |
| 2 | 8.11 | 70.48 | 10.82% |
| 3 | 9.79 | 201.05 | 30.87% |
| 4 | 11.07 | 304.95 | 46.82% |
| 5 | 11.57 | 455.79 | 69.97% |
| 6 | 12.54 | 651.37 | 100.00% |
| 7 | 13.36 | 54.93 | 8.43% |
| 8 | 15.37 | 326.05 | 50.06% |
| 9 | 16.48 | 185.88 | 28.54% |
| 10 | 17.95 | 328.58 | 50.44% |
| 11 | 19.12 | 177.22 | 27.21% |
| 12 | 19.64 | 260.22 | 39.95% |
| 13 | 20.46 | 151.71 | 23.29% |
| 14 | 20.98 | 127.87 | 19.63% |
| 15 | 23.18 | 82.81 | 12.71% |

TABLE 36

Observed XRPD signals and relative intensities of Mg Type B solid form identified in Table 7.

| No. | Pos. [°2θ] ± 0.2 | Height [cts] | Relative Intensity |
|---|---|---|---|
| 1 | 4.14 | 534.00 | 100.00% |
| 2 | 18.00 | 78.00 | 14.61% |

TABLE 37

Observed XRPD signals and relative intensities of Ca Type A solid form identified in Table 7.

| No. | Pos. [°2θ] ± 0.2 | Height [cts] | Relative Intensity |
|---|---|---|---|
| 1 | 3.64 | 1390.29 | 100.00% |
| 2 | 3.96 | 251.71 | 18.10% |
| 3 | 7.30 | 408.56 | 29.39% |
| 4 | 10.96 | 532.77 | 38.32% |
| 5 | 11.64 | 210.09 | 15.11% |
| 6 | 14.51 | 102.65 | 7.38% |
| 7 | 16.60 | 111.28 | 8.00% |
| 8 | 17.86 | 136.88 | 9.85% |
| 9 | 19.44 | 151.95 | 10.93% |
| 10 | 27.75 | 32.03 | 2.30% |
| 11 | 28.70 | 25.04 | 1.80% |

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A salt of (2E,4E)-3-methyl-5-((1S,2S)-2-methyl-2-(5,5,8,8-tetramethyl-5,6,7,8-tetrahydronaphthalen-2-yl)cyclopropyl)penta-2,4-dienoic acid, which is an anhydrate, hemihydrate, monohydrate, or dihydrate of (2E,4E)-3-methyl-5-((1S,2S)-2-methyl-2-(5,5,8,8-tetramethyl-5,6,7,8-tetrahydronaphthalen-2-yl)cyclopropyl)penta-2,4-dienoic acid tris(hydroxymethyl)aminomethane.

2. A solid form, which is Form A of the salt (2E,4E)-3-methyl-5-((1S,2S)-2-methyl-2-(5,5,8,8-tetramethyl-5,6,7,8-tetrahydronaphthalen-2-yl)cyclopropyl)penta-2,4-dienoic acid mono-(tris(hydroxymethyl)aminomethane).

3. The solid form of claim 2, having an X-ray powder diffraction pattern comprising a signal, in terms of 2θ, at 11.3±0.2°.

4. The solid form of claim 2, having an X-ray powder diffraction pattern comprising signals, in terms of 2θ, at 3.8±0.2°, 7.6±0.2°, 11.3±0.2°, 18.1±0.2°, and 19.6±0.2°.

5. The solid form of claim 2, having an X-ray powder diffraction pattern substantially as shown in FIG. 1.

6. The solid form of claim 2, having a differential scanning calorimetry thermogram comprising an endothermic transition at 154±3° C.

7. The solid form of claim 2, having a differential scanning calorimetry thermogram substantially as shown in FIG. 2.

8. The solid form of claim 2, having a thermogravimetric analysis substantially as shown in FIG. 3.

9. A solid form, which is Form B of the salt (2E,4E)-3-methyl-5-((1 S,2S)-2-methyl-2-(5,5,8,8-tetramethyl-5,6,7,8-tetrahydronaphthalen-2-v1)cyclopropyl)penta-2,4-dienoic acid mono-(tris(hydroxymethyl)aminomethane).

10. The solid form of claim 9, having an X-ray powder diffraction pattern comprising a signal, in terms of 2θ, at 11.5±0.2°.

11. The solid form of claim 9, having an X-ray powder diffraction pattern comprising signals, in terms of 2θ, at 3.9±0.2°, 11.5±0.2°, 18.3±0.2°, 19.9±0.2°, and 23.2±0.2°.

12. The solid form of claim 9, having an X-ray powder diffraction pattern substantially as shown in FIG. 4.

13. The solid form of claim 9, having a differential scanning calorimetry thermogram comprising an endothermic transition at 150±3° C.

14. The solid form of claim 9, having a differential scanning calorimetry thermogram substantially as shown in FIG. 5.

15. The solid form of claim 9, having a thermogravimetric analysis substantially as shown in FIG. 6.

16. The solid form of claim 2, which is substantially purified.

17. The solid form of claim 2, which is crystalline.

18. The solid form of claim 2, prepared by a process comprising precipitating the solid form from a solution comprising (2E,4E)-3-methyl-5-((1S,2S)-2-methyl-2-(5,5,8,8-tetramethyl-5,6,7,8-tetrahydronaphthalen-2-yl)cyclopropyl)penta-2,4-dienoic acid tris(hydroxymethyl)aminomethane and a solvent.

19. The solid form of claim 18, wherein the solvent comprises ethanol, isopropanol, butanol, or a combination thereof, and the solvent further comprises 0 to about 1 volume % of water.

20. A process for preparing the solid form of claim 2, comprising precipitating the solid form from a solution comprising (2E,4E)-3-methyl-5-((1S,2S)-2-methyl-2-(5,5,8,8-tetramethyl-5,6,7,8-tetrahydronaphthalen-2-yl)cyclopropyl)penta-2,4-dienoic acid tris(hydroxymethyl)aminomethane and a solvent,
    wherein the solvent comprises ethanol, isopropanol, butanol, or a combination thereof, and the solvent further comprises 0 to about 1 volume % of water.

\* \* \* \* \*